US012539374B2

(12) United States Patent
Guo et al.

(10) Patent No.: US 12,539,374 B2
(45) Date of Patent: Feb. 3, 2026

(54) SYSTEMS, DEVICES AND METHODS FOR DISPENSING BIOCOMPATIBLE REACTIVE FORMULATIONS AND CONTROLLING CROSS-LINKING OF THE REACTIVE COMPONENTS OF THE BIOCOMPATIBLE REACTIVE FORMULATIONS

(71) Applicant: Ethicon, Inc., Somerville, NJ (US)

(72) Inventors: Jianxin Guo, Livingston, NJ (US); Salim Ghodbane, Piscataway, NJ (US); Sridevi Dhanaraj, Raritan, NJ (US)

(73) Assignee: Ethicon, Inc., Somerville, NJ (US)

( * ) Notice: Subject to any disclaimer, the term of this patent is extended or adjusted under 35 U.S.C. 154(b) by 1025 days.

(21) Appl. No.: 17/672,807

(22) Filed: Feb. 16, 2022

(65) Prior Publication Data

US 2022/0265938 A1 Aug. 25, 2022

Related U.S. Application Data

(60) Provisional application No. 63/151,253, filed on Feb. 19, 2021.

(51) Int. Cl.
*A61M 11/06* (2006.01)
*A61J 1/20* (2006.01)
(Continued)

(52) U.S. Cl.
CPC ............ *A61M 11/06* (2013.01); *A61J 1/2093* (2013.01); *A61K 38/363* (2013.01); *A61K 38/4833* (2013.01)

(58) Field of Classification Search
CPC .. A61M 11/06; A61M 11/007; A61M 5/2448; A61M 5/19; A61M 2202/0468; A61M 2206/14; A61M 2206/16; A61M 2209/06; A61M 15/0003; A61J 1/2093; A61K 38/363; A61K 38/4833; B01F 2101/22; B01F 2101/2202; B01F 25/3131; B01F 25/31331; B01F 25/434; B01F 25/4413; B01F 33/50112; B01F 35/715; B05B 1/3436; B05B 7/0408;
(Continued)

(56) References Cited

U.S. PATENT DOCUMENTS 4,357,110 A * 11/1982 Hope ...................... B01F 23/00 366/132
4,533,123 A * 8/1985 O'Leary ........... B01F 33/40511 261/61
(Continued)

FOREIGN PATENT DOCUMENTS

| | | | |
|---|---|---|---|
| DE | 3200861 A1 * | 7/1983 |
| DE | 10226803 | 1/2003 |
| EP | 1113839 | 11/2004 |

OTHER PUBLICATIONS

International Search Report issued in corresponding International Application No. PCT/IB2022/051382, dated May 23, 2022, 5 pages.

*Primary Examiner* — Tan-Uyen T Ho
*Assistant Examiner* — Osama Nemer

(57) ABSTRACT

A system for dispensing a biocompatible reactive formulation includes a first chamber containing a first fluid having a first reactive component, a second chamber containing a second fluid having a second reactive component, and a third chamber containing a third fluid.

15 Claims, 45 Drawing Sheets

(51) Int. Cl.
*A61K 38/36* (2006.01)
*A61K 38/48* (2006.01)

(58) Field of Classification Search
CPC ................. B05B 11/0078; B05B 11/02; B05C 17/00553; A61B 2017/00495; A61B 2017/00522; A61B 17/00491
See application file for complete search history.

(56) References Cited

U.S. PATENT DOCUMENTS

| | | | | |
|---|---|---|---|---|
| 4,842,581 | A * | 6/1989 | Davis .................... | A61M 1/772 604/218 |
| 5,484,107 | A * | 1/1996 | Holmes ................. | B05B 7/0475 239/428 |
| 5,887,755 | A * | 3/1999 | Hood, III ................ | B01F 25/25 222/394 |
| 6,830,756 | B2 | 12/2004 | Hnojewyj | |
| 6,874,657 | B2 * | 4/2005 | Metzner .................... | A61P 7/04 222/391 |
| 8,377,507 | B2 | 2/2013 | Wawrzyniak et al. | |
| 8,876,021 | B2 * | 11/2014 | Fortier .................. | B05B 15/652 604/82 |
| 9,328,301 | B2 * | 5/2016 | Wang ...................... | C01B 3/363 |
| 9,421,565 | B2 * | 8/2016 | Lewis ..................... | C08L 75/02 |
| 9,572,555 | B1 | 2/2017 | Lai et al. | |
| 10,085,729 | B2 | 10/2018 | Jamiolkowski et al. | |
| 10,166,514 | B2 * | 1/2019 | Delmotte ................. | A61K 9/12 |
| 10,231,720 | B2 | 3/2019 | Goodman et al. | |
| 10,967,343 | B2 * | 4/2021 | Devitt ..................... | A61M 5/19 |
| 12,114,843 | B2 * | 10/2024 | Guo ................. | A61B 17/00491 |
| 2007/0225645 | A1 * | 9/2007 | Tarinelli .............. | A61M 35/003 604/131 |
| 2010/0280312 | A1 * | 11/2010 | D'Alessio ........ | A61B 17/00491 606/213 |
| 2011/0245866 | A1 * | 10/2011 | Cassingham .... | A61B 17/00491 606/213 |
| 2012/0039147 | A1 * | 2/2012 | Greter ............... | B01F 33/50112 366/154.1 |
| 2012/0158048 | A1 | 6/2012 | Roush et al. | |
| 2014/0074154 | A1 * | 3/2014 | Goodman ......... | B01F 25/45212 606/213 |
| 2015/0250463 | A1 | 9/2015 | Jamiolkowski et al. | |
| 2021/0100543 | A1 | 4/2021 | Trezza, II et al. | |
| 2021/0101162 | A1 | 4/2021 | Trezza, II et al. | |
| 2022/0055048 | A1 * | 2/2022 | Paris ..................... | B05B 7/2467 |

* cited by examiner

FIG. 21C
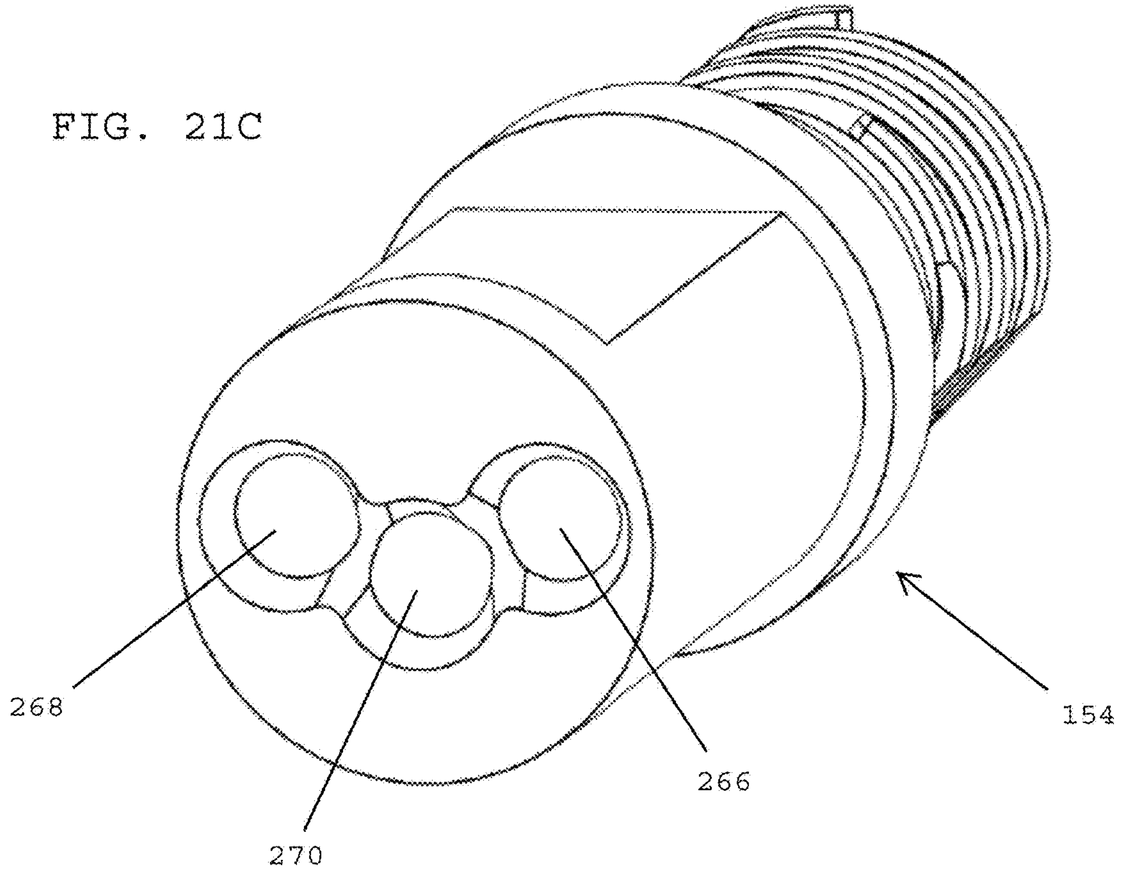
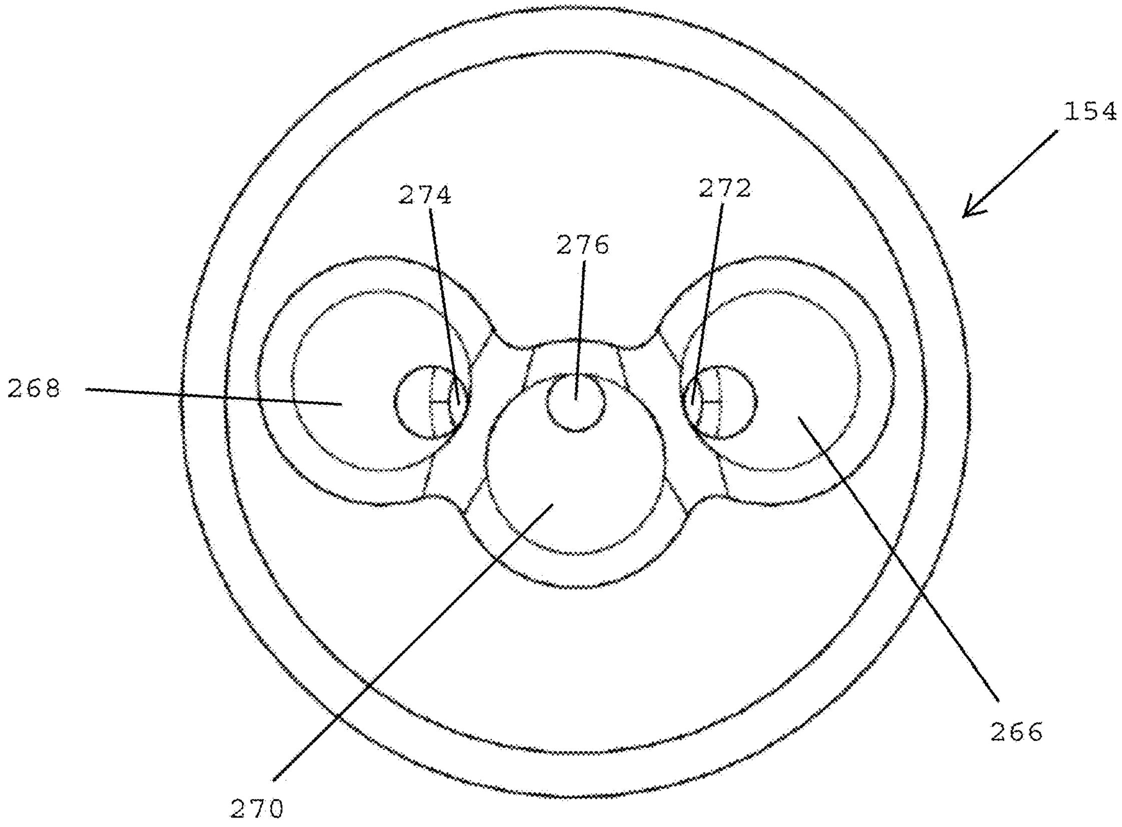
FIG. 21D

FIR. 24D

SYSTEMS, DEVICES AND METHODS FOR DISPENSING BIOCOMPATIBLE REACTIVE FORMULATIONS AND CONTROLLING CROSS-LINKING OF THE REACTIVE COMPONENTS OF THE BIOCOMPATIBLE REACTIVE FORMULATIONS

CROSS-REFERENCE TO RELATED APPLICATIONS

The present patent application claims benefit of U.S. Provisional Application Ser. No. 63/151,253, filed on Feb. 19, 2021, the disclosure of which is hereby incorporated by reference herein.

BACKGROUND OF THE INVENTION

Field of the Invention

The present patent application is generally related to biocompatible compositions used for sealing and hemostasis, and is more specifically related to systems, devices and methods for controlling the cross-linking of the reactive components of biocompatible reactive formulations.

Description of the Related Art

During a surgical procedure, incisions are created to access surgical sites. Once the surgical procedure has been completed, the incisions are closed for healing. In many instances, the incisions are closed with sutures or staples, however, tissue adhesives are also used for closing external incisions. In recent years, absorbable tissue adhesives have been developed for use in closing internal incisions.

Tissue adhesives and sealants include viscous gels that have little or no further curing after application, as well as compositions that solidify and/or cure once applied. Cyanoacrylates products such as Ethicon's Dermabond® and Covidien's Indermil® are examples of tissue adhesives that possess high strength and that cure in place. These materials polymerize to achieve the strength required, but do not offer the user any control over the time to curing. Without providing the ability to control of the degree of curing, they typically address only one clinical need, e.g., to close and hold incisions.

Other products such as Ethicon's synthetic Omnex™ and biological Evicel® and Cryolife's BioGlue® are examples of sealants that act to treat and prevent leakage. Once again, these materials typically address only one of the four clinical needs of acting as a sealant, acting as an adhesive, acting as a hemostatic agent, or acting as an adhesion preventing coating. The above-listed products do not offer the user the ability to change the performance characteristics to address different clinical needs.

Products such as Ethicon's Intercoat®, Genzyme's SepraGel®, Confluent's SprayGel®, and Covidien's SprayShield™, to name a few, are examples of adhesion barriers. These are either one of, or a combination of, hydrogels of PolyEthylene Glycol (PEG), Poly Vinyl Alcohol (PVA), CarboxyMethyl Cellulose (CMC), or HyaLuronic Acid (HLA). Once again, these materials typically only address one of the four clinical needs noted herein (e.g., to act as an adhesion prevention barrier), and do not provide users with the option to change the performance characteristics to address different clinical needs.

Although there may be some materials with properties mid-way between sealants and adhesion preventatives, their properties are not optimized for either application and they cannot be changed by the surgeon at the time of application during surgery. Many of the solutions that the art provides in the four areas of surgical adhesives, sealants, adhesion preventatives and hemostatic agents are based on cross-linkable systems. Initially, the product is flowable to allow application to a surgical site to be treated. After application, the product becomes non-flowable whereupon it stays in place to function properly.

The performance characteristics of the hydrogel products are intimately related to cross-link density. When cross-link density is high, mechanical strength is high and water swellability is low. High cross-link density hydrogels are often associated with products that function as adhesives. Sealants often require slightly less mechanical strength. As a result, hydrogel products in this category can have cross-link densities that are concomitantly slightly lower.

Finally, a class of surgical adhesion preventatives based on hydrogel technology is cross-linked at a much lower level than the other two product classes. Their lower cross-link density allows a greater amount of swellability leading to a very slippery behavior. This latter characteristic has been identified by some to contribute to the ability to prevent viscera from adhering to one another or the initiation of collagen deposition leading to adhesion formations. Likewise, clinically relevant properties of some hemostatic agents depend on the mixing ratios of components. For example, the mixing ratios of fibrinogen and thrombin alter the properties of the resulting matrix.

The above-identified products provide pre-determined properties to address unique clinical needs, however, the products provide physicians with no flexibility or choice to alter or dial in the properties for other clinical needs at the time of application during surgery.

There have been some attempts to overcome the above-noted deficiencies. For example, US 2015/0250463, assigned to Ethicon, Inc. of Somerville, New Jersey, the disclosure of which is hereby incorporated by reference herein, teaches a method of applying a coating onto tissue. The coating has at least two physiologically distinct layers that are delivered from a single device by delivery of a multi-part biomedical composition in different blended or mixing ratios. Disclosed methods include connecting at least two syringe barrels that contain inter-reacting components of the multi-part biomedical composition. Each syringe barrel has a piston that is internally slidable for expression of the components. The first syringe has a first retention compartment and a second retention compartment that are spaced axially therein, with a gasket positioned in the first retention compartment. The method includes advancing the pistons through each syringe to express onto a surface the reactive components of the multi-part biomedical composition in a first blended or mixing ratio, and continuing to advance the pistons to disengage a gasket from the piston of a first syringe at a point between the first retention compartment and the second retention compartment, and still further advancing the pistons through each syringe to express the reactive components of the multi-part biomedical composition in a second blended or mixing ratio to form a biomedical coating having physiologically distinct layers.

U.S. Pat. No. 6,830,756 to Hnojewyj discloses systems, methods, and compositions for achieving closure of vascular puncture sites. The systems and methods form a vascular closure composition by mixing together a first component, a second component, and a buffer material. The first component includes an electrophilic polymer material having a functionality of at least three. The second component includes a nucleophilic material that, when mixed with the first component within a reaction pH range of between 7 to 9, cross-links with the first component to form a non-liquid, three-dimensional barrier. The buffer material has a pH within the reaction pH range. The systems and methods apply the composition to seal a vascular puncture site.

Commonly assigned U.S. patent application Ser. No. 16/593,783, filed on Oct. 4, 2019, the disclosure of which is hereby by incorporated by reference herein, discloses a device with a spray tip for dispensing fluids that react together. The device includes a first lumen for a first fluid, a second lumen for a second fluid, and a dispensing cap located at distal ends of the respective first and second lumens that defines a distal end of the spray tip. The dispensing cap includes a distal end wall defining a closed end of the dispensing cap. A first spray opening is formed in the distal end wall that is in fluid communication with the first lumen, a second spray opening is formed in the distal end wall that is in fluid communication with the second lumen, and an external dividing wall projects distally from the distal end wall of the dispensing cap and extends between the first and second spray openings for forming a barrier between the first and second spray openings.

Commonly assigned U.S. patent application Ser. No. 16/593,799, filed on Oct. 4, 2019, the disclosure of which is hereby by incorporated by reference herein, discloses a spray device including a first spray tip having a first fluid pathway defining a first flow area, and a second spray tip including a second fluid pathway that defines a second flow area that is larger than the first flow area of the first spray tip. The first and second spray tips are side-by-side and spaced from one another at a distal end of the spray device. When a first fluid having a volumetric flow rate is introduced into the first spray tip and a second fluid having the same volumetric flow rate is introduced into the second spray tip, the first fluid will flow through the first fluid pathway at a greater velocity than the second fluid will flow through the second fluid pathway.

Commonly assigned U.S. Provisional Application Ser. No. 63/127,308, filed on Dec. 18, 2020, the disclosure of which is hereby by incorporated by reference herein, discloses a method of making a biocompatible composition for sealing tissue includes mixing a first fluid having a first reactive component (e.g., an electrophile) and a second fluid having a second reactive component (e.g., a nucleophile) to form a mixture and expressing the mixture. During expression, a pH modifying fluid (e.g., NaOH) is added to the mixture at a rate that changes. In one embodiment, a higher ratio of the pH modifying fluid is added to the mixture during a first expressing stage and a lower ratio of the pH modifying fluid is added to the mixture during a second expressing stage. During the first expressing stage, a mixing ratio of the pH modifying fluid, the first fluid and the second fluid is 0.7-1.4:1:1. During the second expressing stage, the mixing ratio of the pH modifying fluid, the first fluid and the second fluid is 0.12-0.24:1:1.

In spite of the above-identified advances, there remains a need for improved systems, devices and methods for controlling cross-linking of the reactive components of biocompatible reactive formulations for effectively sealing tissue and hemostasis.

SUMMARY OF THE INVENTION

In one embodiment, an applicator instrument for mixing and expressing biocompatible reactive formulations, such as tissue adhesives and sealants, preferably has a proximal end and a distal end including a spray tip assembly located at the distal end. In one embodiment, the applicator instrument is preferably configured for mixing together two or more fluid components (e.g., three components) to form a final mixture of a biocompatible reactive formulation (e.g., a tissue adhesive). In one embodiment, the final mixture of the biocompatible reactive formulation is preferably expressed from the spray tip assembly.

In one embodiment, the applicator instrument preferably includes a first syringe barrel that is adapted to contain a first reactive fluid of a multiple component reactive formulation (e.g., a tissue adhesive; a sealant). In one embodiment, the first syringe barrel is adapted to receive a first syringe plunger, which may be used for forcing the first reactive fluid from the distal end of the first syringe barrel.

In one embodiment, the applicator instrument preferably includes a second syringe barrel that is adapted to contain a second reactive fluid of the multiple component biocompatible reactive formulation. In one embodiment, the second syringe barrel is adapted to receive a second syringe plunger, which may be used for forcing the second reactive fluid from the distal end of the second syringe barrel. The first and second reactive fluids may be mixed together to form a first mixture. In one embodiment, the first and second reactive fluids may be adapted for chemically reacting with one another to form a biocompatible reactive formulation, such as an adhesive or a sealant. An adhesive may be used for bonding with a surface or between two surfaces, such as tissue to tissue bonding and tissue to biomaterial bonding. A sealant may be used to bond to tissue surrounding an opening such as a wound or incision to halt the ingress or egress of liquids and/or gases.

In one embodiment, the applicator instrument desirably includes the third syringe barrel, which is adapted to receive a third syringe plunger. In one embodiment, the third syringe barrel is adapted to contain a third fluid component (e.g., a neutralizing buffer; a diluent, such as $H_2O$). In one embodiment, the third syringe plunger may be depressed for forcing the third fluid component from the distal end of the third syringe barrel, whereupon the third fluid may be added into and/or mixed with the first mixture of the first and second reactive fluids.

In one embodiment, proximal ends of the syringe plungers are preferably secured to a plunger head, which may be depressed for simultaneously moving the syringe plungers in a distal direction to simultaneously dispense the first, second and third fluids from the distal ends of the respective first, second and third syringe barrels.

In one embodiment, the applicator instrument preferably includes a fluid manifold that is located downstream from the distal ends of the first, second and third syringe barrels. In one embodiment, the fluid manifold preferably includes a first connector adapted to receive a distal end of the first syringe barrel, a second connector adapted to receive a distal end of the second syringe barrel, and a third connector adapted to receive a distal end of the third syringe barrel.

In one embodiment, the first connector of the fluid manifold is preferably in fluid communication with the first syringe barrel. In one embodiment, a first component of a multiple component biocompatible reactive formulation that is pre-loaded into the first syringe barrel may be forced to flow into the first connector of the fluid manifold, such as by depressing the first syringe plunger.

In one embodiment, the second connector of the fluid manifold is preferably in fluid communication with the second syringe barrel. In one embodiment, a second component of a multiple component biocompatible reactive formulation that is pre-loaded into the second syringe barrel may be forced to flow into the second connector of the fluid manifold, such as by depressing the second syringe plunger.

In one embodiment, the third connector of the fluid manifold is preferably in fluid communication with the third syringe barrel. In one embodiment, a third component of a multiple component biocompatible reactive formulation that is pre-loaded into the third syringe barrel may be forced to flow into the third connector of the fluid manifold, such as by depressing the third syringe plunger.

In one embodiment, the applicator instrument preferably includes a syringe barrel support frame that is adapted to receive and hold the first, second and third syringe barrels. The syringe barrel support frame desirably holds the syringe barrels together for stabilizing the syringe barrels and enhancing the structural integrity and consistent performance of the applicator instrument.

In one embodiment, the syringe barrel support frame preferably has a distal end with a distal projection having threads, which are adapted to mesh with threads of a connecting nut for securing the distal end of the syringe barrel support frame to the connecting nut. In one embodiment, the connecting nut may also be utilized for securing both the distal projection of the syringe barrel support frame and the distal end of the third syringe barrel to the second connector of the fluid manifold.

In one embodiment, the distal end of the first syringe barrel is inserted into the first fluid inlet opening of the first connector of the fluid manifold. A first O-ring retainer and a first O-ring may be utilized to form a fluid-tight coupling between the distal end of the first syringe barrel and the first connector of the fluid manifold.

In one embodiment, the distal end of the second syringe barrel is inserted into the second fluid inlet opening of the second connector of the fluid dispensing manifold. A second O-ring retainer and a second O-ring may be utilized for forming a fluid-tight coupling between the distal end of the second syringe barrel and the second connector of the fluid manifold.

In one embodiment, the distal end of the third syringe barrel is inserted into the third fluid inlet opening of the third connector of the fluid dispensing manifold. A third O-ring retainer and a third O-ring may be utilized for forming a water-tight coupling between the distal end of the third syringe barrel and the third connector of the fluid manifold.

In one embodiment, a first fluid dispensing opening located at the distal end of the first syringe barrel is preferably in fluid communication with a first fluid tube for directing the first fluid of a mixture from the first syringe barrel into the first fluid tube.

In one embodiment, a second fluid dispensing opening located at the distal end of the second syringe barrel is preferably in fluid communication with a second fluid tube for directing the second fluid of a mixture from the second syringe barrel into the second fluid tube.

In one embodiment, a third dispensing opening at the distal end of the third syringe barrel is preferably in fluid communication with a third fluid tube for directing the third fluid of the mixture from the third syringe barrel into the third fluid tube.

In one embodiment, the applicator instrument may include a fluid tube enclosure including an upper fluid tube enclosure and a lower fluid tube enclosure that are assembled together and secured to a distal end of the fluid manifold. The fluid tubes preferably pass through the fluid tube enclosure. In one embodiment, the distal ends of the respective fluid tubes are preferably coupled with a fluid connector of the spray tip assembly.

In one embodiment, the distal end of the applicator instrument preferably includes a spray tip assembly, which may be secured to the distal ends of upper and lower fluid tube enclosures. In one embodiment, the spray tip assembly preferably includes a fluid connector having a distal end that is secured to a proximal end of a spray tip housing, and an O-ring that forms a fluid-tight seal between the fluid connector and the spray tip housing. The spray tip assembly desirably includes a mixing element that is disposed inside the spray tip housing. A dispensing cap may be secured to the distal end of the spray tip housing by inserting the dispensing cap into the elongated conduit of the spray tip housing.

In one embodiment, the first syringe barrel is adapted to receive a first fluid having a first reactive component (e.g., an electrophile) of a biocompatible reactive formulation. In one embodiment, the second syringe barrel is adapted to receive a second fluid having a second reactive component (e.g., a nucleophile) of a biocompatible reactive formulation, whereby the first and second fluids may be mixed together to form a first mixture. In one embodiment, the first and second fluids have reactive components that are adapted to chemically react with one another to form a biocompatible reactive formulation (e.g., an adhesive; a sealant) that is applied to tissue.

In one embodiment, the applicator instrument desirably includes a third syringe barrel that is adapted to contain a third fluid (e.g., a neutralizing buffer; a diluent) that may be added into the first mixture of the first and second fluids. In one embodiment, the third fluid may be added into and/or mixed with the first mixture of the first and second fluids to form a final mixture that is expressed from the spray tip assembly located at the distal end of the applicator instrument.

In one embodiment, the first fluid within the first syringe barrel may include an electrophile (e.g., PEG-NHS). In one embodiment, the second fluid within the second syringe barrel may include a nucleophile at high pH (e.g., PEG-$NH_2$). In one embodiment, the third fluid within the third syringe barrel may include a pH modifying buffer.

In one embodiment, the first fluid within the first syringe barrel may include an electrophile at high concentration (e.g., PEG-NHS), the second fluid within the second syringe barrel may include a nucleophile at high concentration (e.g., PEG-$NH_2$), and the third fluid within the third syringe barrel may include a diluent (e.g., $H_2O$; a buffer).

In one embodiment, the first and second fluids may include additions of polyelectrolytes such as alginate, heparin, hyaluronic acid, and chitosan.

In one embodiment, the third fluid may include polyvalent ions, such as Calcium.

In one embodiment, the first fluid includes Fibrinogen, the second fluid includes Thrombin, and the third fluid includes a diluent, such as $H_2O$.

In one embodiment, the spray tip assembly preferably includes the spray tip housing having a proximal end, a distal end, an outer wall that extends from the proximal end to the distal end of the spray tip housing, and an elongated conduit surrounded by the outer wall that extends from the proximal end to the distal end of the spray tip housing.

In one embodiment, the spray tip assembly desirably includes a mixing element disposed within the elongated conduit of the spray tip housing, and a mixing chamber located between an outer surface of the mixing element and an inner surface of the outer wall of the spray tip housing.

In one embodiment, the mixing element desirably includes a proximal end adjacent the proximal end of the spray tip housing and a distal end adjacent the distal end of the spray tip housing, a third fluid inlet opening at the proximal end of the mixing element, and one or more third fluid exit openings formed in the outer surface of the mixing element that are in fluid communication with the third fluid inlet opening, whereby the one or more third fluid exit openings extend laterally through the mixing element to the outer surface of the mixing element for being in fluid communication with the mixing chamber.

In one embodiment, the spray tip assembly preferably includes the fluid connector secured to the proximal end of the spray tip housing and opposing the proximal end of the mixing element. The fluid connector desirably includes first and second fluid channels in fluid communication with the mixing chamber, and a third fluid channel in fluid communication with the third fluid inlet opening of the mixing element.

In one embodiment, the mixing element preferably has a third fluid conduit extending distally from the third fluid inlet opening of the mixing element toward the distal end of the mixing element for interconnecting the third fluid inlet opening and the one or more third fluid exit openings of the mixing element.

In one embodiment, the fluid connector has a proximal end and a distal end, and the distal end of the fluid connector is disposed within the elongated conduit of the spray tip housing and opposes the proximal end of the mixing element.

In one embodiment, the first, second and third fluid channels of the fluid connector extend from the proximal end to the distal end of the fluid connector, and the first, second and third fluid channels are isolated from one another within the fluid connector.

In one embodiment, the third fluid channel of the fluid connector preferably extends through a central region of the fluid connector, and the first and second fluid channels of the fluid connector extend on opposite sides of the third fluid channel.

In one embodiment, the one or more third fluid exit openings are located adjacent the distal end of the mixing element, and the third fluid conduit of the mixing element extends to the distal end of the mixing element for being in fluid communication with the one or more third fluid exit openings.

In one embodiment, the one or more third fluid exit openings are located midway between the proximal and distal ends of the mixing element, and the third fluid conduit of the mixing element extends to the midway location of the mixing element for being in fluid communication with the one or more third fluid exit openings.

In one embodiment, the one or more third fluid exit openings are located adjacent the proximal end of the mixing element, and the third fluid inlet opening is in fluid communication with the one or more third fluid exit openings.

In one embodiment, a system and/or an applicator instrument may be designed so that the third fluid may be added into a first mixture of the first and second fluids at any location along the length of the spray tip assembly so as to control, adjust and/or modify the chemical reaction of the first and second reactive fluids.

In one embodiment, the inner surface of the outer wall of the spray tip housing has internal threads that are located adjacent the proximal end of the spray tip housing. In one embodiment, the distal end of the fluid connector has external threads that are configured to mesh with the internal threads of the spray tip housing for securing the distal end of the fluid connector with the proximal end of the spray tip housing.

In one embodiment, the first fluid channel of the fluid connector is aligned with a first lateral side of the mixing chamber, the second fluid channel of the fluid connector is aligned with a second lateral side of the mixing chamber, and the third fluid channel of the fluid connector is aligned with the third fluid inlet opening and the third fluid conduit of the mixing element.

In one embodiment, an applicator instrument for dispensing a biocompatible reactive formulation preferably includes a first chamber containing a first fluid having a first reactive component. In one embodiment, the first chamber is in fluid communication with the first fluid channel of the fluid connector.

In one embodiment, the applicator instrument preferably includes a second chamber containing a second fluid having a second reactive component that is reactive with the first reactive component. In one embodiment, the second chamber is in fluid communication with the second fluid channel of the fluid connector.

In one embodiment, the applicator instrument preferably includes a third chamber containing a third fluid. In one embodiment, the third chamber is in fluid communication with the third fluid channel of the fluid connector.

In one embodiment, a system for dispensing a biocompatible reactive formulation is configured to direct the first and second fluids in series through the respective first and second fluid channels of the fluid connector and into the mixing chamber for forming a first mixture.

In one embodiment, the system is configured to direct the third fluid in series through the third fluid channel of the fluid connector, into the third fluid inlet opening of the mixing element, through the third fluid conduit of the mixing element, and laterally through the one or more third fluid exit openings of the mixing element for entering into the mixing chamber for being added into the first mixture of the first and second fluids to form a final mixture.

In one embodiment, a dispensing cap is disposed within the elongated conduit of the spray tip housing and is secured to the distal end of the spray tip housing for opposing the distal end of the mixing element. In one embodiment, the dispensing cap preferably includes a dispensing opening that is in fluid communication with a distal end of the mixing chamber for expressing the final mixture of the first, second, and third fluids.

In one embodiment, a system for dispensing biocompatible reactive formulations desirably includes a first chamber containing a first fluid having a first reactive component, a second chamber containing a second fluid having a second reactive component that is reactive with the first reactive component, and a third chamber containing a third fluid.

In one embodiment, the system preferably includes a spray tip assembly that is configured for spraying a final mixture of the first, second and third fluids. In one embodiment, the spray tip assembly desirably includes a spray tip housing having a proximal end, a distal end, an outer wall that extends from the proximal end to the distal end of the spray tip housing, and an elongated conduit surrounded by the outer wall that extends from the proximal end to the distal end of the spray tip housing.

In one embodiment, a mixing element is disposed within the elongated conduit of the spray tip housing, and a mixing chamber is located between an outer surface of the mixing element and an inner surface of the outer wall of the spray tip housing.

In one embodiment, the mixing element desirably has a proximal end adjacent the proximal end of the spray tip housing and a distal end adjacent the distal end of the spray tip housing. In one embodiment, the mixing element has a third fluid inlet opening at the proximal end of the mixing element, and one or more third fluid exit openings formed in the outer surface of the mixing element that are in fluid communication with the third fluid inlet opening and that extend laterally to the outer surface of the mixing element for being in fluid communication with the mixing chamber.

In one embodiment, the spray tip assembly includes a fluid connector secured to the proximal end of the spray tip housing and opposing the proximal end of the mixing element. In one embodiment, the fluid connector preferably includes first and second fluid channels that are in fluid communication with the mixing chamber, and a third fluid channel that is in fluid communication with the third fluid inlet opening of the mixing element.

In one embodiment, the system desirably includes a pump assembly (e.g., syringe plungers) that is coupled with the first, second and third chambers for simultaneously forcing the first, second and third fluids to flow through the first, second and third fluid channels of the fluid connector and into the proximal end of the spray tip housing.

In one embodiment, the mixing element preferably includes a third fluid conduit extending distally from the third fluid inlet opening of the mixing element toward the distal end of the mixing element. In one embodiment, the third fluid conduit is in fluid communication with the one or more third fluid exit openings for directing the third fluid from the third fluid inlet opening to the one or more third fluid exit openings.

In one embodiment, a spray tip assembly may utilize a first mixing element having laterally extending third fluid exit openings that are located adjacent the distal end of the mixing element. In this embodiment, the first and second fluids are first mixed together within a mixing chamber at the proximal end of the first mixing element to form a first mixture, and, after the first mixture flows downstream through the mixing chamber toward the distal end of the mixing element, the third fluid is added to the first mixture, via the third fluid exit openings, adjacent the distal end of the first mixing element.

In one embodiment, a spray tip assembly may utilize a second mixing element having laterally extending third fluid exit openings that are located midway between the proximal end and the distal end of the second mixing element. In this embodiment, the first and second fluids are mixed together within the mixing chamber at the proximal end of the second mixing element to form a first mixture, and, as the first mixture flows downstream through the mixing chamber toward the distal end of the mixing element, the third fluid is added to the first mixture, via the third fluid exit openings, at a location that is midway between the proximal end and the distal end of the second mixing element.

In one embodiment, a spray tip assembly may utilize a third mixing element having laterally extending third fluid exit openings that are located adjacent the proximal end of the mixing element. In this embodiment, the first and second fluids are mixed together within the mixing chamber at the proximal end of the third mixing element to form a first mixture, and the third fluid is also added to the first mixture at the proximal end of the third mixing element, via the third fluid exit openings, to form a final mixture. The final mixture then travels the length of the mixing element for further mixing until it is dispensed via the dispensing opening of the dispensing cap.

In one embodiment, a system may include a kit having a first spray tip assembly that has the first mixing element, a second spray tip assembly that has the second mixing element, and a third spray tip assembly that has the third mixing element, whereby only one of the three spray tip assemblies is secured to the distal end of the applicator instrument at any one time. Thus, an operator may modify the characteristics of a biocompatible reactive formulation (i.e., by controlling how the first and second reactive components react with one another) that is dispensed from the applicator instrument by changing the spray tip assembly that is secured to the distal end of the applicator instrument. In one embodiment, a first spray tip assembly may be disconnected from a fluid connector and replaced by a second spray tip assembly that is secured to the fluid connector for changing how the three fluids are mixed together within the spray tip housing.

In other embodiments, the third fluid exit openings may be positioned at any location along the length of a mixing element to further modify and control how reactive components of a biocompatible reactive formulation react with one another. Thus, an infinite number of different types of reactions may be attained by modifying the structure of the mixing elements and/or where along the length of a spray tip assembly a third fluid is added into a first mixture of first and second reactive fluids.

In one embodiment, a method of making a biocompatible reactive formulation preferably includes using a mixing element for mixing a first fluid having a first reactive component and a second fluid having a second reactive component to form a first mixture, and, after forming the first mixture, adding a third fluid into the first mixture of the first and second fluids to form a final mixture. The method may include expressing the final mixture of the first mixture and the third fluid onto a surface (e.g., tissue).

In one embodiment, the first and second fluids are mixed together to form the first mixture adjacent a proximal end of the mixing element and the third fluid is added into the first mixture adjacent a distal end of the mixing element.

In one embodiment, the first and second fluids are mixed together to form the first mixture adjacent a proximal end of the mixing element and the third fluid is added into the first mixture at a location that is midway between the proximal and distal ends of the mixing element.

In one embodiment, the first and second fluids are mixed together to form the first mixture adjacent a proximal end of the mixing element and the third fluid is added into the first mixture adjacent the proximal end of the mixing element.

In one embodiment, the first fluid may include an electrophile, the second fluid may include a nucleophile at high pH, and the third fluid may include a pH modifying buffer or a diluent (e.g., $H_2O$; a buffer).

In a high concentration embodiment, both the electrophile and the nucleophile preferably have higher respective concentrations. In one embodiment, the initial mixture was 43 mg/mL 4 Arm PEG-Amine-10k, and 112.5 mg/mL 4 Arm PEG-SG-20k. After introduction of the third fluid, the concentration was 28.5 mg/mL PEG-Amine, and 75 mg/mL PEG-SG.

These and other preferred embodiments of the present patent application will be described in more detail herein.

BRIEF DESCRIPTION OF THE DRAWINGS

FIG. 21C is another perspective view of the proximal end of the fluid connector shown in FIGS. 21A and 21B.

FIG. 21D is a proximal end view of the fluid connector shown in FIGS. 21A-21C.

FIG. 24D is a cross-sectional view of the dispensing cap shown in FIGS. 24A-24C.

DETAILED DESCRIPTION OF PREFERRED EMBODIMENTS

Figure 1A:
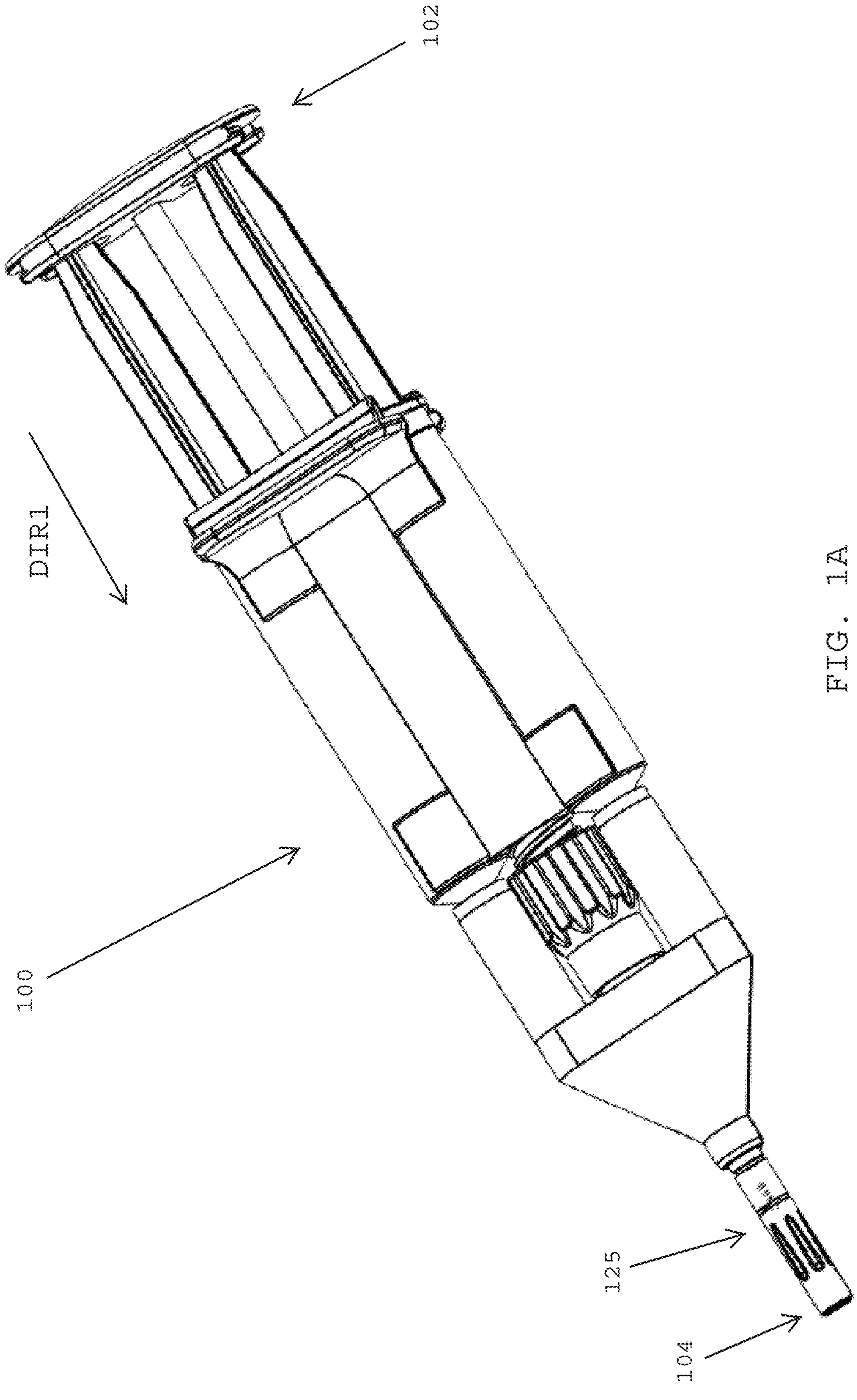
FIG. 1A is a perspective view of an applicator instrument adapted for dispensing biocompatible reactive formulations, in accordance with one embodiment of the present patent application.
Figure 1B:
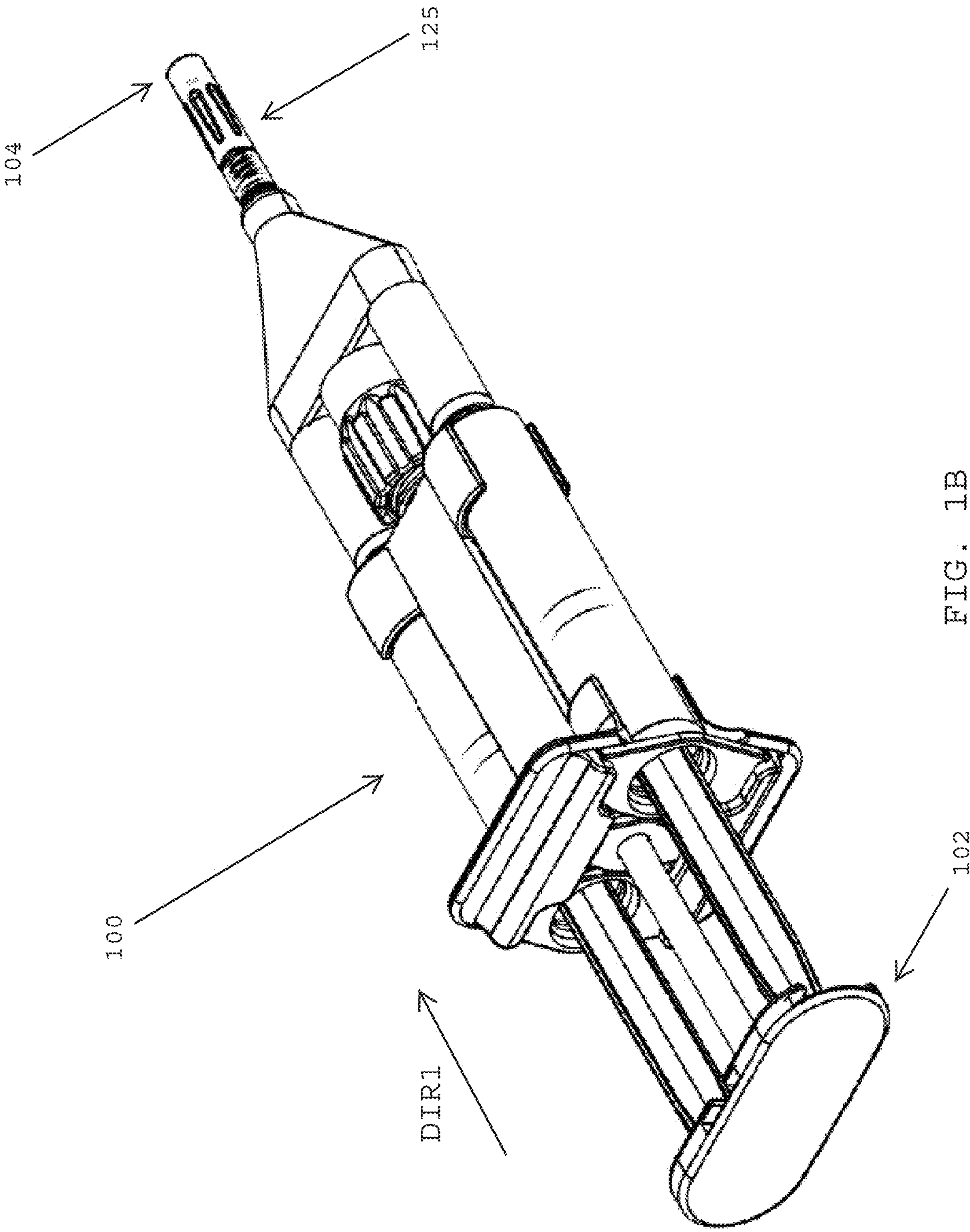
FIG. 1B is a perspective view of a proximal end of the applicator instrument shown in FIG. 1A.

Referring to FIGS. 1A and 1B, in one embodiment, an applicator instrument 100 for mixing and expressing a composition, such as a biocompatible reactive formulation (e.g., a tissue adhesive; a tissue sealant), preferably has a proximal end 102 and a distal end 104. In one embodiment, the applicator instrument 100 is desirably configured for mixing together two or more fluid components to form a final mixture of a composition, such as a biocompatible reactive formulation. In one embodiment, the final mixture of the biocompatible reactive formulation is preferably expressed (e.g., sprayed) via a spray tip assembly 125, which is located at the distal end 104 of the applicator instrument 100.

Figure 2:
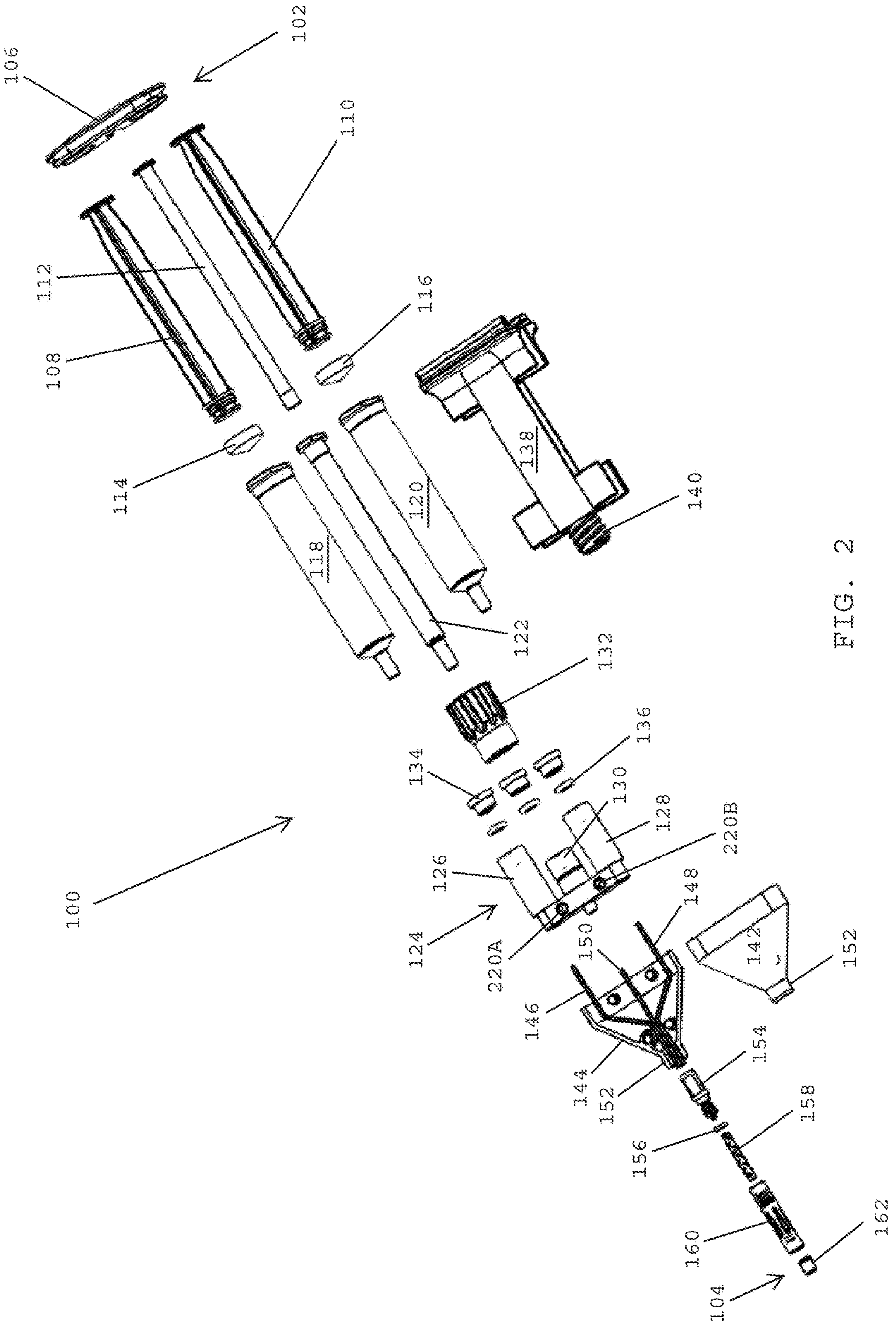
FIG. 2 is an exploded view of the applicator instrument shown in FIGS. 1A and 1B.
Figure 3:
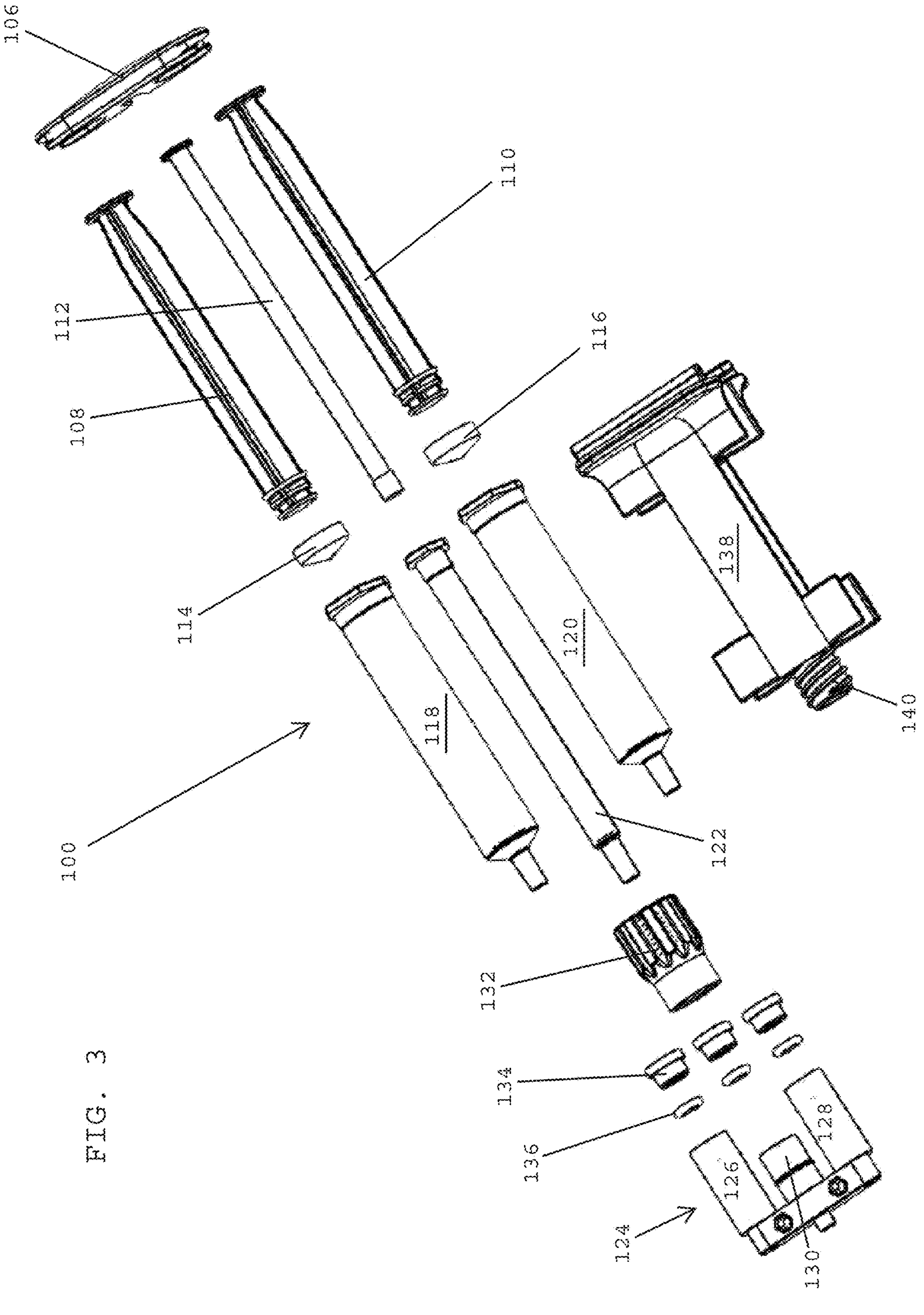
FIG. 3 is a magnified view of proximal components of the applicator instrument shown in FIG. 2.

Referring to FIGS. 2 and 3, in one embodiment, the applicator instrument 100 preferably includes a plunger head 106 located at the proximal end 102 thereof, which is adapted to be assembled with proximal ends of a first syringe plunger 108, a second syringe plunger 110, and a third syringe plunger 112, respectively. In one embodiment, the first and second syringe plungers 108, 110 may have larger cross-sectional diameters, respectively, than the cross-sectional diameter of the third syringe plunger 112.

In one embodiment, a first piston 114 may be secured to the distal end of the first syringe plunger 108, and a second piston 116 may be secured to the distal end of the second syringe plunger 110.

In one embodiment, the applicator instrument 100 preferably includes a first syringe barrel 118 that is adapted to receive a first fluid having a first reactive component (e.g., an electrophile) of a biocompatible reactive formulation. In one embodiment, the first syringe barrel 118 is adapted to receive the first piston 114 and the first syringe plunger 108, which may be used for forcing the first fluid from the distal end of the first syringe barrel 118.

In one embodiment, the applicator instrument 100 preferably includes a second syringe barrel 120 that is adapted to receive a second fluid having a second reactive component (e.g., a nucleophile) of a biocompatible reactive formulation, whereby the first and second fluids may be mixed together to form a first mixture. In one embodiment, the second syringe barrel 120 is adapted to receive the second piston 116 and the second syringe plunger 110, which may be used for forcing the second fluid from the distal end of the second syringe barrel 120. In one embodiment, the first and second fluids have reactive components that are adapted to chemically react with one another to form a biocompatible reactive formulation that is applied to tissue or biomaterial.

In one embodiment, the applicator instrument 100 desirably includes a third syringe barrel 122 that is adapted to receive the third syringe plunger 112. In one embodiment, the third syringe barrel 122 is adapted to contain a third fluid (e.g., a pH modifying buffer; a diluent such as $H_2O$ or a buffer) that may be added into the first mixture of the first and second fluids. In one embodiment, the third plunger 112 may be used for forcing the third fluid from the distal end of the third syringe barrel, whereupon it may be added into and/or mixed with the first mixture of the first and second fluids to form a final mixture that is expressed from the distal end 104 of the applicator instrument 100.

In one embodiment, the first and second syringe barrels 118, 120 may be larger than the third syringe barrel 122. In one embodiment, the first and second syringe barrels have respective inner diameters that are the same. In one embodiment, the first and second syringe barrels 118, 120 may have respective cross-sectional diameters that are larger than the cross-sectional diameter of the third syringe barrel 122. In one embodiment, the respective first and second syringe barrels 118, 120 may be configured to hold larger volumes of fluid than the volume of fluid that may be held within the third syringe barrel 122. In one embodiment, the first and second syringe barrels may be designated as large syringe barrels and the third syringe barrel may be designated as a small syringe barrel.

In one embodiment, the first fluid within the first syringe barrel may include an electrophile (e.g., PEG-NHS). In one embodiment, the second fluid within the second syringe barrel may include a nucleophile at high pH (e.g., PEG-$NH_2$). In one embodiment, the third fluid within the third syringe barrel may include a pH modifying buffer.

In one embodiment, the first fluid within the first syringe barrel may include an electrophile at high concentration (e.g., PEG-NHS), the second fluid within the second syringe barrel may include a nucleophile at high concentration (e.g., PEG-$NH_2$), and the third fluid within the third syringe barrel may include a diluent (e.g., $H_2O$ or buffer).

In one embodiment, the first and second fluids may include additions of polyelectrolytes such as alginate, heparin, hyaluronic acid, and chitosan. In one embodiment, the third fluid may include polyvalent ions, such as Calcium.

In one embodiment, the first fluid comprises Fibrinogen, the second fluid comprises Thrombin, and the third fluid comprises a diluent, such as $H_2O$.

In one embodiment, the applicator instrument 100 preferably includes a fluid manifold 124 that is located downstream from the distal ends of the first, second and third syringe barrels 118, 120, 122. In one embodiment, the fluid manifold 124 preferably includes a first connector 126 adapted to receive a distal end of the first syringe barrel 118, a second connector 128 adapted to receive a distal end of the second syringe barrel 120, and a third connector 130 adapted to receive a distal end of the third syringe barrel 122.

In one embodiment, the first connector 126 of the fluid manifold 124 is preferably in fluid communication with the first syringe barrel 118. In one embodiment, a first component of a biocompatible reactive formulation (e.g., a first fluid containing a first reactive component) that is preloaded into the first syringe barrel 118 may be forced to flow into the first connector 126 of the fluid manifold 124, such as by depressing the first syringe plunger 108.

In one embodiment, the second connector 128 of the fluid manifold 124 is preferably in fluid communication with the second syringe barrel 120. In one embodiment, a second component of a biocompatible reactive formulation (e.g., a second fluid containing a second reactive component that reacts with the first reactive component) that is pre-loaded into the second syringe barrel 120 may be forced to flow into the second connector 128 of the fluid manifold 124, such as by depressing the second syringe plunger 110.

In one embodiment, the third connector 130 of the fluid manifold 124 is preferably in fluid communication with the third syringe barrel 122. In one embodiment, a third component of a biocompatible reactive formulation that is preloaded into the third syringe barrel 122 (e.g., a pH modifying buffer; a diluent such as $H_2O$ or a buffer) may be forced to flow into the third connector 130 of the fluid manifold 124, such as by depressing the third syringe plunger 110.

In one embodiment, proximal ends of the first, second, and third syringe plungers 108, 110, and 112 may be coupled together so that they may be depressed simultaneously. In one embodiment, the proximal ends of the three syringe plungers 108, 110, and 112 may be connected with the plunger head 106, which may be forced to move in the distal direction DIR1 (FIGS. 1A and 1B) for simultaneously depressing the syringe plungers 108, 110, and 112.

In one embodiment, the applicator instrument 100 preferably includes a connecting nut 132 that may be utilized for securing a distal end of the third syringe barrel 122 with the third connector 130 of the fluid manifold 124.

In one embodiment, O-ring retainers 134 and O-rings 136 are preferably utilized for forming fluid-tight connections between the distal ends of the three syringe barrels 118, 120, 122 and the respective connectors 126, 128, 130 of the fluid manifold 124.

In one embodiment, the applicator instrument 100 preferably includes a syringe barrel support frame 138 that is adapted to receive and hold the first, second and third syringe barrels 118, 120, and 122. The syringe barrel support frame 138 desirably holds the syringe barrels 118, 120, 122 together for stabilizing the syringe barrels and enhancing the structural integrity of the applicator instrument 100.

In one embodiment, the syringe barrel support frame 138 preferably has a distal end with a distal projection 140 having external threads, which are adapted to mesh with internal threads (not shown) of the connecting nut 132 for securing the distal end of the syringe barrel support frame 138 to the connecting nut 132. Thus, in one embodiment, the connecting nut 132 may be utilized for securing both the distal projection 140 of the syringe barrel support frame 138 and the distal end of the third syringe barrel 122 to the second connector 130 of the fluid manifold 124.

Figure 4:
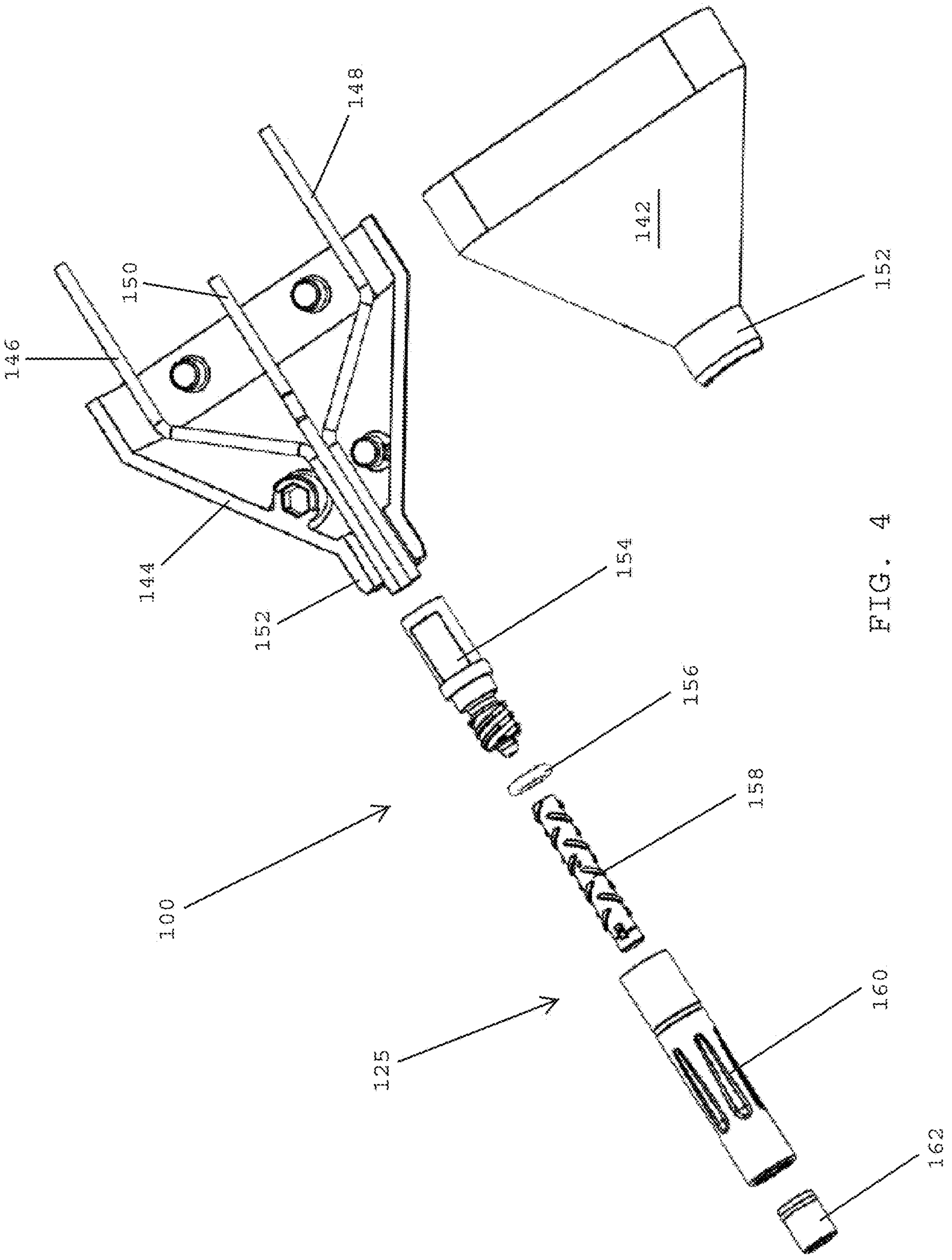
FIG. 4 is a magnified view of distal components of the applicator instrument shown in FIG. 2.

Referring to FIGS. 2 and 4, in one embodiment the distal end of the applicator instrument 100 preferably includes an upper fluid tube enclosure 142 and a lower fluid tube enclosure 144 that are adapted to be assembled with one another over the distal end of the fluid manifold 124. In one embodiment, the upper and lower fluid tube enclosures 142, 144 of the applicator instrument 100 preferably contain a first fluid tube 146 that is adapted to be in fluid communication with the distal end of the first syringe barrel 118, a second fluid tube 148 that is adapted to be in fluid communication with the distal end of the second syringe barrel 120, and a third fluid tube 150 that is adapted to be in fluid communication with the distal end of the third syringe barrel 122. In one embodiment, the distal ends of the respective fluid tubes 146, 148, and 150 preferably pass through a fluid tube channel 152 that is located at the distal ends of the respective upper and lower fluid tube enclosures 142, 144. As will be described in more detail herein, in one embodiment, the fluid tube channel 152 preferably directs the fluid tubes 146, 148, and 150 into a proximal end of a fluid connector 154.

In one embodiment, the distal end of the applicator instrument 100 preferably includes a spray tip assembly 125 that is used for spraying a final mixture of a biocompatible reactive formulation. In one embodiment, the spray tip assembly 125 desirably includes an O-ring 156 that is adapted to be assembled with the fluid connector 154, a mixing element 158 that is adapted to be disposed inside a spray tip housing 160, and a dispensing cap 162 that is adapted to be secured to the distal end of the spray tip housing 160. In one embodiment, the O-ring 156 preferably forms a fluid-tight seal between the fluid connector 154 and an inner surface of the spray tip housing 160. In one embodiment, an assembly of the fluid connector 154, the O-ring 156, the mixing element 158, the spray tip housing 160, and the dispensing cap 162 may be referred to as the spray tip assembly 125.

In one embodiment, the first and second fluid components supplied via the respective first and second fluid tubes 146 and 148 may be mixed together within a mixing chamber located inside the spray tip housing 160 to form a first mixture. In one embodiment, the third fluid component supplied via the third fluid tube 150 may be added into the first mixture to form a final mixture. In one embodiment, the third component may be added into the first mixture at a selected location between the proximal end and the distal end of the spray tip housing 160.

In one embodiment, the first and second fluids may be mixed together adjacent the proximal end of the mixing element 158 to form a first mixture and the third fluid may be added to the first mixture adjacent the proximal end of the mixing element 158 to form a final mixture that is expressed from the distal end of the spray tip housing 160.

In one embodiment, the first and second fluids may be mixed together adjacent the proximal end of the mixing element 158 to form a first mixture and the third fluid may be added to the first mixture at a midsection of the mixing element 158 to form a final mixture that is expressed from the distal end of the spray tip housing 160.

In one embodiment, the first and second fluids may be mixed together adjacent the proximal end of the mixing element 158 to form a first mixture and the third fluid may be added to the first mixture adjacent the distal end of the mixing element 158 to form a final mixture that is expressed from the distal end of the spray tip housing 160.

In one embodiment, the final mixture of the three components may be expressed (e.g., sprayed) via a dispensing opening in the dispensing cap 162.

Figure 5A:
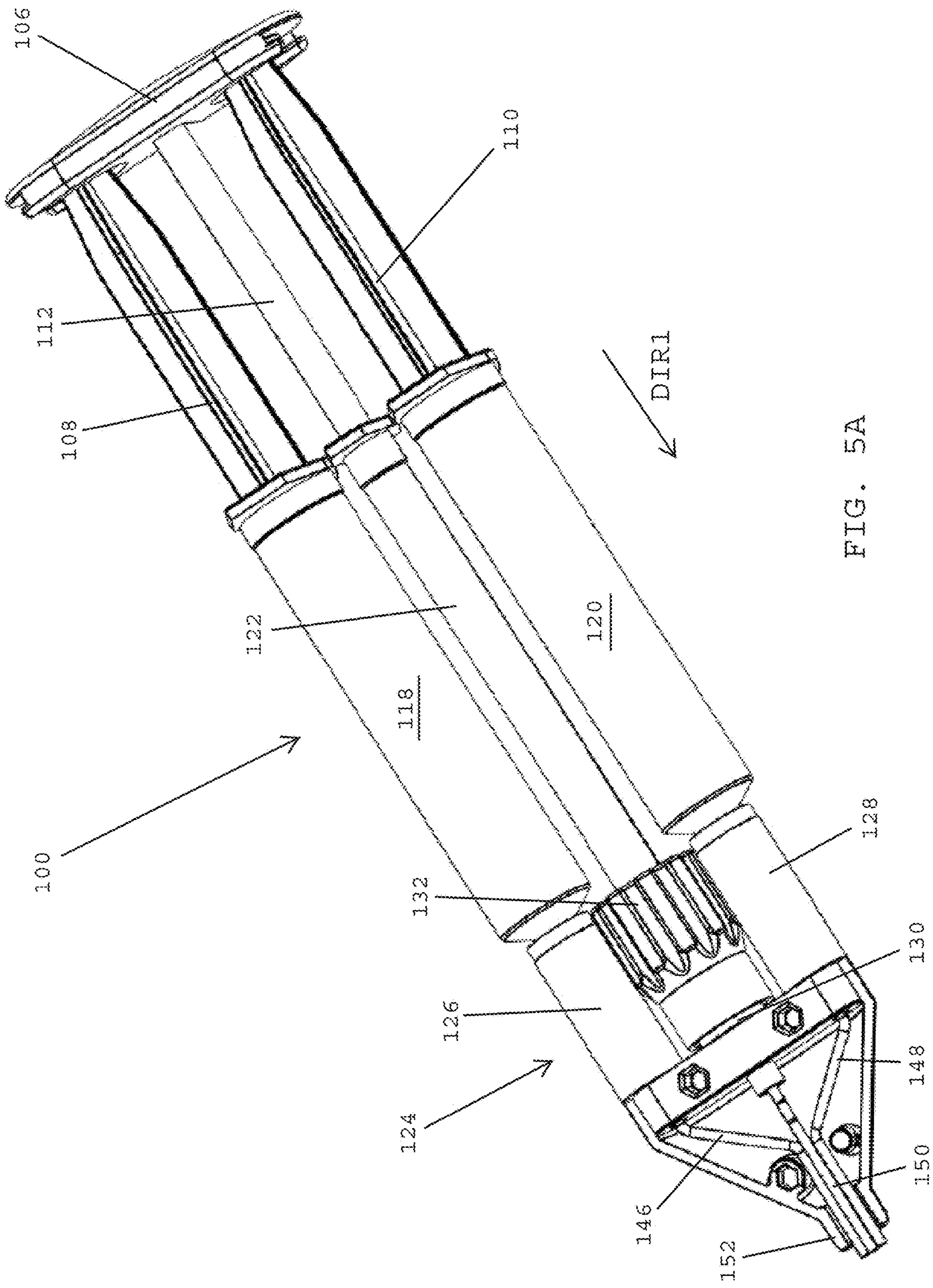
FIG. 5A shows a subassembly of the proximal end of an applicator instrument shown in FIGS. 1A and 1B, in accordance with one embodiment of the present patent application.
Figure 5B:
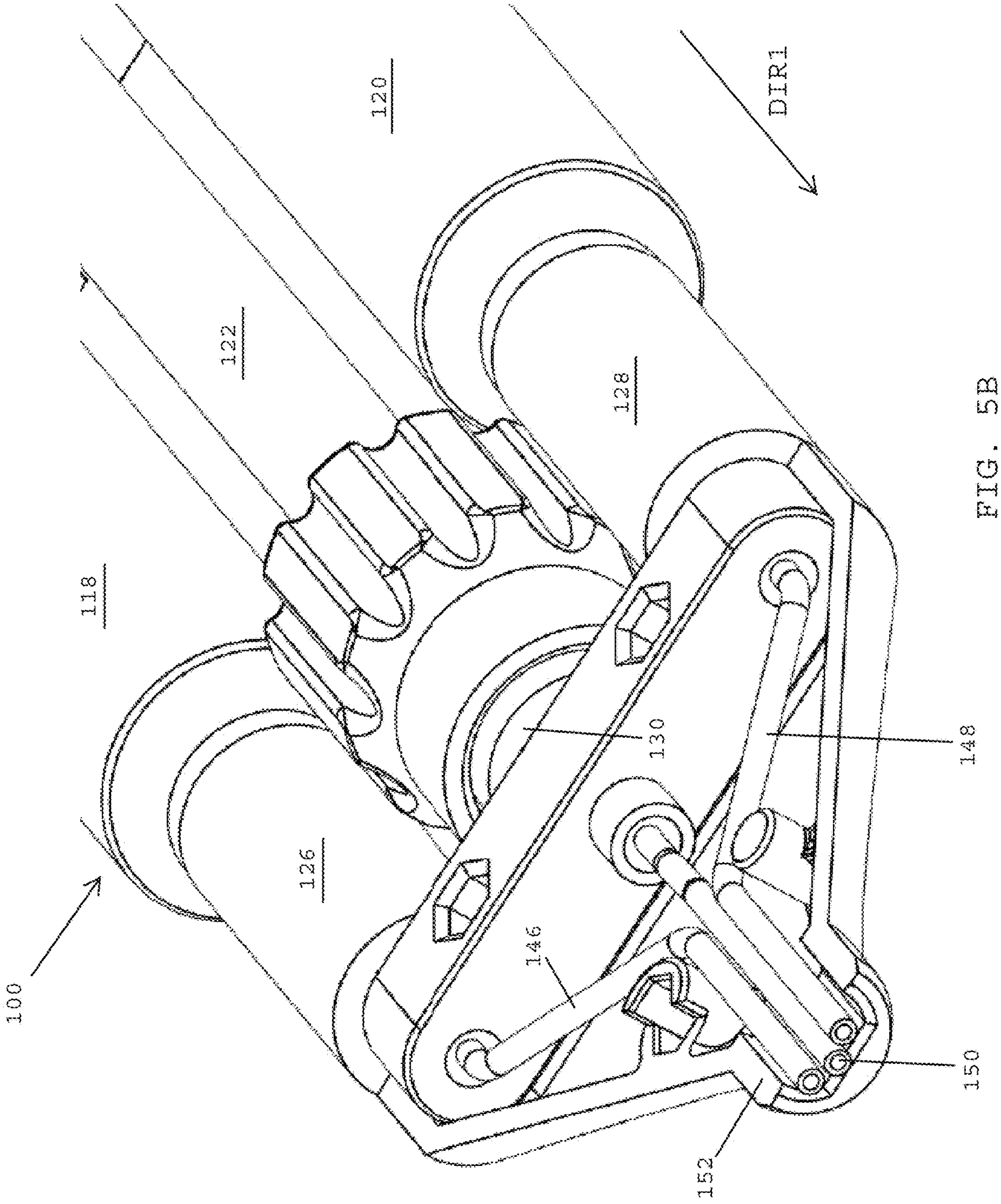
FIG. 5B shows a perspective view of a distal end of the subassembly of the applicator instrument shown in FIG. 5A.

Referring to FIGS. 5A and 5B, in one embodiment, the distal ends of the respective first, second and third syringe barrels 118, 120, and 122 may be assembled with the fluid manifold 124 by inserting the distal end of the first syringe barrel 118 into the first connector 126, the distal end of the second syringe barrel 120 into the second connector 128, and the distal end of the third syringe barrel 122 into the third connector 130. In one embodiment, the connecting nut 132 may be utilized for interconnecting the distal end of the third syringe barrel 122 with the third connector 130 of the fluid manifold 124. Although not shown in FIGS. 5A and 5B, the connecting nut 132 may also be used for securing the externally threaded distal projection 140 at the distal end of the syringe barrel support frame 138 (FIG. 3) with the third connector 130 of the fluid manifold 124.

In one embodiment, the applicator instrument 100 desirably includes the first fluid tube 146 that is in fluid communication with the distal end of the first syringe barrel 118, the second fluid tube 148 that is in fluid communication with the distal end of the second syringe barrel 120, and the third fluid tube 150 is in fluid communication with the distal end of the third syringe barrel 122. The distal ends of the three fluid tubes 146, 148, and 150 preferably pass through the fluid tube channel 152 of the upper and lower fluid tube enclosures 142, 144 (FIG. 4).

In one embodiment, as the plunger head 106 (FIG. 5A) is depressed toward the distal end of the applicator instrument 100 in the distal direction designated DIR1, the respective syringe plungers 108, 110, and 112 move simultaneously with one another to preferably force the three fluids that are within the three syringe barrels 118, 120, and 122 into the respective first, second and third fluid tubes 146, 148, and 150 for being mixed together within the spray tip assembly 125 (FIGS. 1A and 1B) that is located at the distal end of the applicator instrument 100.

Figure 6A:
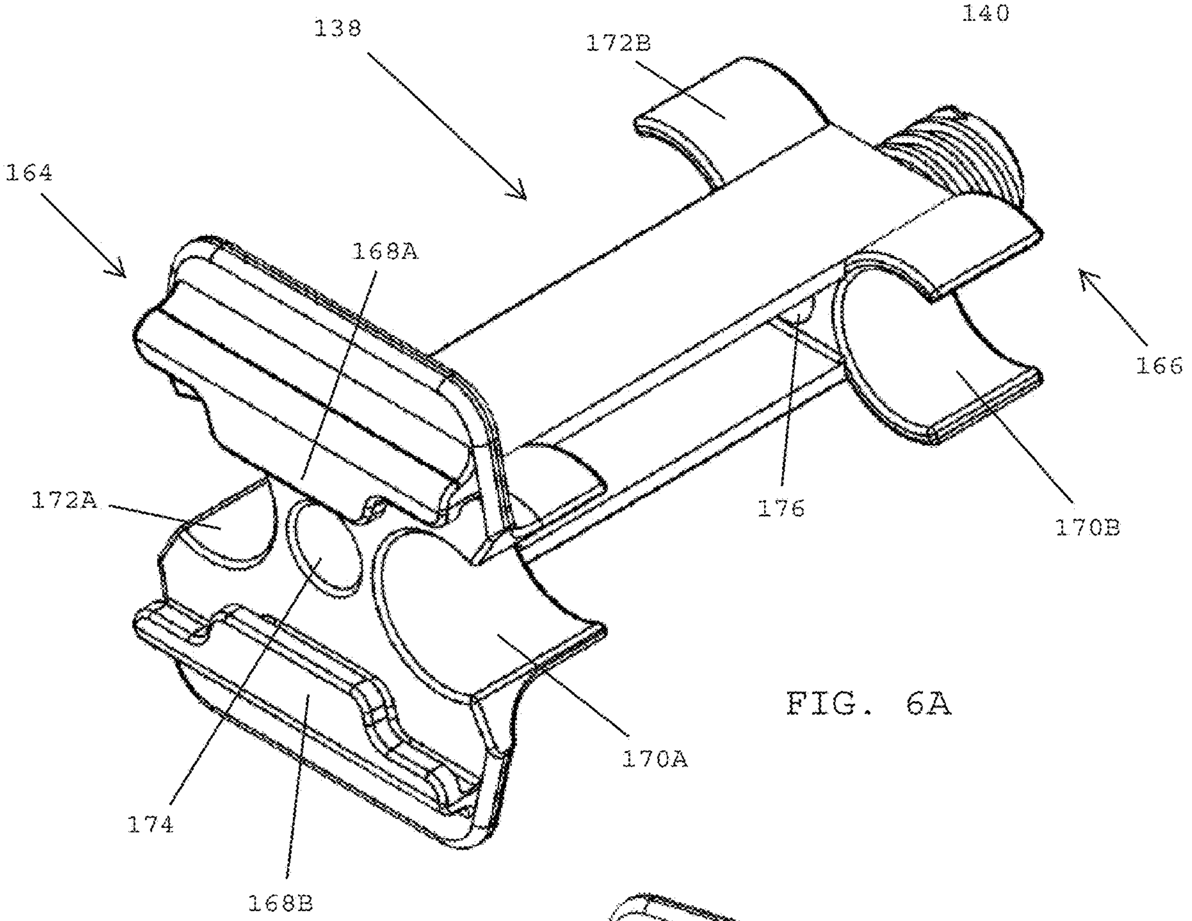
FIG. 6A is a perspective view of a proximal end of a syringe barrel support frame of an applicator instrument, in accordance with one embodiment of the present patent application.
Figure 6B:
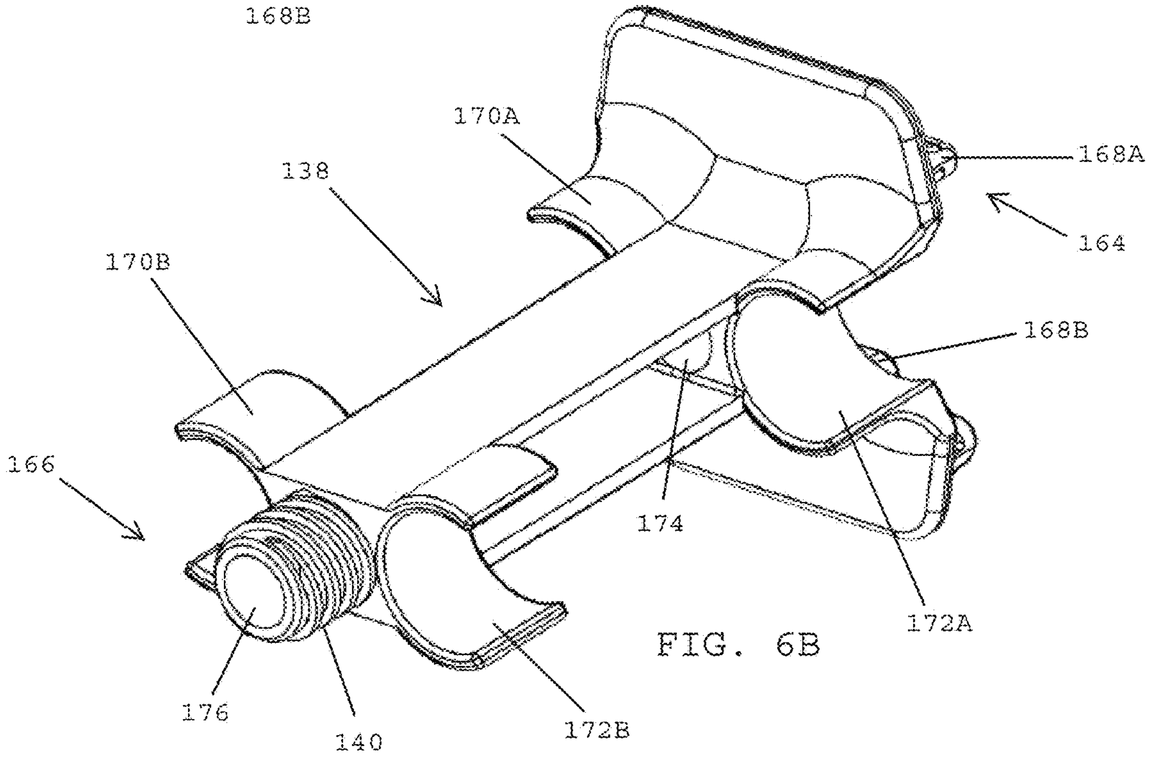
FIG. 6B is a perspective view of a distal end of the syringe barrel support frame shown in FIG. 6A.

Referring to FIGS. 6A and 6B, in one embodiment, the applicator instrument 100 (FIG. 1A) preferably includes the syringe barrel support frame 138 having a proximal end 164 and a distal end 166 with the externally threaded projection 140 extending from the distal end 166 of the syringe barrel support frame.

In one embodiment, the proximal end 164 of the syringe barrel support frame 138 preferably includes syringe barrel securing flanges 168A, 168B that oppose one another and that are adapted to engage flanges located at the proximal ends of the respective first, second, and third syringe barrels 118, 120, 122 (FIG. 3) for securing the proximal ends of the syringe barrels to the syringe barrel support frame 138.

In one embodiment, the syringe barrel support frame 138 preferably includes a first set of C-shaped flanges 170A, 170B that are adapted to engage an outer wall of the first syringe barrel 118 (FIG. 2) for securing the first syringe barrel to the syringe barrel support frame 138. In one embodiment, the syringe barrel support frame 138 preferably includes a second set of C-shaped flanges 172A, 172B that are adapted to engage an outer wall of the second syringe barrel 120 (FIG. 2) for securing the second syringe barrel to the syringe barrel support frame. In one embodiment, the syringe barrel support frame 138 preferably includes a central opening 174 located at the proximal end thereof that is aligned with a central opening 176 formed in the externally threaded projection 140 located at the distal end 166 of the syringe barrel support frame. In one embodiment, the third syringe barrel 122 (FIG. 2) may be passed through the central opening 174 at the proximal end and the central opening 176 of the externally threaded projection 140 for securing the third syringe barrel with the syringe barrel support frame 138.

Figure 7A:
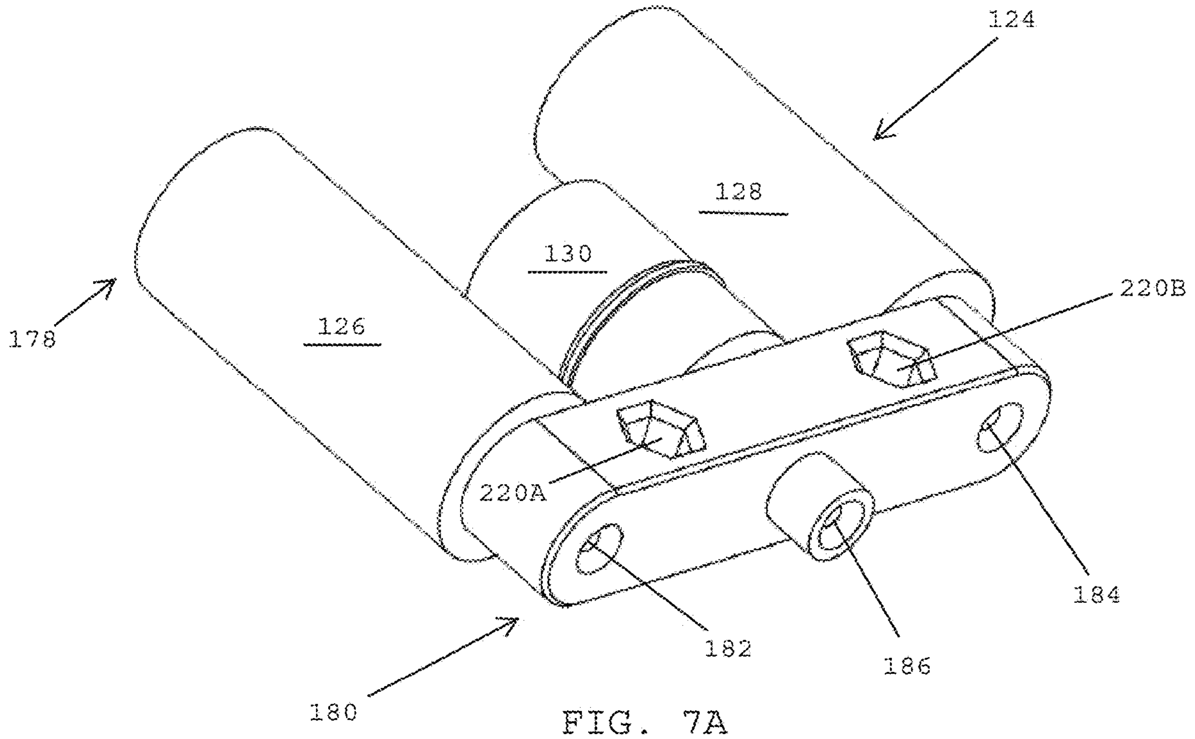
FIG. 7A is a perspective view of a distal end of a fluid distribution manifold of an applicator instrument, in accordance with one embodiment of the present patent application.
Figure 7B:
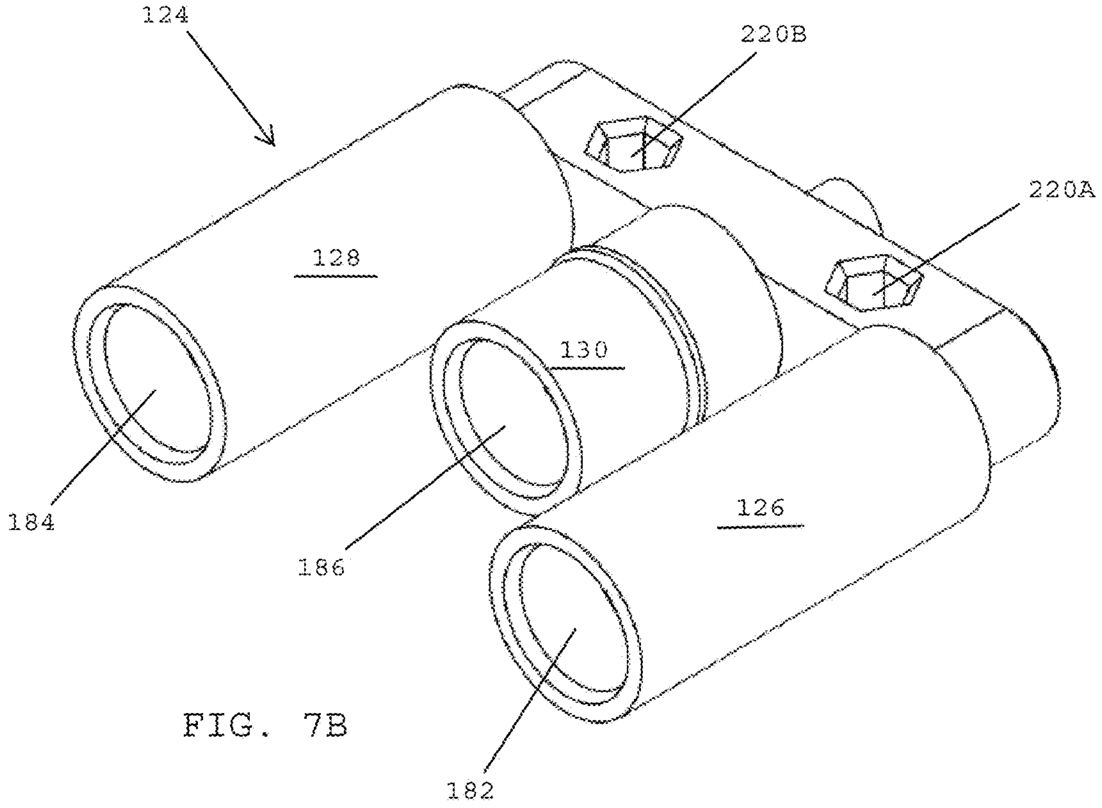
FIG. 7B is a perspective view of a proximal end of the fluid distribution manifold shown in FIG. 7A.

Referring to FIGS. 7A and 7B, in one embodiment, the fluid manifold 124 (FIG. 2) preferably has a proximal end 178 and a distal end 180. In one embodiment, the fluid manifold 124 preferably includes the first connector 126 having an opening 182 that is adapted to receive a distal end of the first syringe barrel 118 (FIG. 2). In one embodiment, the fluid manifold 124 also desirably includes the second connector 128 having a central opening 184 that is adapted to receive a distal end of the second syringe barrel 120 (FIG. 2). In one embodiment, the fluid manifold 124 also preferably includes the third connector 130 having a central opening 186 that is adapted to receive a distal end of the third syringe barrel 122 (FIG. 2).

In one embodiment, the central openings 182, 184, 186 of the respective first, second and third connectors 126, 128, and 130 preferably extend to the distal end 180 of the fluid manifold 124. In one embodiment, proximal ends of the first, second and third fluid tubes 146, 148, 150 (FIG. 2) preferably pass through the respective openings 182, 184, and 186 at the distal end 180 of the fluid manifold 124 for being in fluid communication with the distal ends of the respective first, second, and third syringe barrels 118, 120, and 122 (FIG. 2). The distal ends of the fluid tubes 146, 148, and 150 are preferably in fluid communication with the spray tip assembly 125 (FIG. 1A).

Figure 8A:
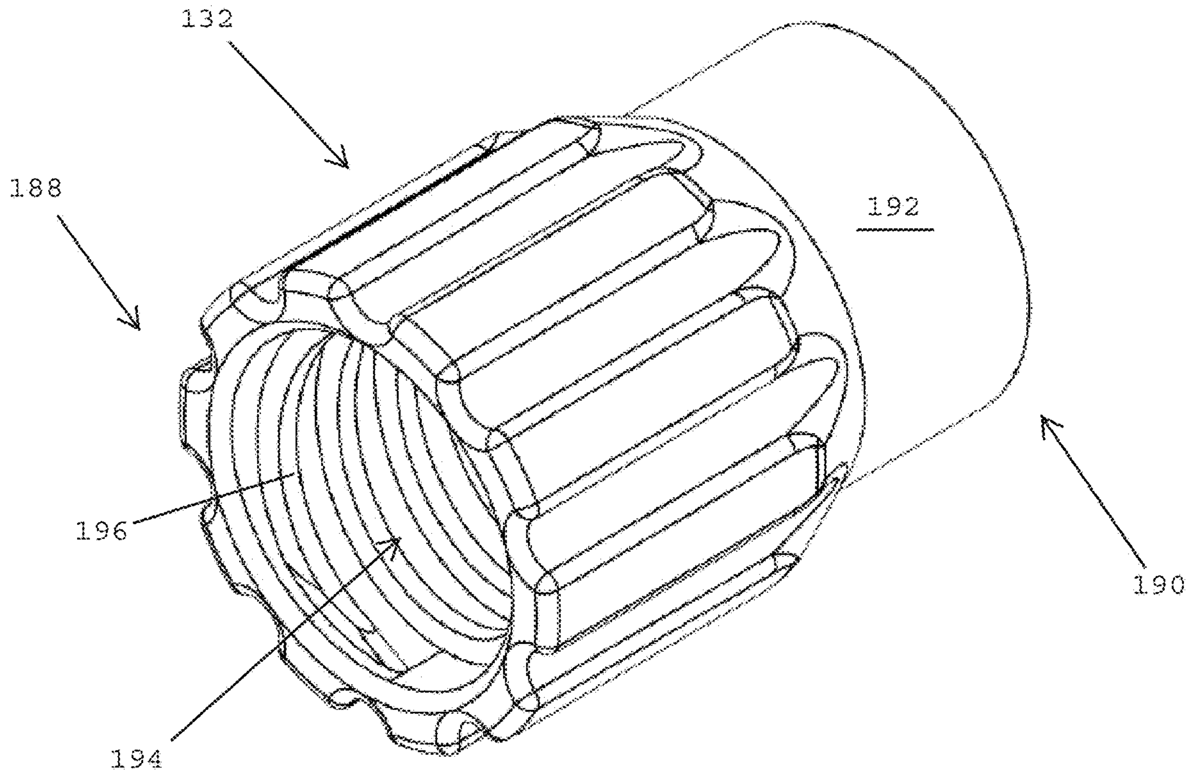
FIG. 8A is a perspective view of a proximal end of a connecting nut of an applicator instrument, in accordance with one embodiment of the present patent application.
Figure 8B:
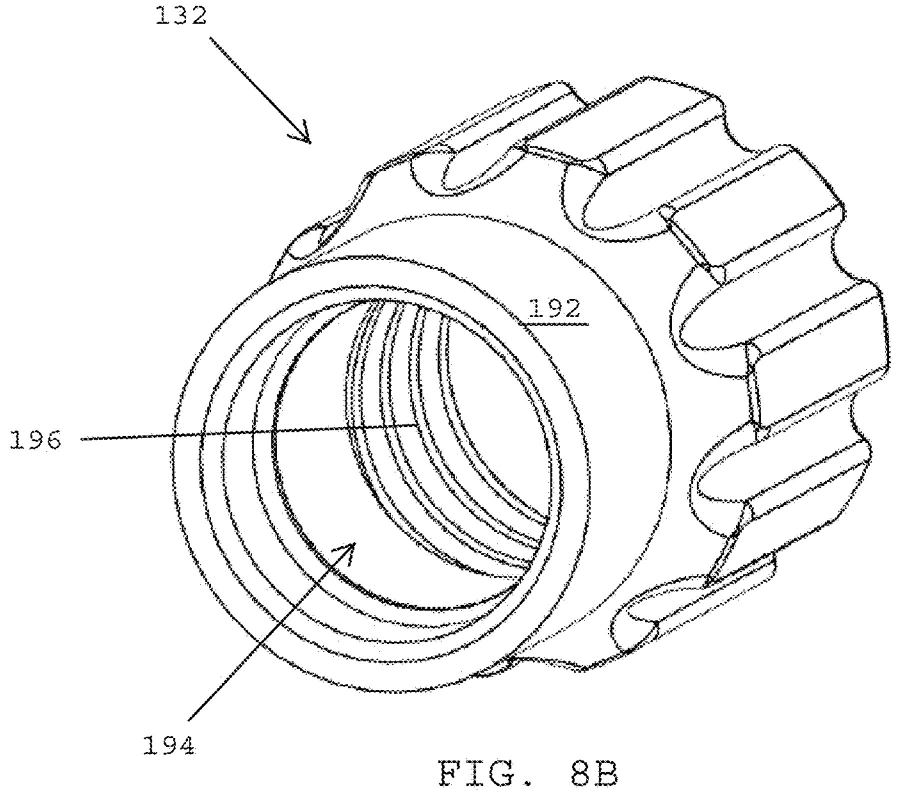
FIG. 8B is a perspective view of a distal end of the connecting nut shown in FIG. 8A.

Referring to FIGS. 8A and 8B, in one embodiment, the applicator instrument 100 (FIG. 1A) preferably includes the connecting nut 132 having a proximal end 188 and a distal end 190 with a tube-shaped connector 192 that is adapted to be secured with the third connector 130 of the fluid manifold 124 (FIG. 2). In one embodiment, the connecting nut 132 preferably has a central conduit 194 that extends from the proximal end 188 to the distal end 190 thereof. In one embodiment, the connecting nut 132 preferably includes internal threads 196 adjacent the proximal end 188 thereof that are adapted to mesh with the external threads of the externally threaded projection 140 at the distal end of the syringe barrel support frame 138 for securing the distal end of the syringe barrel support frame 138 to the fluid manifold 124 (FIG. 3).

Figure 9A:
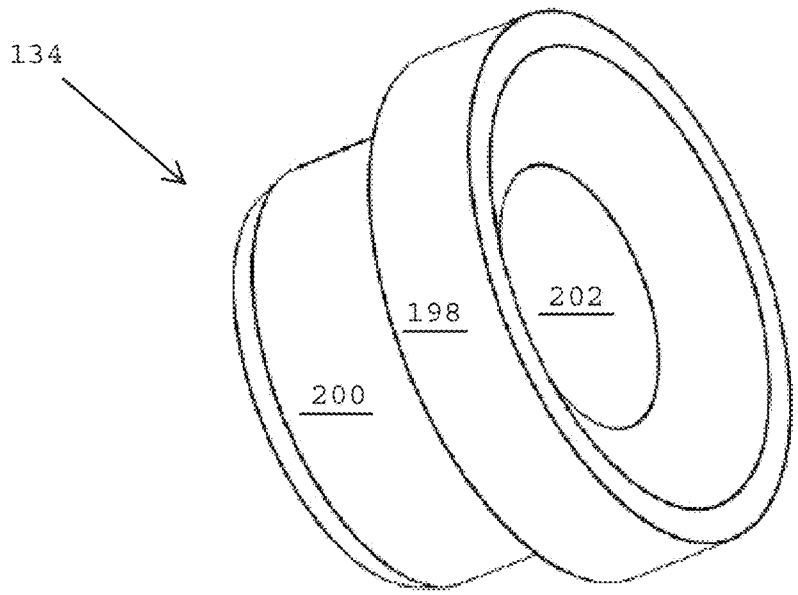
FIG. 9A is a perspective view of a proximal end of an O-ring retainer of an applicator instrument, in accordance with one embodiment of the present patent application.
Figure 9B:
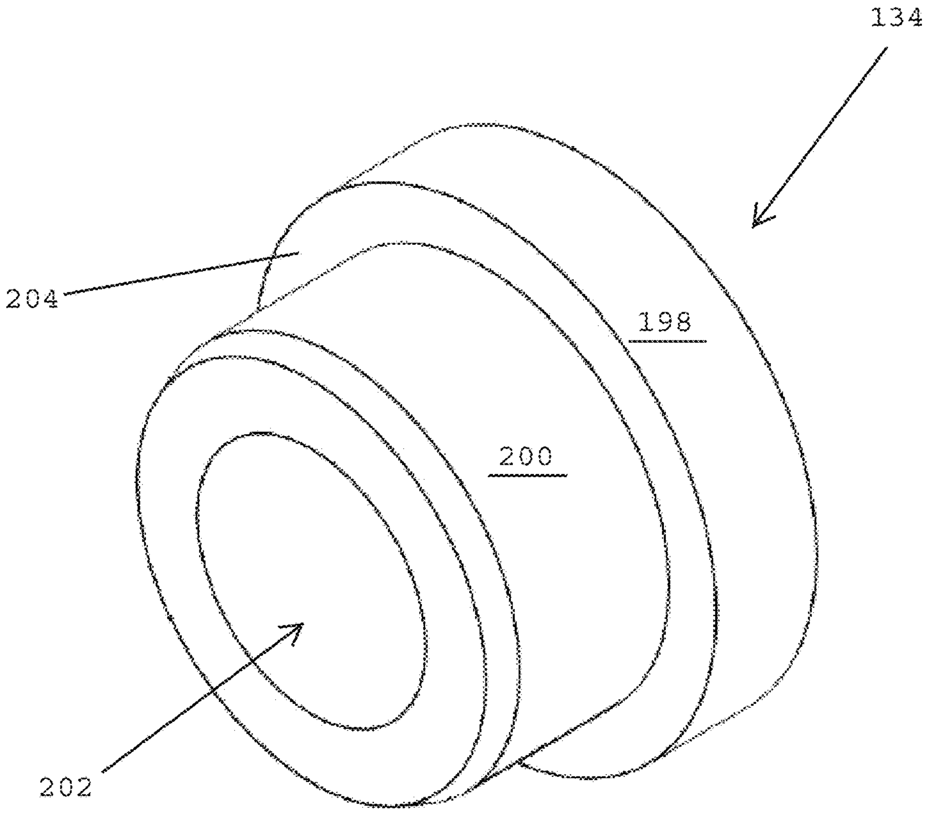
FIG. 9B is a perspective view of a distal end of the O-ring retainer shown in FIG. 9A.

Referring to FIGS. 3, 9A, and 9B, in one embodiment, the applicator instrument 100 (FIG. 1A) preferably includes one or more O-ring retainers 134 having a larger diameter section 198 and a smaller diameter section 200 with a central opening 202 passing through both the larger and smaller diameter sections 198, 200. In one embodiment, the size difference between the larger diameter section 198 and the smaller diameter section 200 preferably defines an abutting surface 204 that is adapted to abut against proximal faces of the respective first, second and third connectors 126, 128, 130 of the fluid manifold 124 (FIG. 2). In one embodiment, an O-ring 136 (FIG. 3) may be assembled over the outer surface of the smaller diameter section 200 for facilitating the formation of a water-tight seal between the abutting surface 204 of the O-ring retainer 134 and the proximal face of an opposing connector of the fluid manifold. Referring to FIG. 3, in one embodiment, the distal ends of the respective syringe barrels 118, 120, and 122 preferably pass through the central opening 202 of the O-ring retainer 134 associated therewith.

Figure 10A:
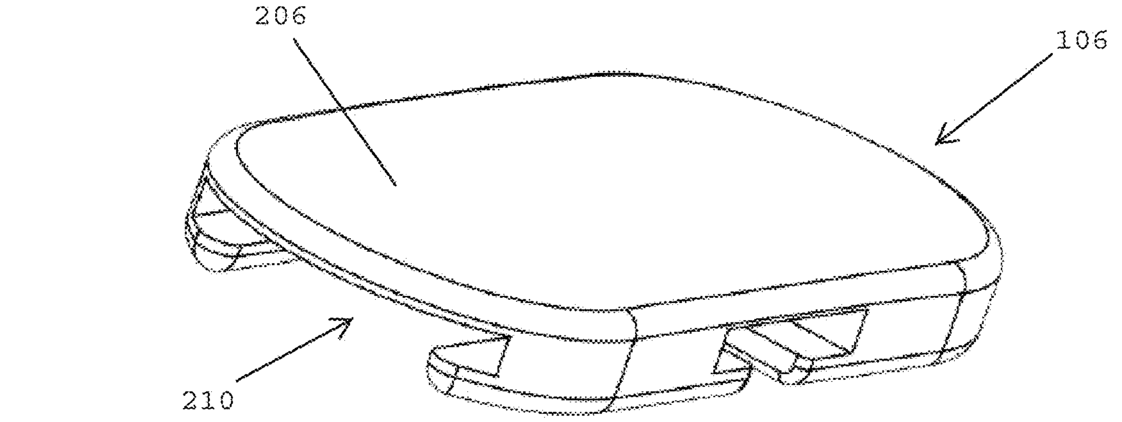
FIG. 10A is a perspective view of a topside of a plunger head of an applicator instrument, in accordance with one embodiment of the present patent application.
Figure 10B:
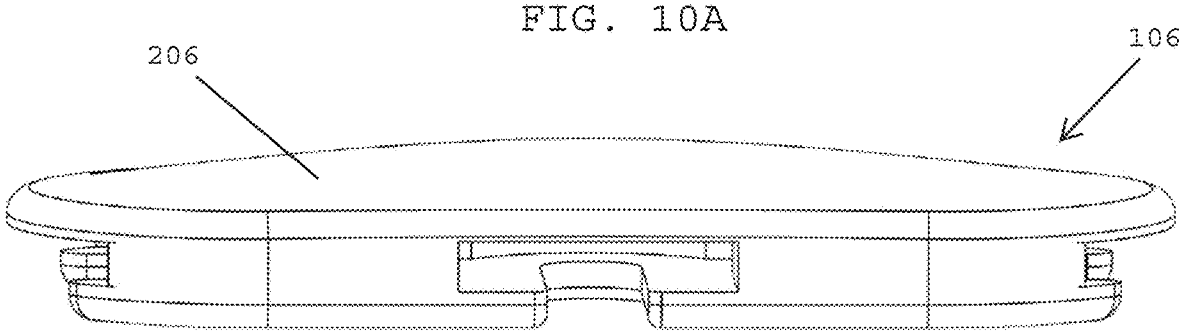
FIG. 10B is a side elevation view of the plunger head shown in FIG. 10A.
Figure 10C:
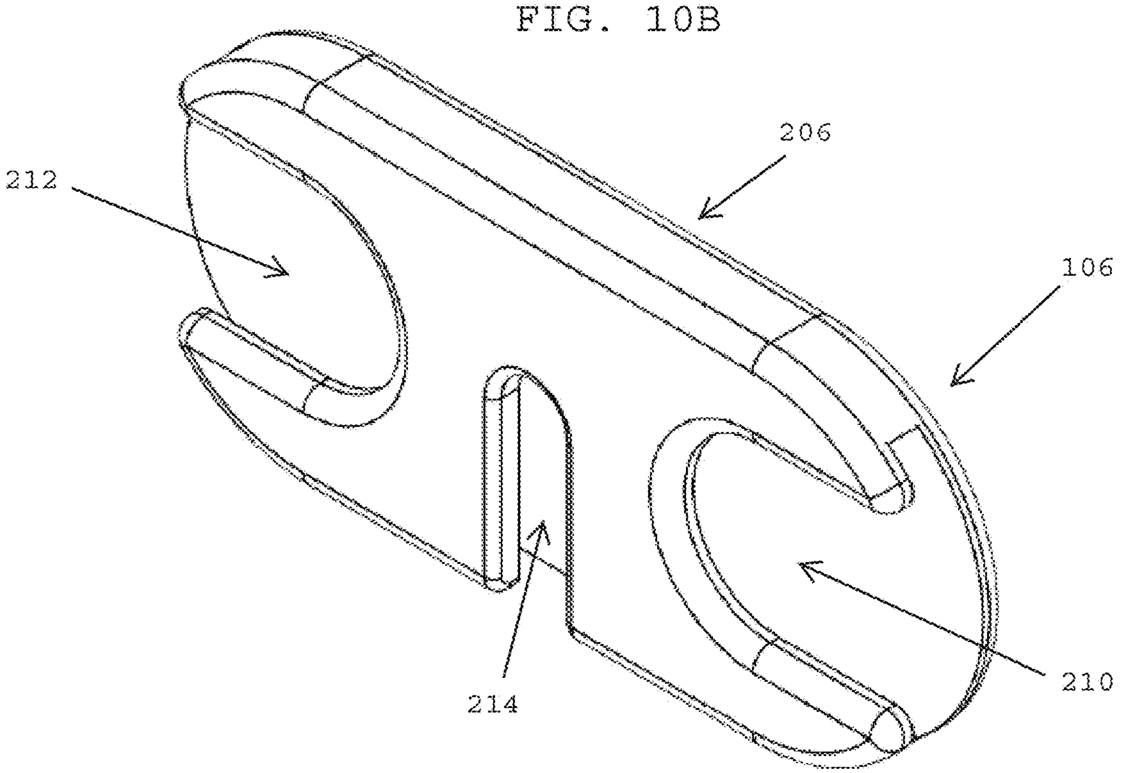
FIG. 10C is a perspective view of an underside of the plunger head shown in FIGS. 10A and 10B.
Figure 11:
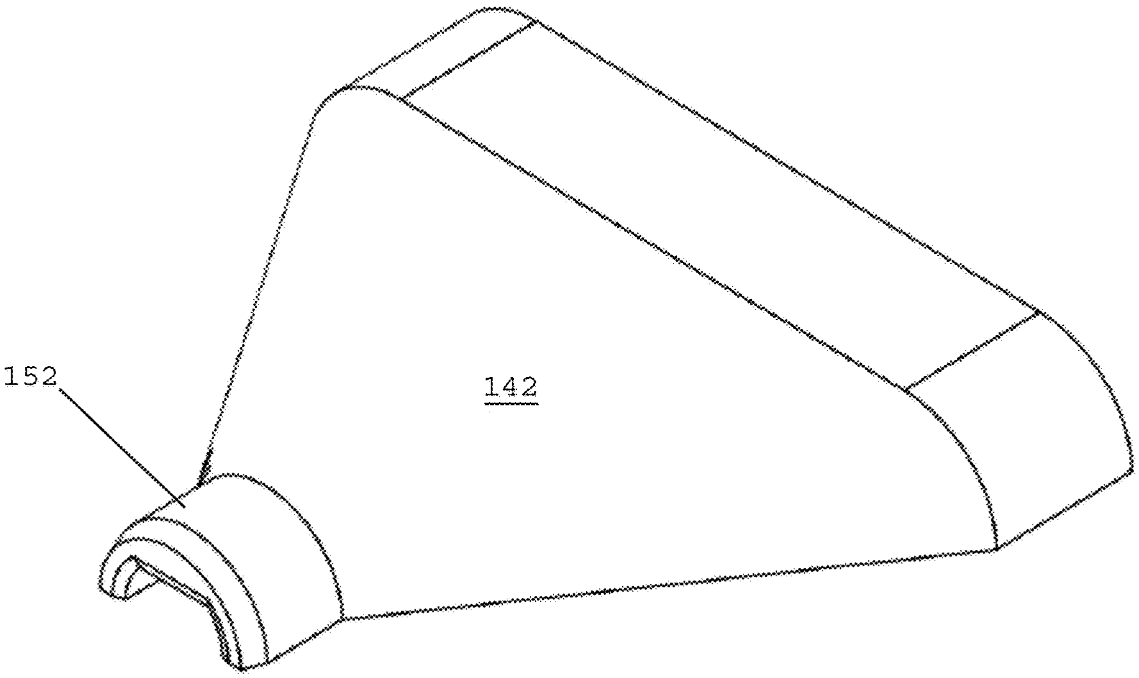
FIG. 11 is a perspective view of an upper fluid tube enclosure of an applicator instrument, in accordance with one embodiment of the present patent application.

Referring to FIGS. 10A-10C, in one embodiment, the applicator instrument 100 (FIG. 1A) preferably includes the plunger head 106 having a proximal face 206 that faces toward the proximal end of the applicator instrument and a distal face 208 that faces toward the distal end of the applicator instrument. In one embodiment, the plunger head 106 preferably includes a first syringe plunger attachment slot 210 that is adapted to receive a thumb flange located at the proximal end of the first plunger 108 (FIG. 3) for securing the proximal end of the first syringe plunger with the plunger head 106. In one embodiment, the plunger head 106 desirably includes a second syringe plunger attachment slot 212 that is adapted to receive a thumb flange at the proximal end of the second plunger 110 (FIG. 3) for securing the proximal end of the second syringe plunger 110 with the plunger head 106. In one embodiment, the plunger head 106 desirably includes a third syringe plunger attachment slot 214 that is preferably adapted to receive a thumb flange at the proximal end of the third syringe plunger 112 (FIG. 3) for securing the proximal end of the third syringe plunger with the plunger head 106.

In one embodiment, after the proximal ends of the respective syringe plungers 108, 110, 112 (FIG. 3) have been secured to the plunger head 106, the plungers may be moved simultaneously with one another as the plunger head 106 is depressed in the distal direction DIR1 toward the distal end 104 of the applicator instrument 100 (FIG. 1A).

Referring to FIGS. 2, 4, 11 and 12, in one embodiment, the applicator instrument 100 preferably includes the upper fluid tube enclosure 142 and the lower fluid tube enclosure 144 that are assembled together for being secured to the distal end of the fluid manifold 124 (FIG. 2). In one embodiment, the lower fluid tube enclosure 144 desirably has an inner face 216 that includes proximally located projections 218A, 218B that are adapted to be inserted into female openings 220A, 220B (FIG. 7A) formed in the fluid manifold 124. The upper fluid tube enclosure may have similar projections. The projections may be used for assembling the proximal ends of the respective upper and lower fluid tube enclosures 142, 144 with the distal end of the fluid manifold 124 (FIG. 7A).

In one embodiment, the distal ends of the respective upper and lower fluid tube enclosures 142, 144 preferably includes the fluid tube channel 152 that is adapted to guide the distal ends of the first, second and third fluid tubes 146, 148, 150 (FIG. 2) into the proximal end of the spray tip assembly 125, which is located at the distal end 104 of the applicator instrument 100 (FIG. 1A).

Figure 12:
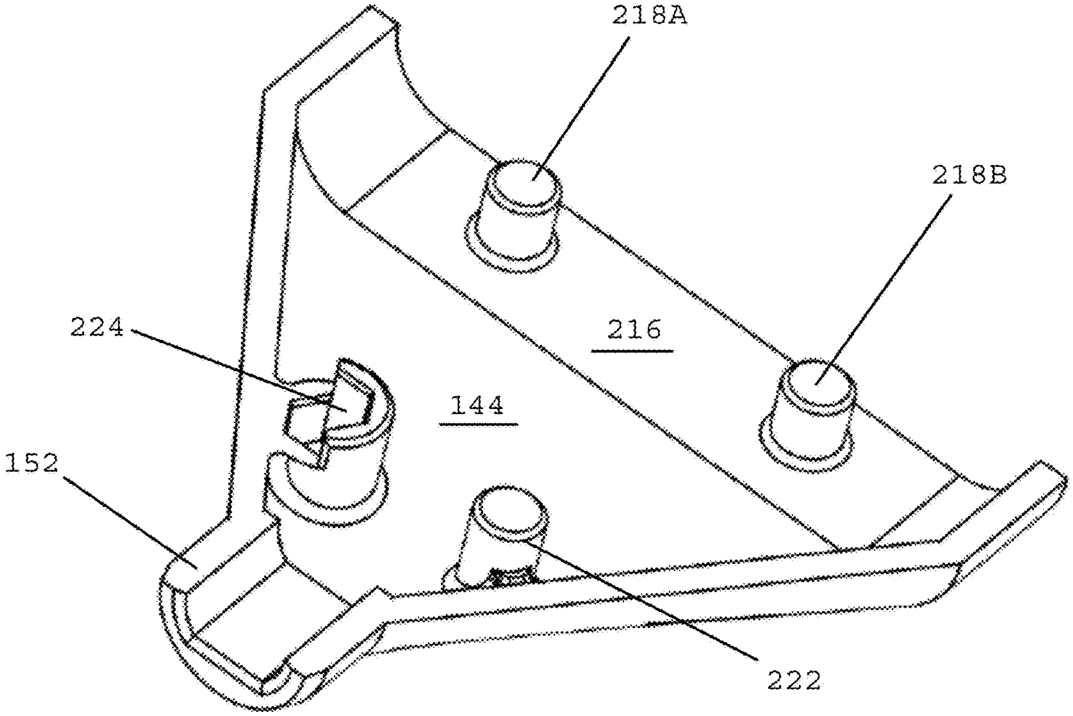
FIG. 12 is a perspective view of a lower fluid tube enclosure of an applicator instrument, in accordance with one embodiment of the present patent application.

Referring to FIG. 12, in one embodiment, the inner face 216 of the lower fluid tube enclosure 144 preferably includes at least one male post 222 and at least one female opening 224 that are adapted to engage structural features provided on an opposing inner face of the upper fluid tube enclosure 142 (FIG. 11) for forming a snap-fit connection between the upper and lower fluid tube enclosures 142, 144. For example, a male post on the upper fluid tube enclosure may be inserted into a female opening on the lower fluid tube enclosure, and a male post on the lower fluid tube enclosure may be inserted into a female opening on the upper fluid tube enclosure.

Figure 13:
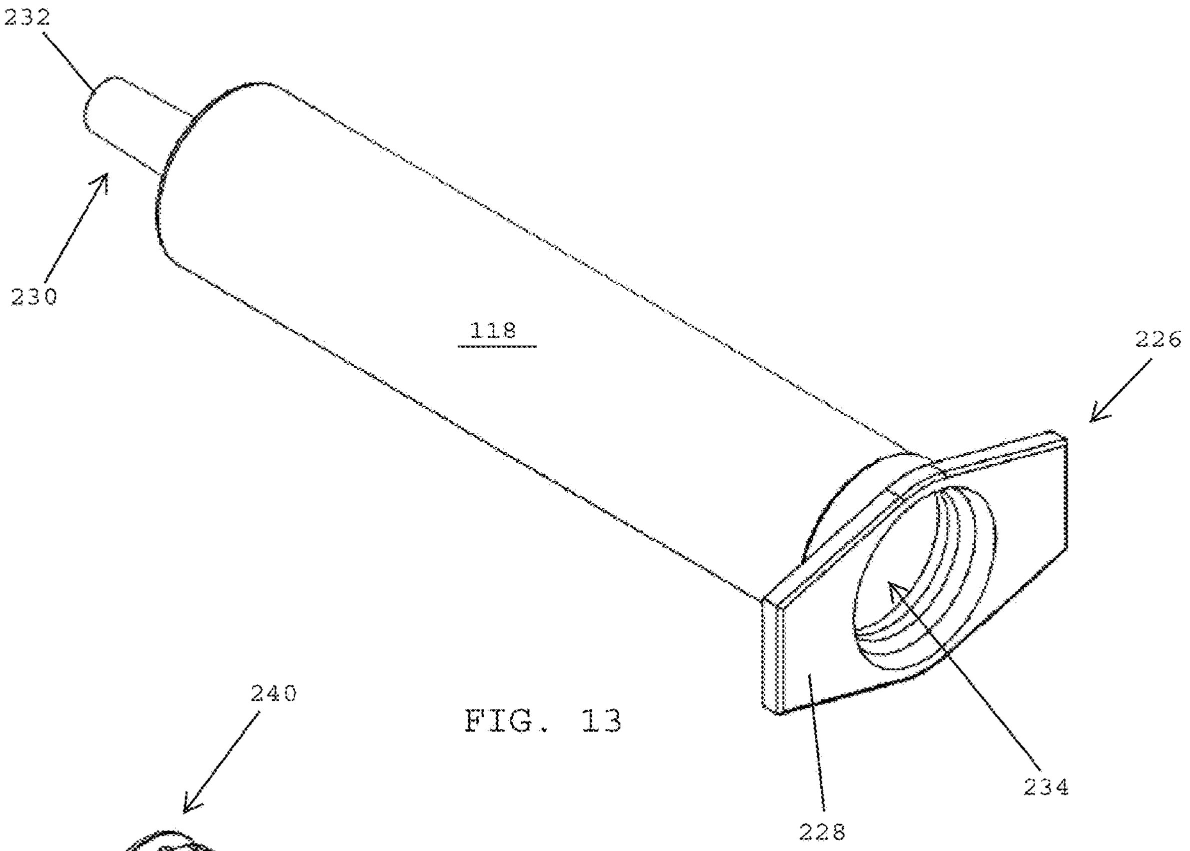
FIG. 13 is a perspective view of a first syringe barrel of an applicator instrument, in accordance with one embodiment of the present patent application.
Figure 14:
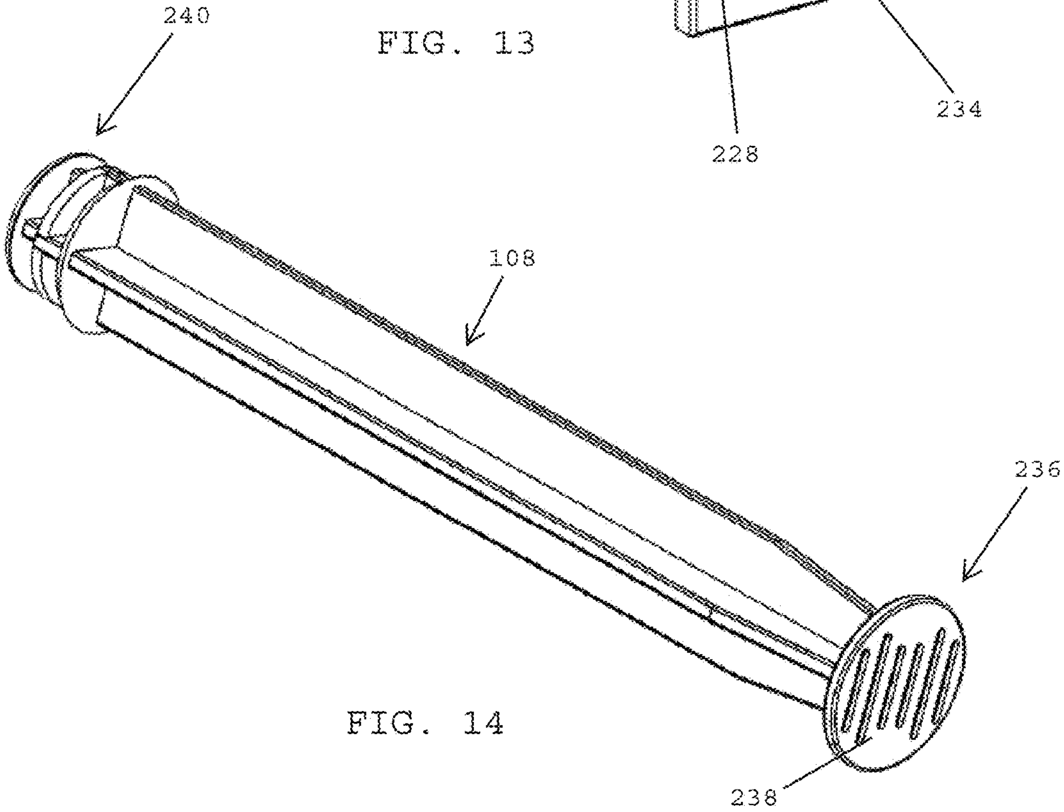
FIG. 14 is a perspective view of a first syringe plunger that is assembled with the first syringe barrel of FIG. 13, in accordance with one embodiment of the present patent application.

Referring to FIG. 13, in one embodiment, the first syringe barrel 118 (FIG. 3) preferably has a proximal end 226 including a laterally extending flange 228 and a distal end 230 having a dispensing opening 232. Referring to FIGS. 13 and 14, in one embodiment, the proximal end 226 of the first syringe barrel 118 desirable includes a first syringe barrel opening 234 that is adapted to receive the first syringe plunger 108 (FIG. 3).

In one embodiment, the first syringe plunger 108 preferably includes a proximal end 236 having a thumb engaging flange 238 and a distal end 240 that is adapted to be coupled with a first piston 114 (FIG. 3). In one embodiment, the distal end 240 including the first piston 114 (FIG. 2) is adapted to be inserted into the first syringe barrel opening 224 for being depressed toward the distal end 230 of the first syringe barrel 118.

In one embodiment, the applicator instrument preferably includes the second syringe barrel 120 and the second syringe plunger 110 (FIG. 3), which may have a structure, size, shape, and configuration that is similar to that shown and described above in FIGS. 13 and 14 for the first syringe barrel 118 and the first plunger 108. In one embodiment, the first and second syringe barrels may have different sizes for holding different volumes of fluid.

Figure 15:
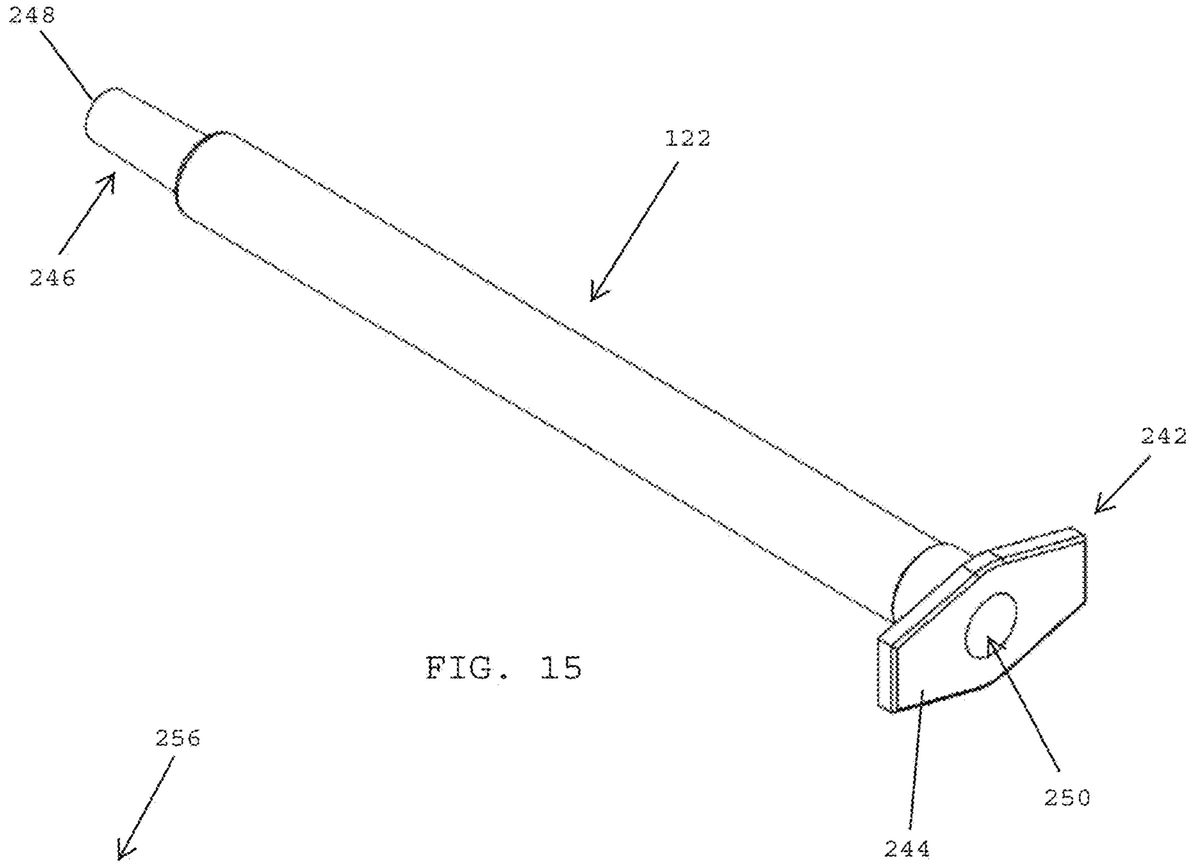
FIG. 15 is a perspective view of a third syringe barrel of an applicator instrument, in accordance with one embodiment of the present patent application.
Figure 16:
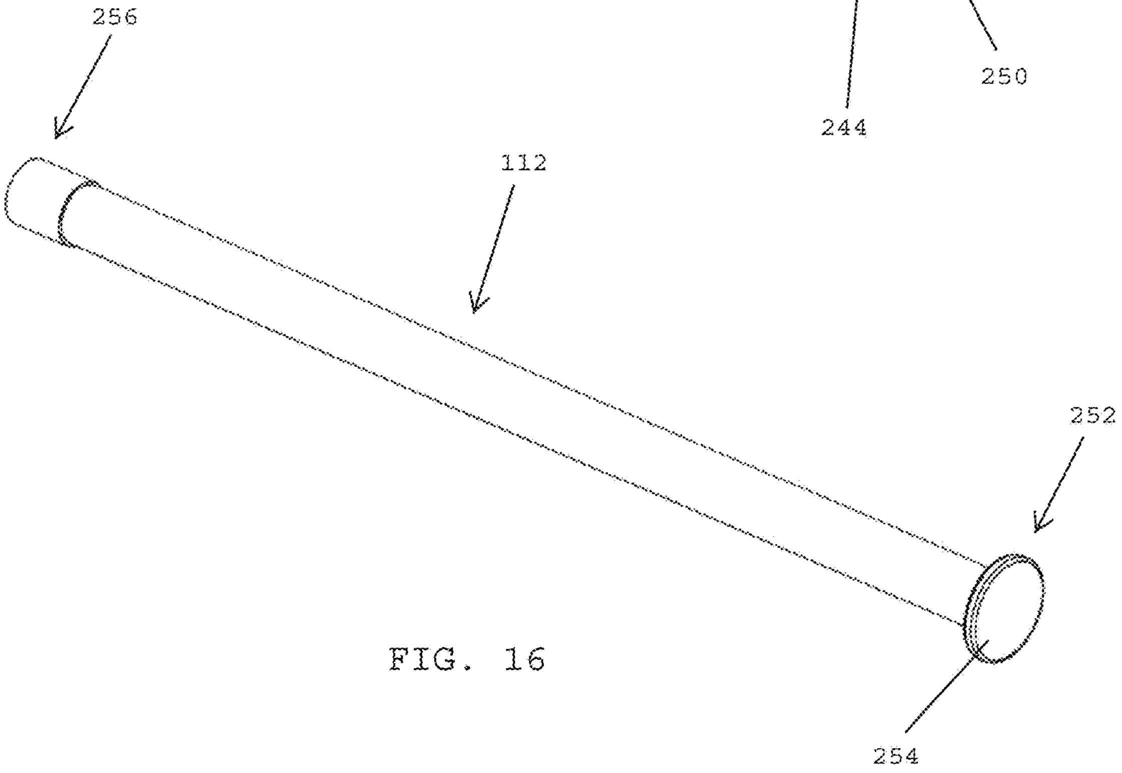
FIG. 16 is a perspective of a proximal end of a third syringe plunger that is assembled with the third syringe barrel of FIG. 15.

Referring to FIGS. 3, 15, and 16, in one embodiment, the applicator instrument 100 preferably includes the third syringe located in the center of the device, which preferably includes the third syringe barrel 122 and third syringe plunger 112. In one embodiment, the third syringe barrel 122 preferably has a proximal end 242 having a laterally extending flange 244 and a distal end 246 having a dispensing opening 248 adapted to dispense a third fluid component disposed within the third syringe barrel 122. In one embodiment, the third syringe barrel 122 preferably includes a third barrel opening 250 that preferably extends from the proximal end 242 to the fluid dispensing opening 248 located at the distal end 246 of the third syringe barrel 122.

In one embodiment, the third syringe plunger 112 preferably includes a proximal end 252 having a thumb engaging flange 254 that may be engaged for depressing the third syringe plunger 112 toward the distal end 246 of the third syringe barrel 122. In one embodiment, the third syringe plunger 112 preferably includes a distal end 256 that is adapted to be inserted into the central opening 250 of the third syringe barrel 122. In one embodiment, the third syringe plunger 112 may be depressed in a distal direction DIR1 (FIG. 1A) toward the distal end 246 of the third syringe barrel 122 for dispensing a third fluid component that is pre-loaded into the third syringe barrel 122 from the dispensing opening 248 located at the distal end 246 of the third syringe barrel 122.

Figure 17:
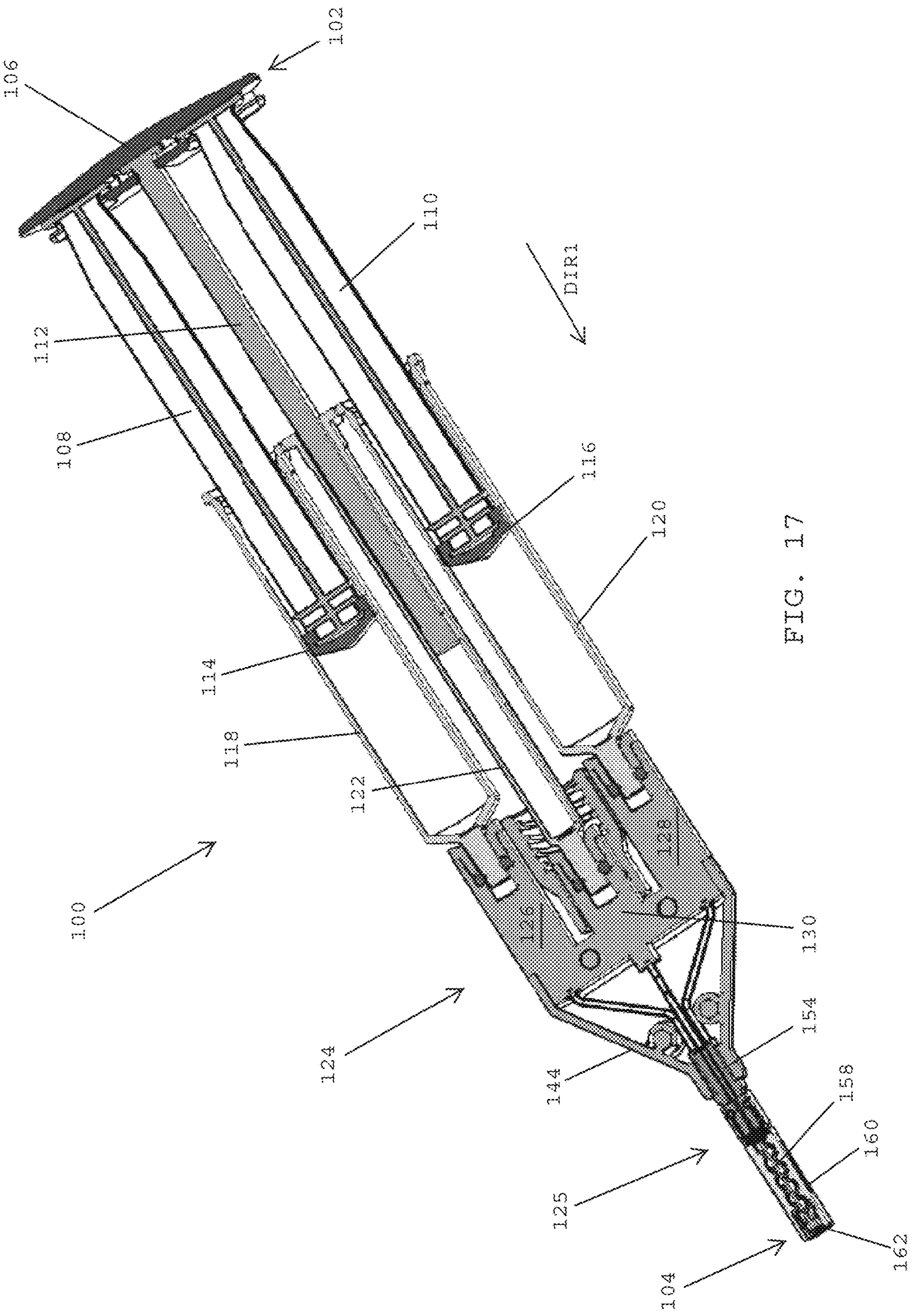
FIG. 17 is a cross-sectional view of an applicator instrument including a proximal end having three syringe barrels and a distal end having a spray tip assembly, in accordance with one embodiment of the present patent application.

Referring to FIG. 17, in one embodiment, the distal ends of the syringe plungers 108, 110, 112 are desirably inserted into the respective syringe barrels 118, 120, and 122. The proximal ends of the syringe plungers 108, 110, 112 may be secured within the syringe plunger receiving slots 210, 212, 214 (FIG. 10C) that are accessible at the distal face of the plunger head 106 to provide for simultaneous distal movement of the syringe plungers 108, 110, 112 in the direction designated DIR1 toward the distal end 104 of the applicator instrument 100. In one embodiment, the first piston head 114 is secured to the distal end of the first syringe plunger 108 and the second piston head 116 is secured to the distal end of the second syringe plunger 110. In one embodiment, the distal ends of the first, second and third syringe barrels 118, 120, and 122 are secured to the respective connectors 126, 128 and 130 of the fluid manifold 124.

Figure 18:
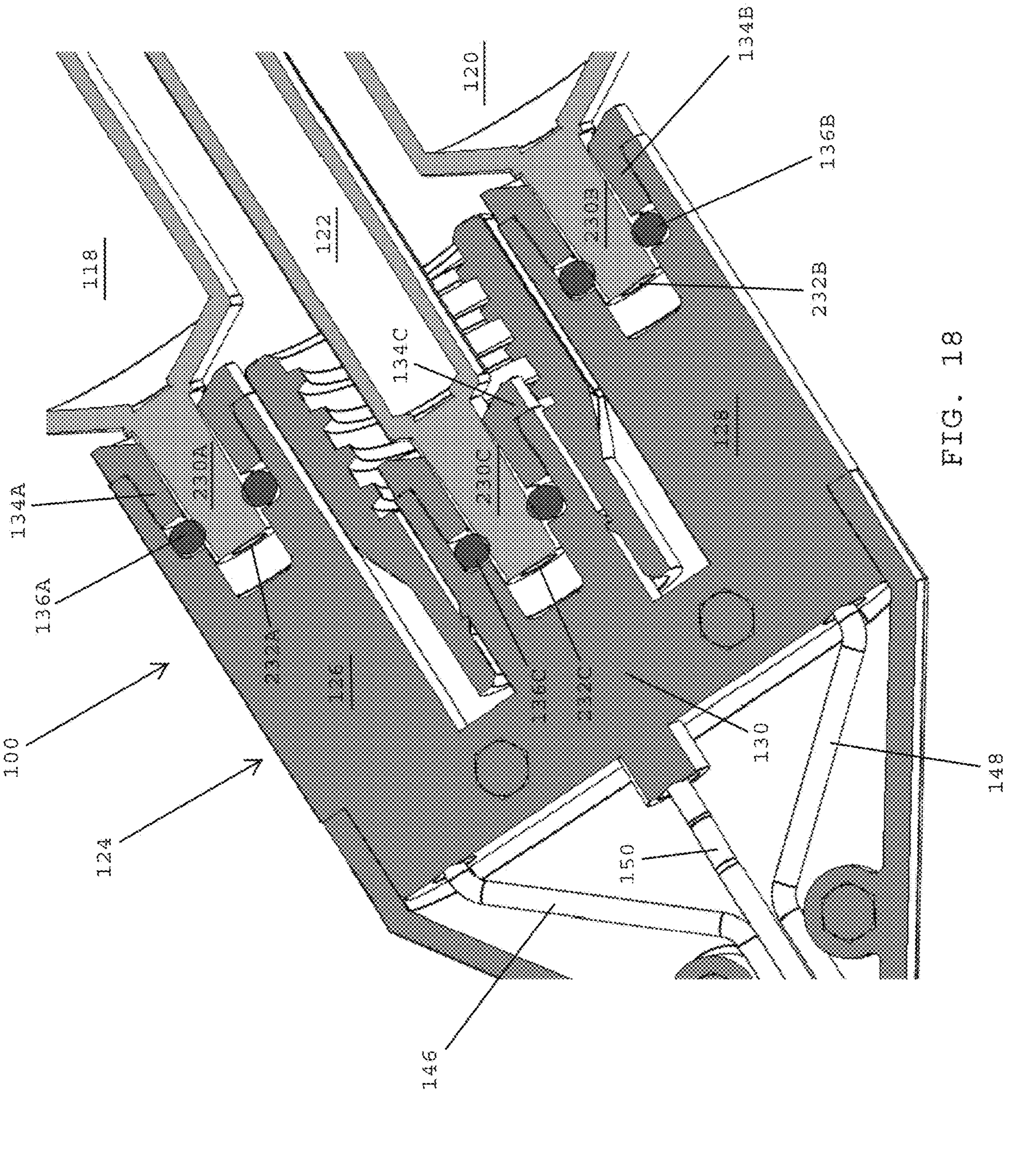
FIG. 18 is a cross-sectional view of a midsection of the applicator instrument shown in FIG. 17.

Referring to FIG. 18, in one embodiment, the distal end 230A of the first syringe barrel 118 is inserted into the first fluid inlet opening of the first connector 126 of the fluid manifold 124. A first O-ring retainer 134A and a first O-ring 136A are utilized to form a fluid-tight coupling between the distal end 230A of the first syringe barrel 118 and the first connector 126 of the fluid manifold 124.

In one embodiment, the distal end 230B of the second syringe barrel 120 is inserted into the third fluid inlet opening of the second connector 128 of the fluid dispensing manifold 124. A second O-ring retainer 134B and a second O-ring 136B are utilized for forming a fluid-tight coupling between the distal end 230B of the second syringe barrel 120 and the second connector 128 of the fluid manifold 124.

In one embodiment, the distal end 230C of the third syringe barrel 122 is inserted into the third fluid inlet opening of the third connector 130 of the fluid dispensing manifold 124. A third O-ring retainer 134C and a third O-ring 136C are utilized for forming a water-tight coupling between the distal end 230C of the third syringe barrel 122 and the third connector 130 of the fluid manifold 124.

In one embodiment, the first fluid dispensing opening 232A located at the distal end 230A of the first syringe barrel 118 is preferably in fluid communication with the first fluid tube 146 for directing the first fluid of a mixture from the first syringe barrel 118 into the first fluid tube 146.

In one embodiment, the second fluid dispensing opening 232B located at the distal end 230B of the second syringe barrel 120 is preferably in fluid communication with the second fluid tube 148 for directing the second fluid of a mixture from the second syringe barrel 120 into the second fluid tube 148.

In one embodiment, the third fluid dispensing opening 232C located at the distal end 230C of the third syringe barrel 122 is preferably in fluid communication with the third fluid tube 150 for directing the third fluid of the mixture from the third syringe barrel 122 into the third fluid tube 150.

Figure 19A:
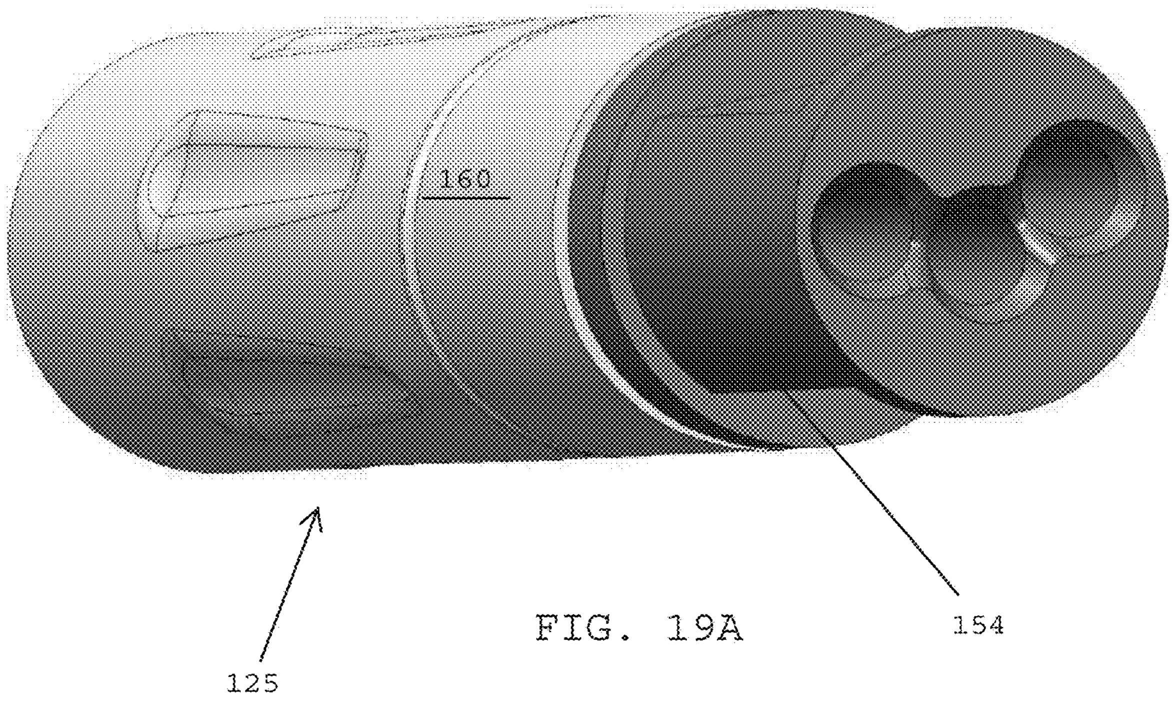
FIG. 19A is a perspective view of a proximal end of a spray tip assembly of an applicator instrument, in accordance with one embodiment of the present patent application.
Figure 19B:
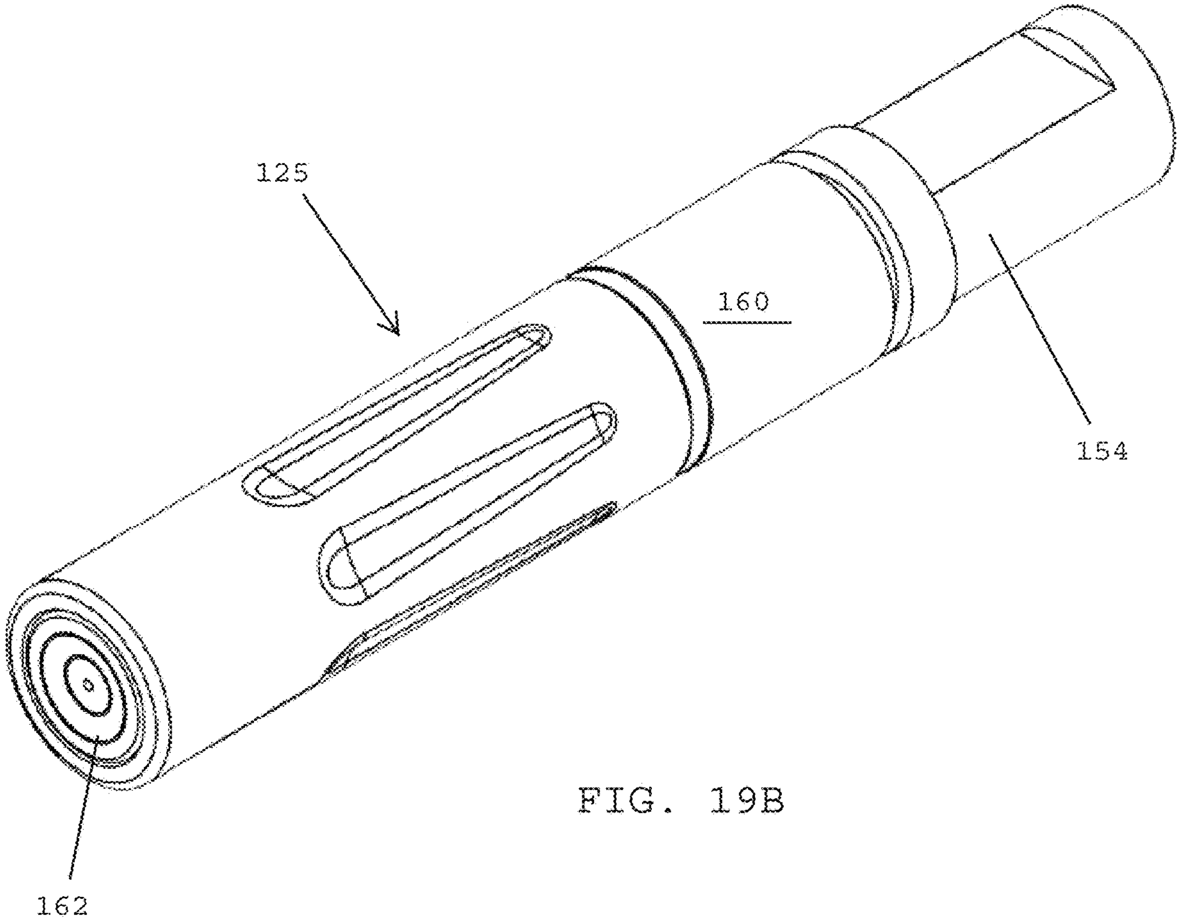
FIG. 19B is a perspective view of a distal end of the spray tip assembly shown in FIG. 19A.

Referring to FIGS. 17, 19A, and 19B, in one embodiment, the distal end 104 of the applicator instrument 100 preferably includes the spray tip assembly 125, which is coupled with the distal ends of the respective upper and lower fluid tube enclosures 142, 144 (FIG. 4). In one embodiment, the spray tip assembly 125 preferably includes the fluid connector 154 having a distal end that is secured to a proximal end of the spray tip housing 160, and the dispensing cap 162 that is preferably assembled with the distal end of the spray tip housing 160.

Figure 20A:
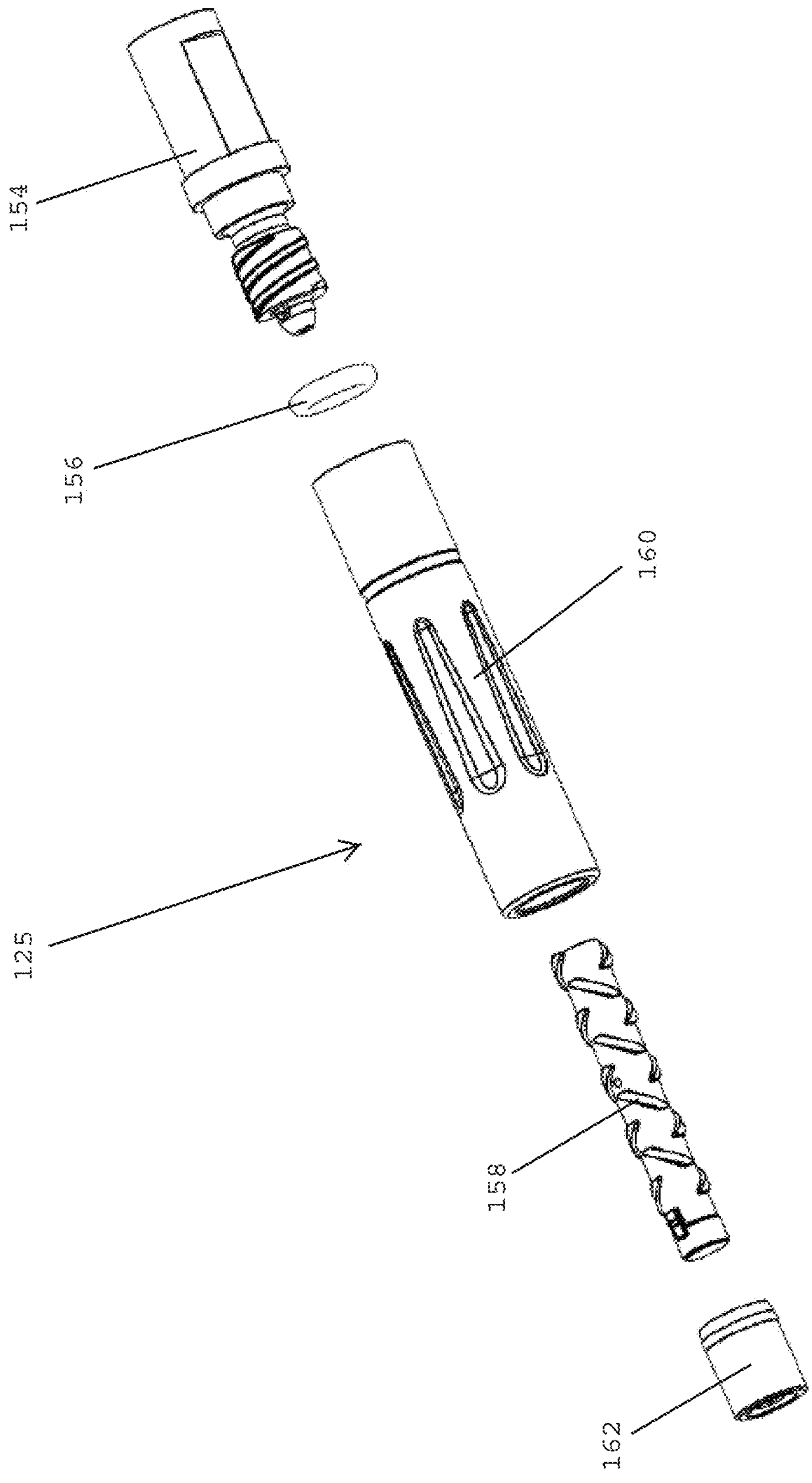
FIG. 20A is an exploded view of the spray tip assembly shown in FIGS. 19A and 19B.
Figure 20B:
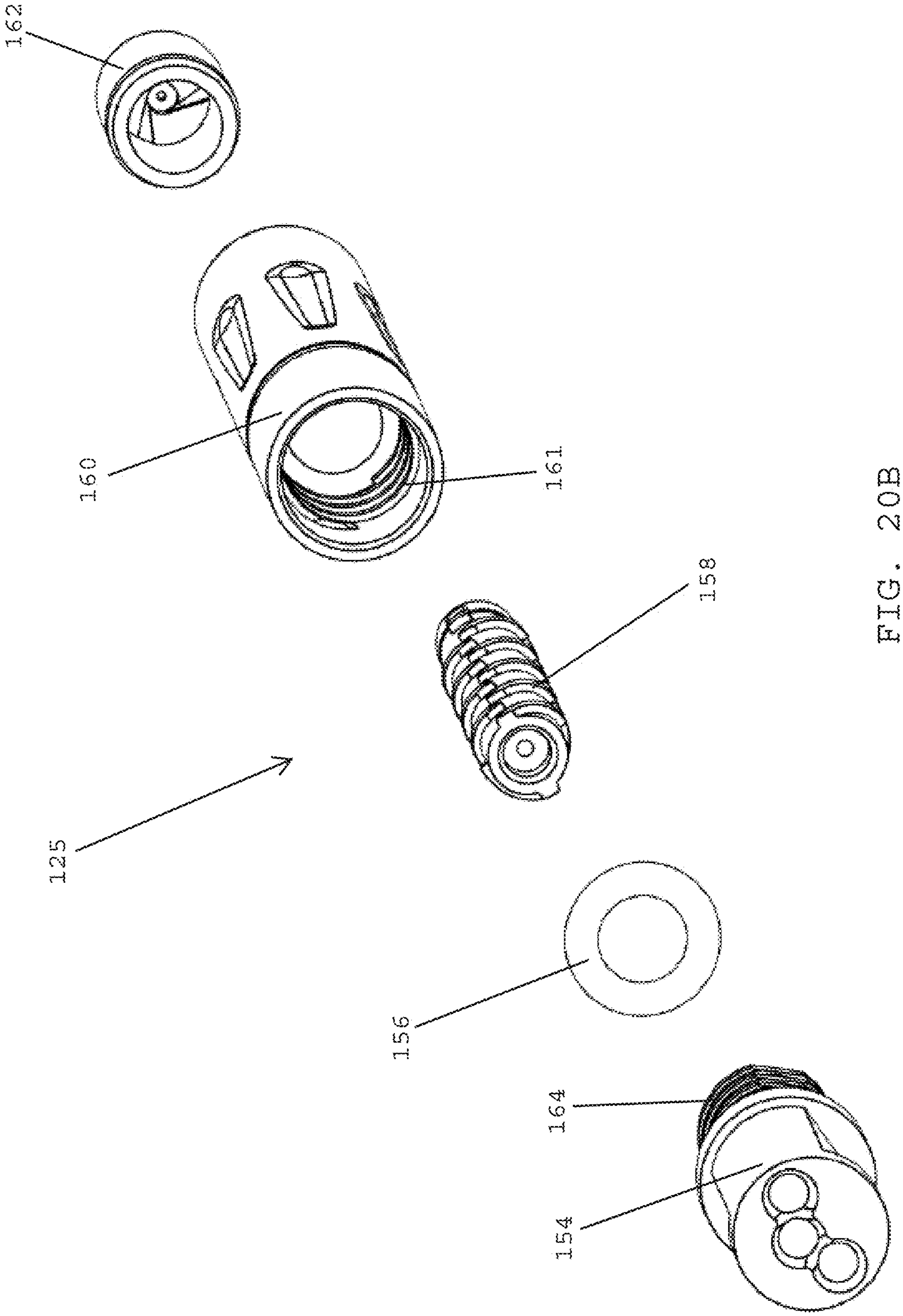
FIG. 20B is another exploded view of the spray tip assembly shown in FIGS. 19A and 19B.

Referring to FIGS. 20A and 20B, in one embodiment, the spray tip assembly 125 preferably includes the fluid connector 154 and the O-ring 156, which is assembled over a neck of the fluid connector 154. The spray tip assembly 125 desirably includes the spray tip housing 160 having an elongated conduit extending along the length thereof that is adapted to receive the mixing element 158. After the O-ring 156 and the fluid connector 154 are assembled together, the O-ring/fluid connector subassembly is preferably inserted into a proximal end of the elongated conduit of the spray tip housing 160 so that the fluid connector 154 may be secured within the proximal end of the spray tip housing 160. The dispensing cap 162 is preferably inserted into a distal end of the elongated conduit of the spray tip housing 160 for being secured to the distal end of the spray tip housing 160.

Referring to FIG. 20B, in one embodiment, the spray tip housing 160 preferably has internal threads 161 that are located adjacent a proximal end of the spray tip housing. In one embodiment, the external threads 164 of the fluid connector 154 are preferably adapted to mesh with the internal threads 161 of the spray tip housing 160 for securing the distal end of the fluid connector 154 with the proximal end of the spray tip housing 160.

Figure 21A:
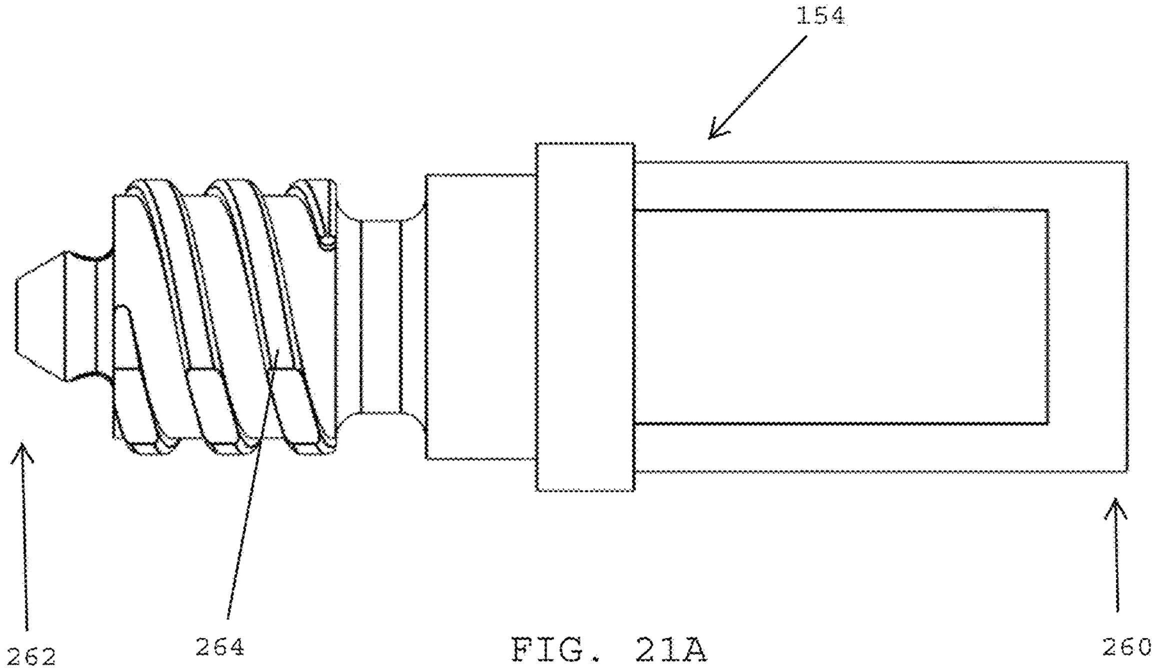
FIG. 21A is a top view of a fluid connector of the spray tip assembly shown in FIGS. 19A-19B and 20A-20B.

Referring to FIG. 21A, in one embodiment, the fluid connector 154 preferably includes a proximal end 260 that is adapted to be coupled with the distal ends of the upper and lower fluid tube enclosures 142, 144 (FIG. 2) and a distal end 262 having the external threads 264, which are adapted to engage the internal threads 161 of the spray tip housing 160 (FIG. 20B).

Figure 21B:
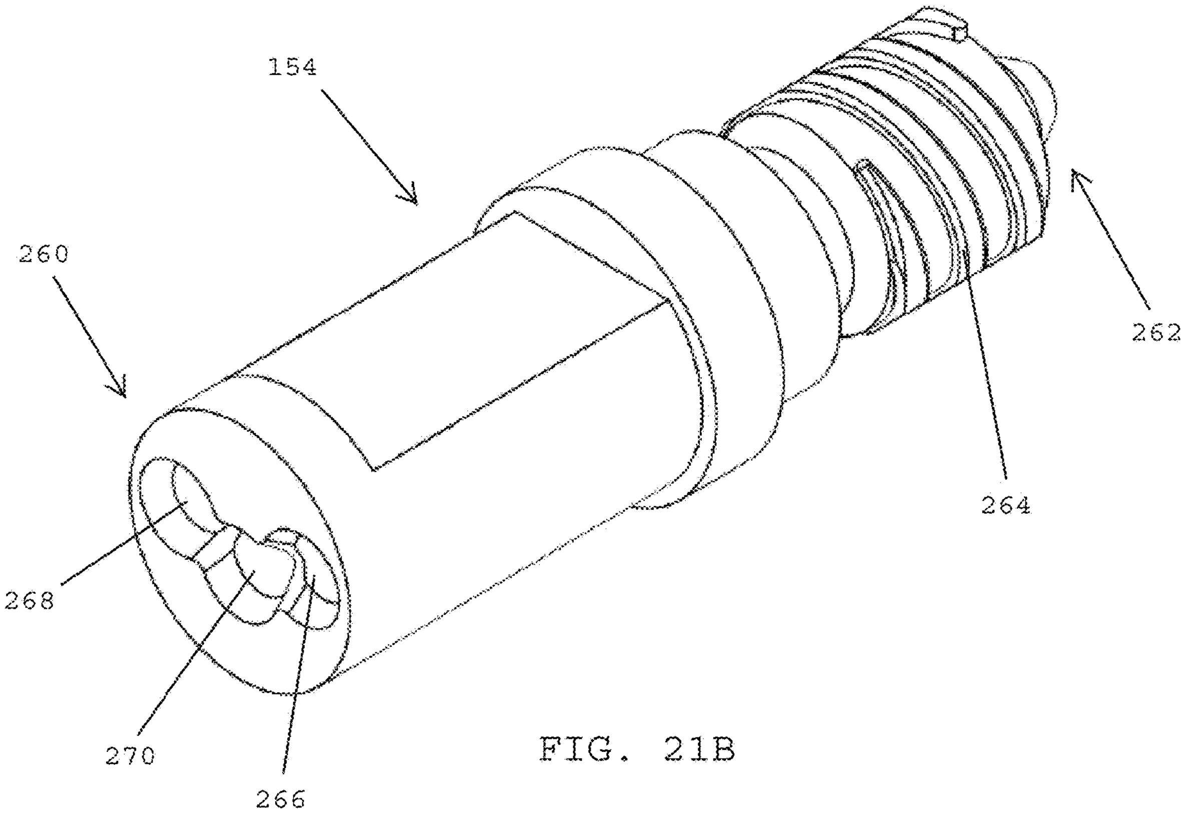
FIG. 21B is a perspective view of a proximal end of the fluid connector shown in FIG. 21A.
Figure 21E:
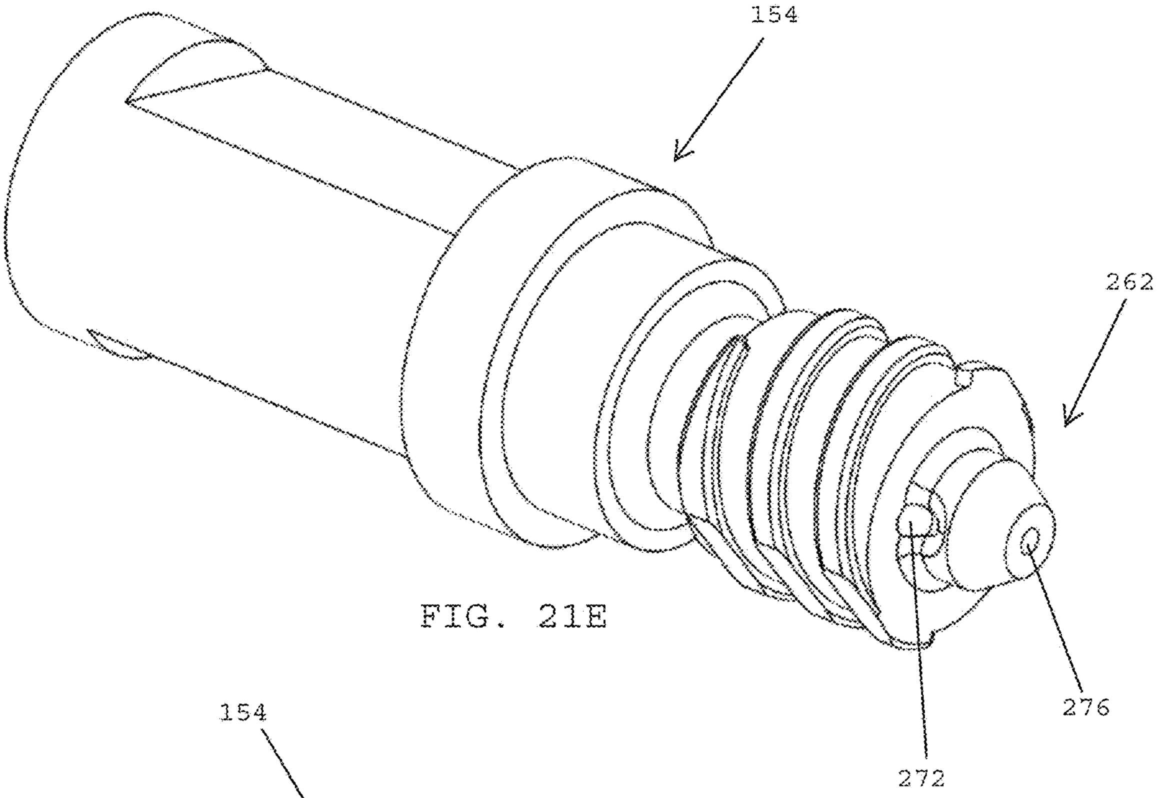
FIG. 21E is a perspective view a distal end of the fluid connector shown in FIGS. 21A-21D.
Figure 21F:
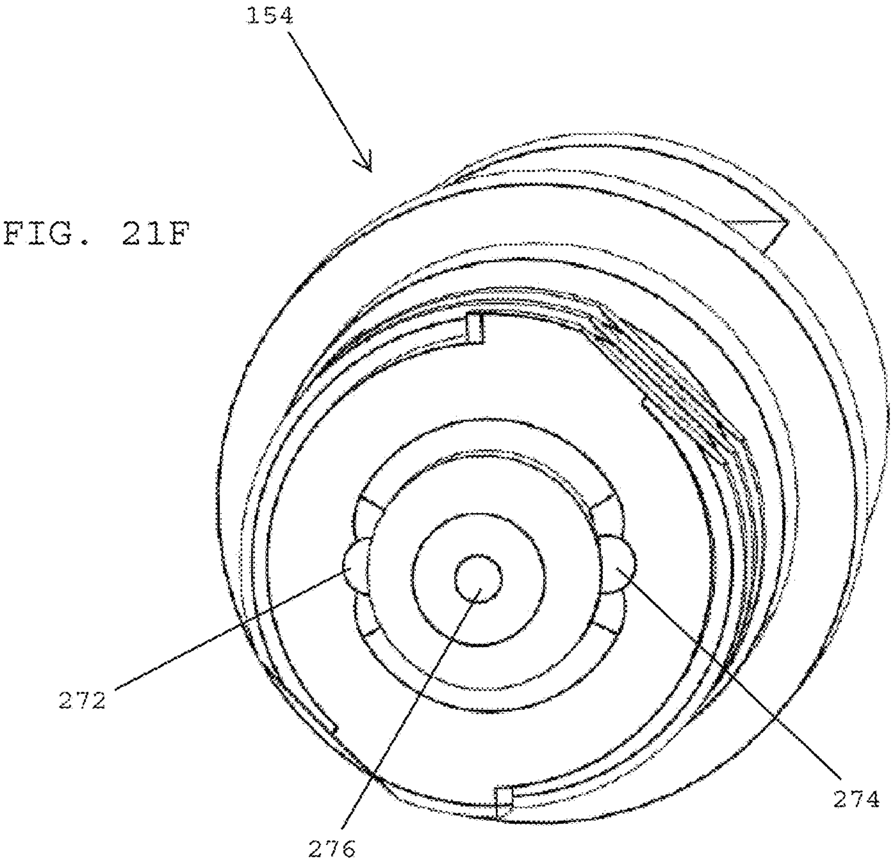
FIG. 21F is another perspective view of the distal end view of the fluid connector shown in FIGS. 21A-21E.
Figure 21G:
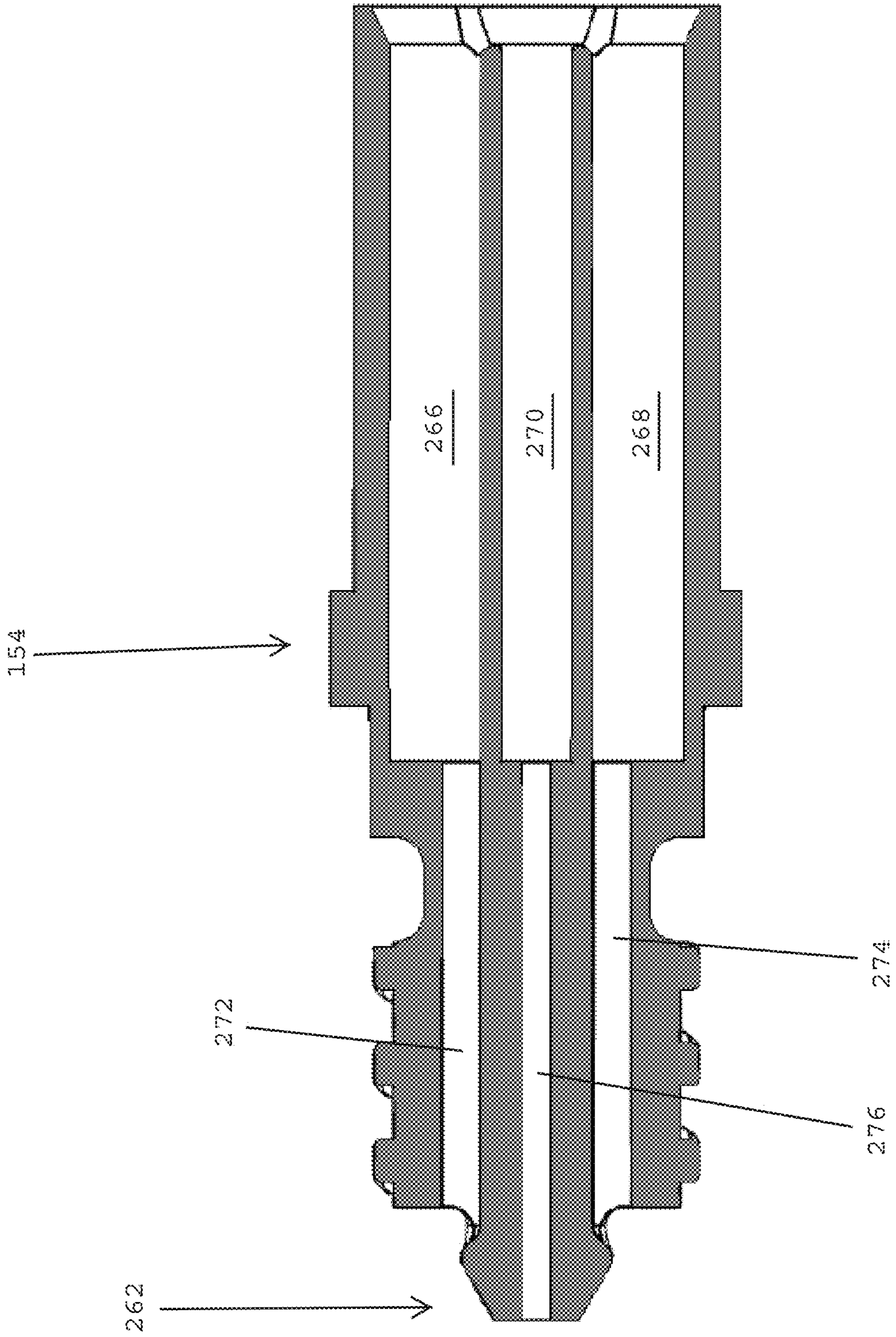
FIG. 21G is a cross-sectional view of the fluid connector shown in FIGS. 21A-21F.

Referring to FIGS. 21B-21D, in one embodiment, the proximal end 260 of the fluid connector 154 preferably includes a first fluid tube opening 266 that is adapted to receive the first fluid tube 146 (FIG. 2), a second fluid tube opening 268 that is adapted to receive the second fluid tube 148 (FIG. 2), and a third fluid tube opening 270 that is adapted to receive the third fluid tube 150 (FIG. 2).

Referring to FIGS. 21D-21G, in one embodiment, the first fluid tube opening 266 of the fluid connector 154 is preferably in fluid communication with a first fluid channel 272, which is open at the distal end 262 of the fluid connector 154. In one embodiment, the second fluid tube opening 268 is preferably in fluid communication with a second fluid channel 274, which is open at the distal end 262 of the fluid connector 154. In one embodiment, the third fluid tube opening 270 of the fluid connector 154 is preferably in fluid communication with a third fluid channel 276, which is open at the distal end 262 of the fluid connector 154. The respective first, second and third fluid channels 272, 274, 276 preferably maintain the three fluids of the three component mixture separated and spaced away from one another until they are introduced into the spray tip housing for being mixed together.

Figure 22A:
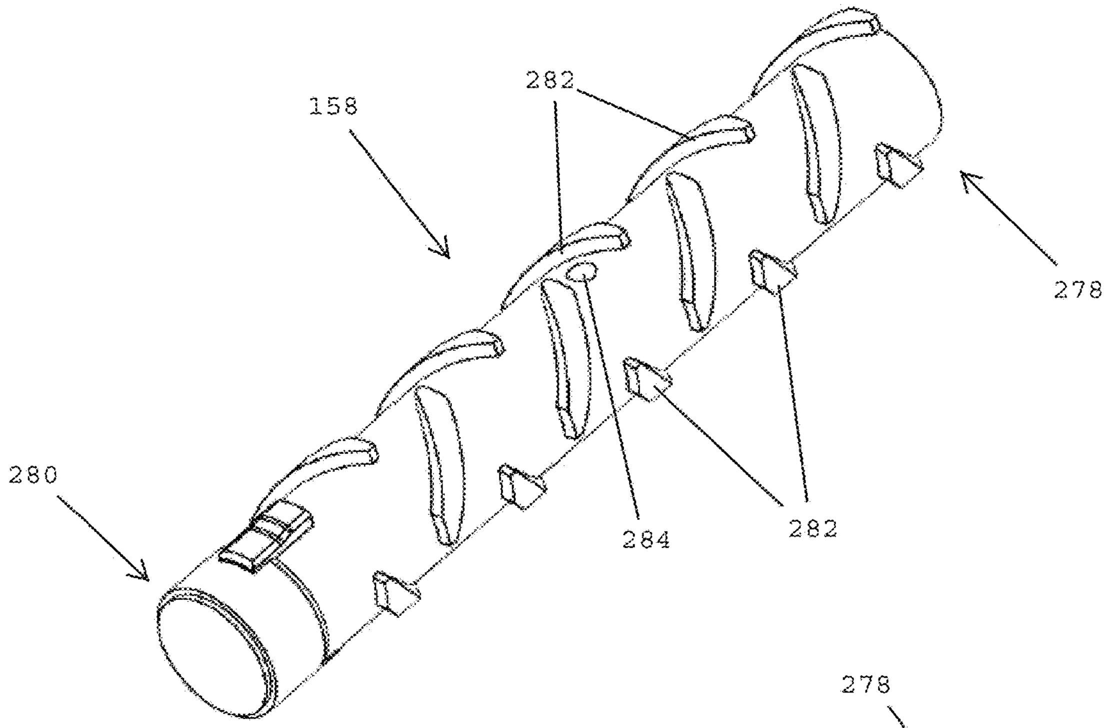
FIG. 22A is a perspective view of a mixing element of the spray tip assembly of an applicator instrument, in accordance with one embodiment of the present patent application.
Figure 22B:
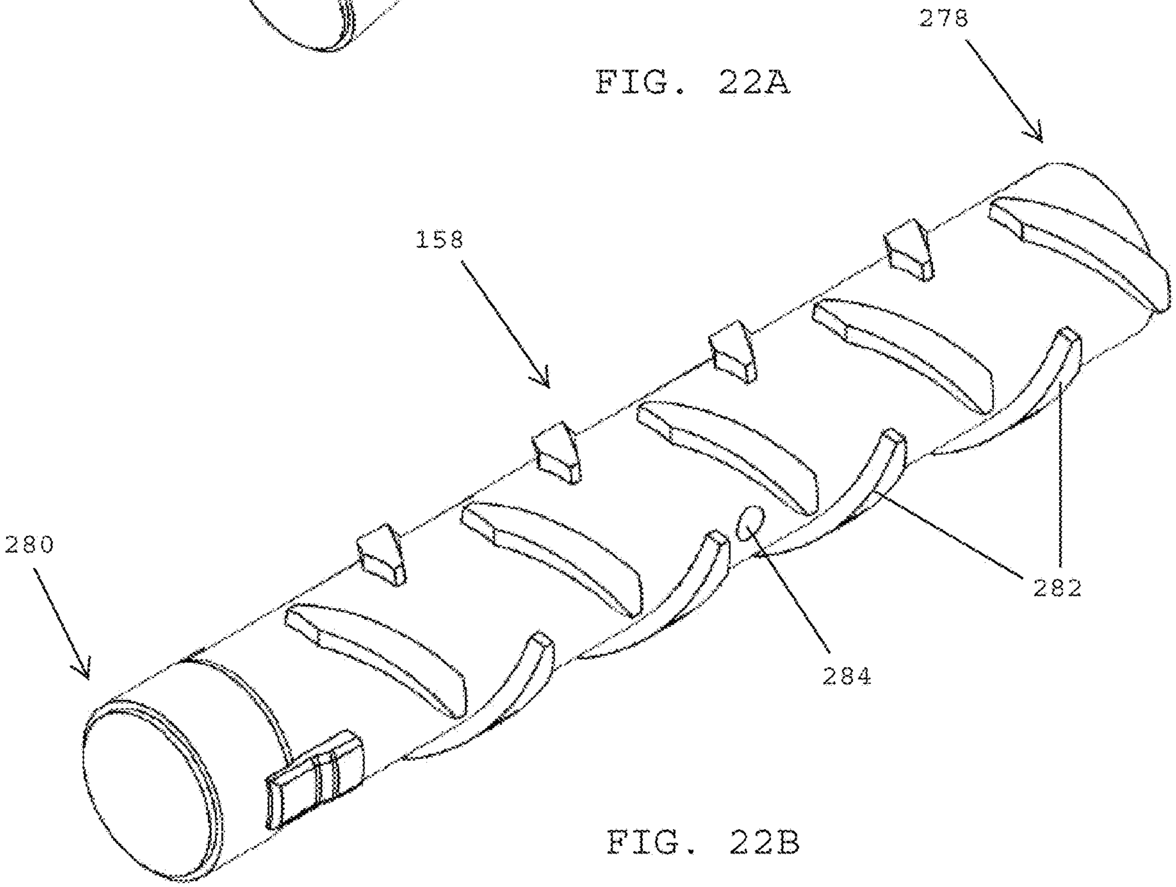
FIG. 22B is another perspective view of the mixing element shown in FIG. 22A.

Referring to FIGS. 17, 22A, and 22B, in one embodiment, the spray tip assembly 125 of the applicator instrument 100 (FIG. 1A) preferably includes a mixing element 158 that is disposed inside the spray tip housing 160. The mixing element 158 may have the shape of a cylinder or a cylindrical-shaped rod. In one embodiment, the mixing element 158, which is preferably located downstream of the fluid connector 154, is adapted for mixing together the three fluids that pass through the fluid connector. In one embodiment, the mixing element 158 preferably has a proximal end 278 and a distal end 280. The outer surface of the mixing element 158 preferably includes a plurality of static mixing fins 282 that are spaced from one another over the outer surface of the mixing element 158 for mixing together the three fluids as the fluids flow downstream through the mixing chamber. In one embodiment, the mixing element 158 preferably includes one or more laterally extending third fluid exit openings 284 that may be used for dispensing the third fluid into the mixing space (e.g., an annular mixing space) that surrounds the outer surface of the mixing element 158. In one embodiment, the annular mixing space is preferably located between the outer surface of the mixing element and the inner surface of the spray tip housing 160.

Referring to FIGS. 17, and 23A-23C, in one embodiment, the spray tip housing 160 of the spray tip assembly 125 preferably has a cylindrical or tube-shaped body with a proximal end 288, a distal end 290 and an elongated conduit 292 that extends from the proximal end to the distal end thereof. In one embodiment, the spray tip housing 160 preferably includes an outer wall having an inner surface with internal threads 161 that are located adjacent the proximal end 288 thereof. In one embodiment, the internal threads 161 of the spray tip housing 160 preferably engage the external threads 264 of the fluid connector 154 (FIG. 21A) for securing the distal end of the fluid connector 154 to the spray tip housing 160.

Figure 23A:
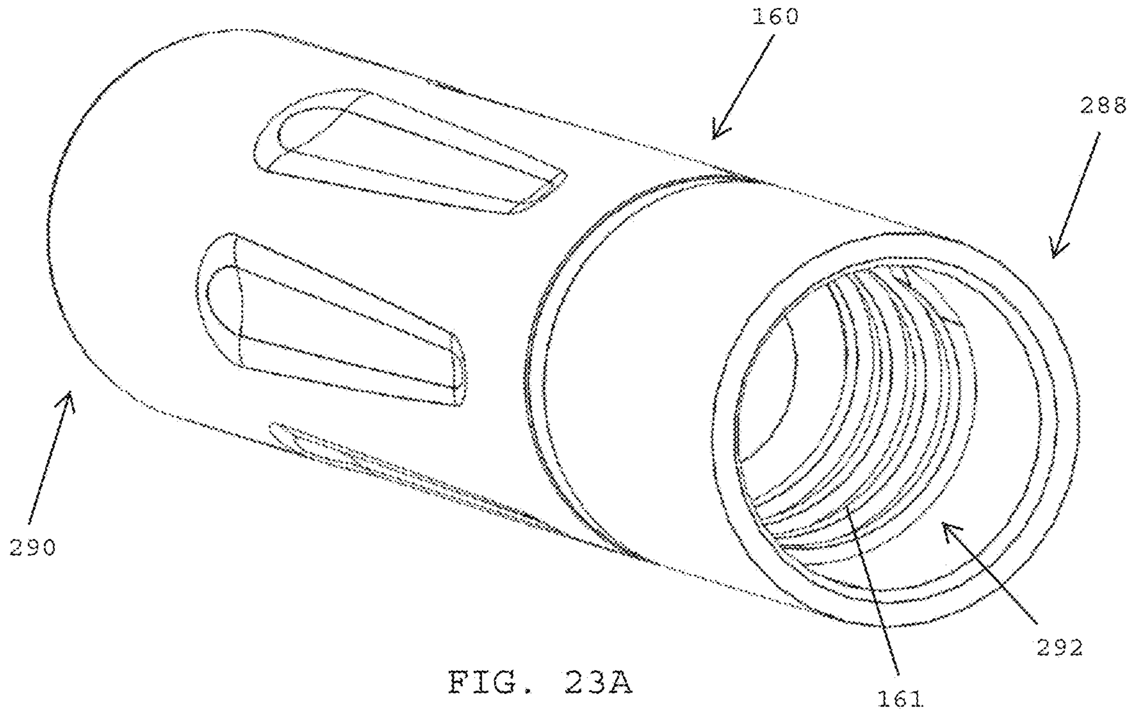
FIG. 23A is a perspective view of a proximal end of a spray tip housing of a spray tip assembly, in accordance with one embodiment of the present patent application.
Figure 23B:
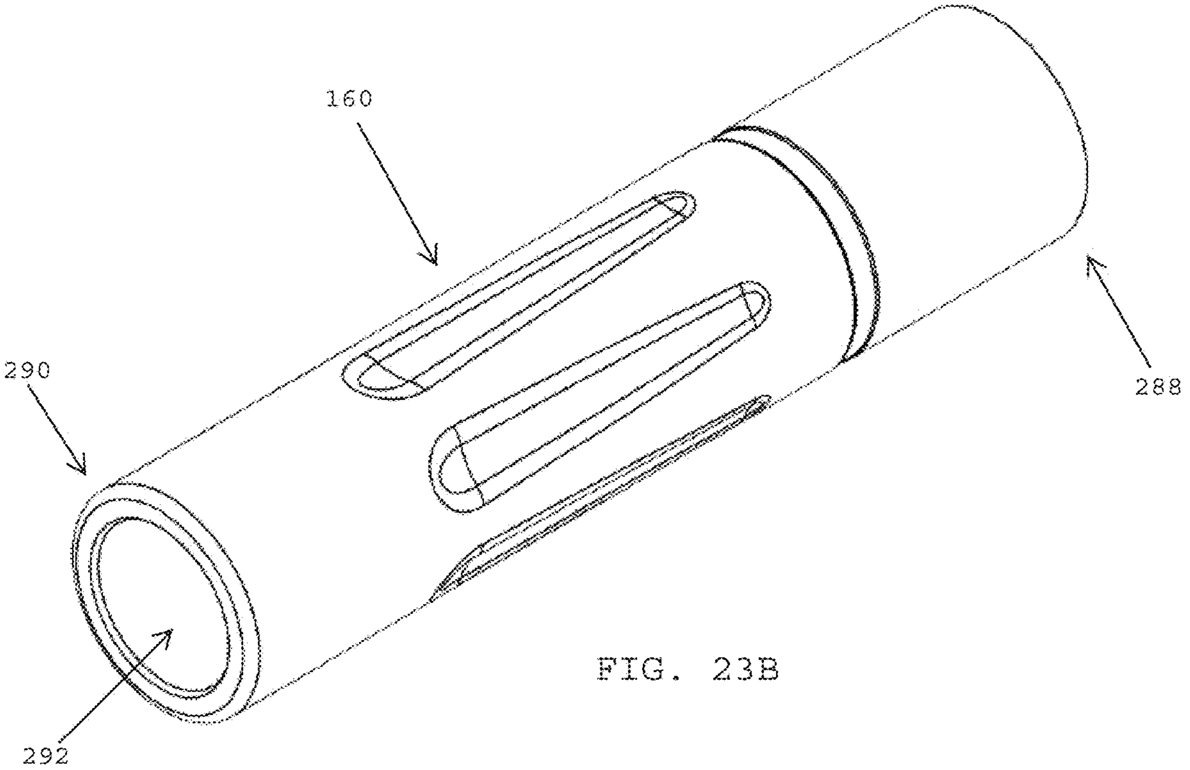
FIG. 23B is a perspective view of a distal end of the spray tip housing shown in FIG. 23A.
Figure 23C:
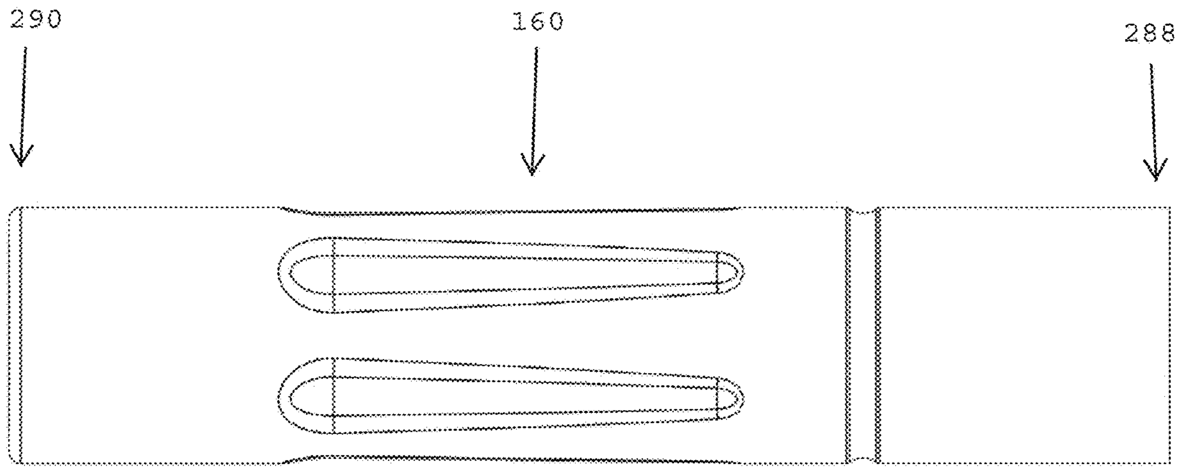
FIG. 23C is a side elevation view of the spray tip housing shown in FIGS. 23A and 23B.
Figure 23D:
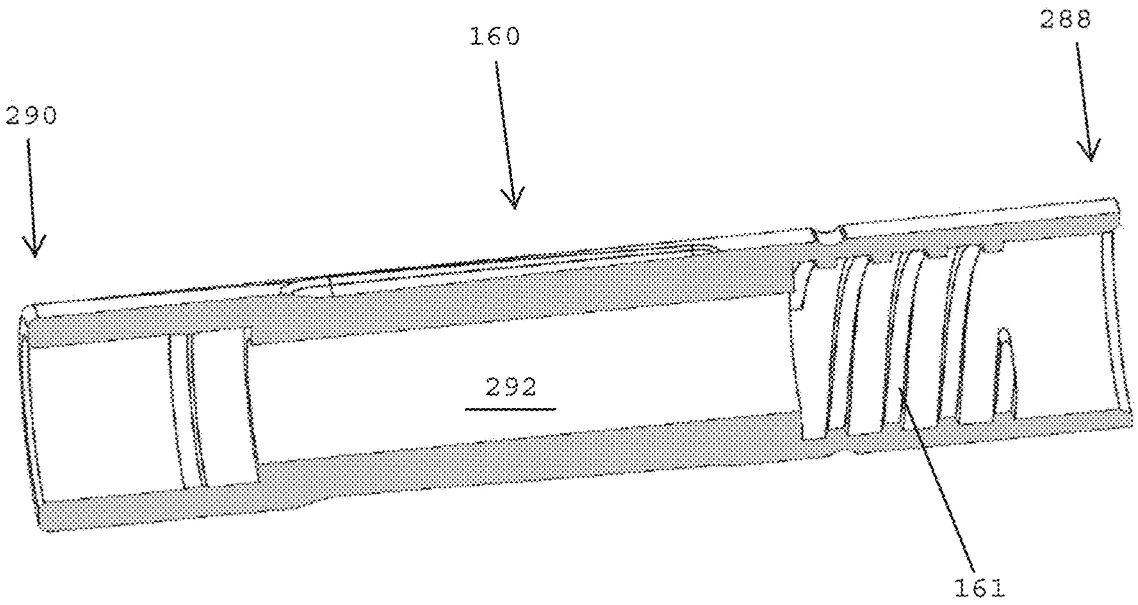
FIG. 23D is a cross-sectional view of the spray tip housing shown in FIGS. 23A-23C.

Referring to FIGS. 17 and 23D, in one embodiment, the elongated conduit 292 of the spray tip housing 160 is preferably adapted to receive the mixing element 158. The internal threads 161 at the proximal end 288 of the spray tip housing 160 are desirably adapted to engage the external threads 264 (FIG. 21B) located at the distal end of the fluid connector 154.

Figure 24A:
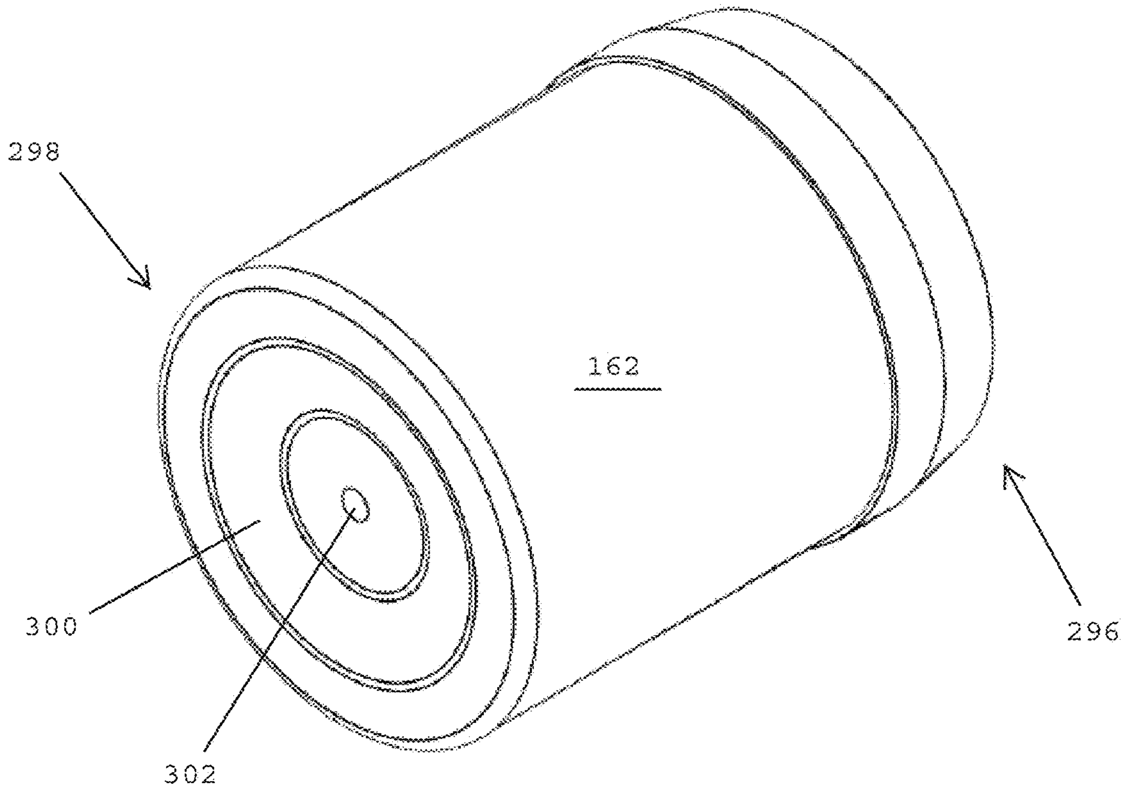
FIG. 24A is a perspective view of a distal end of a dispensing cap of a spray tip assembly shown in FIGS. 19A-19B and 20A-20B, in accordance with one embodiment of the present patent application.
Figure 24B:
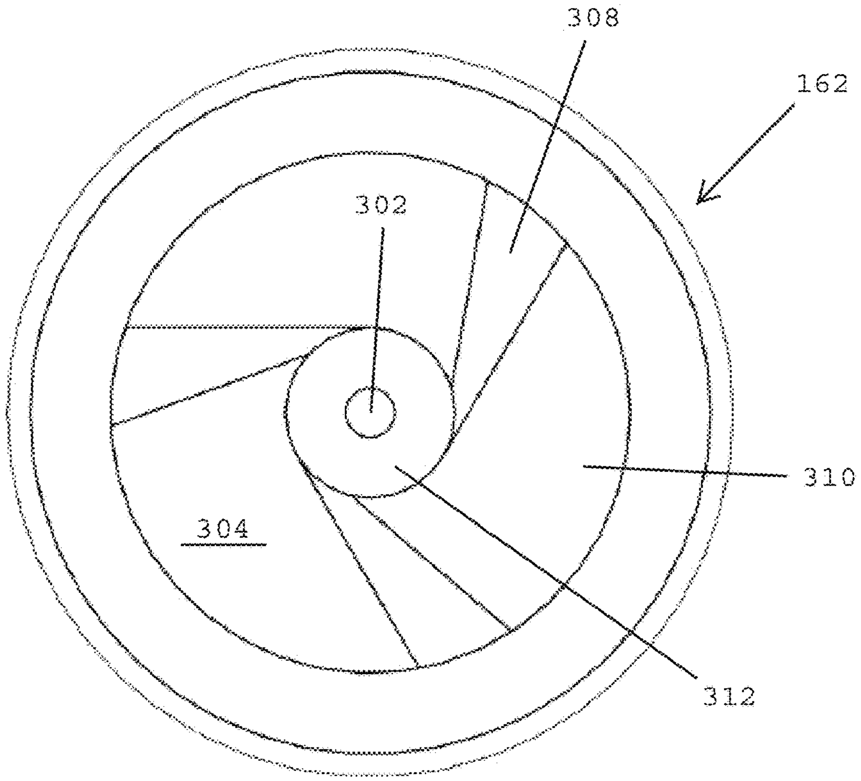
FIG. 24B is a proximal end view of the dispensing cap shown in FIG. 24A.
Figure 24C:
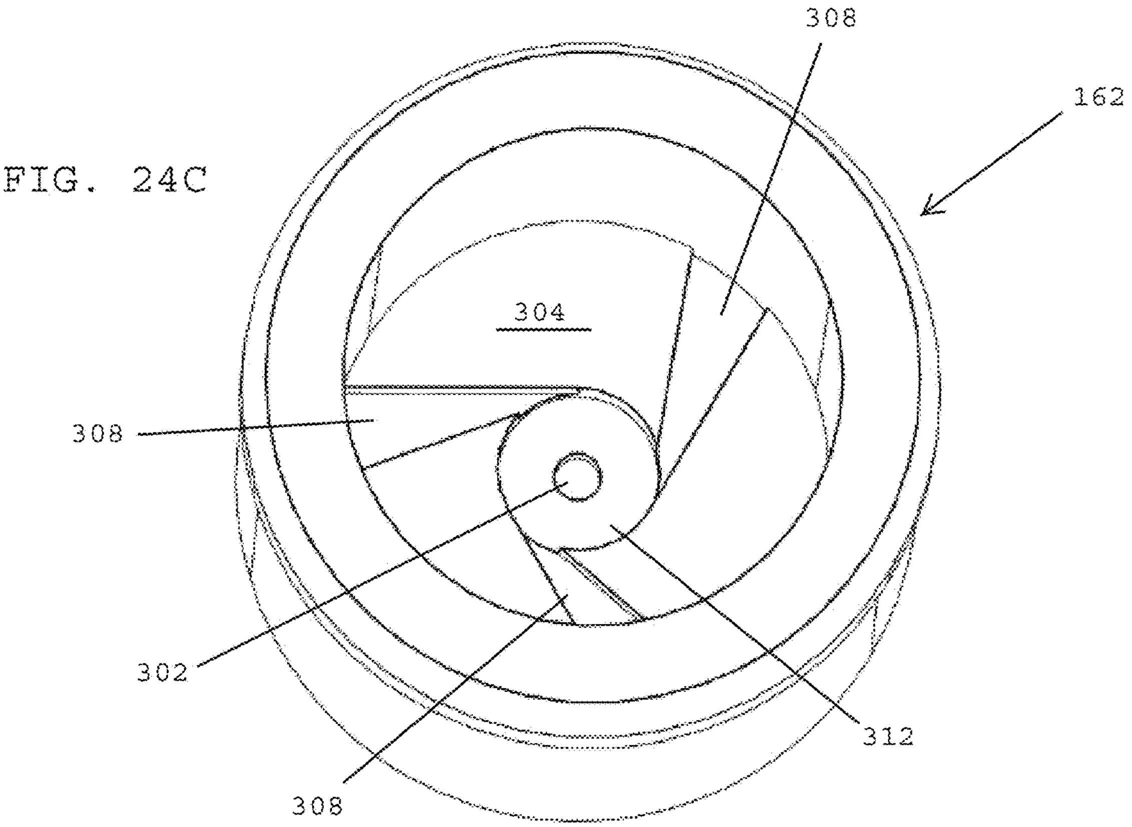
FIG. 24C is a perspective view of the proximal end of the dispensing cap shown in FIGS. 24A and 24B.
Figure 24C:
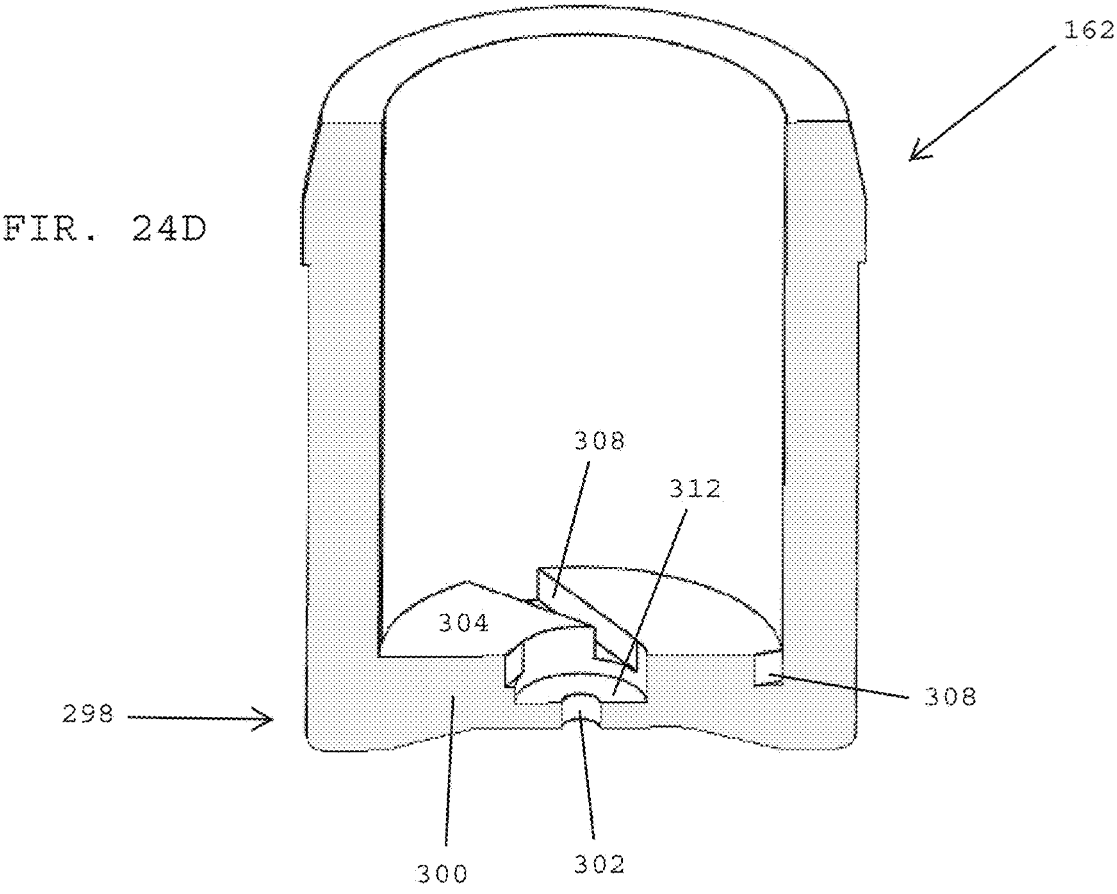

Referring to FIGS. 17 and 24A, in one embodiment, the spray tip assembly 125 of the applicator instrument 100 preferably includes the dispensing cap 162 that is adapted to be assembled with the distal end 290 of the spray tip housing 160 (FIG. 23D). In one embodiment, the dispensing cap 162 preferably has an open proximal end 296 that opposes a distal end of the mixing element and a closed distal end 298 having an end wall 300 with a dispensing opening 302.

Referring to FIGS. 24A-24D, in one embodiment, the end wall 300 of the dispensing cap 162 preferably has an inner face 304 that surrounds the dispensing opening 302. The dispensing cap 162 preferably includes a swirl chamber 306 having radially extending grooves 308 that direct fluids (e.g., the three fluids from the three syringes) from an outer perimeter 310 of the inner face 304 toward a circular depression 312 that surrounds the dispensing opening 302. The swirl chamber 306 preferably provides for enhanced mixing of the fluids of a multiple component mixture prior to being dispensed through the dispensing opening 302 of the dispensing cap 162.

In one embodiment, the dispensing cap 162 may have one or more of the structural features of the dispensing caps disclosed is commonly assigned U.S. patent application Ser. No. 16/593,783, filed on Oct. 4, 2019, the disclosure of which is hereby incorporated by reference herein.

In one embodiment, the dispensing cap 162 may have one or more of the structural features of the orifice cups disclosed is commonly assigned U.S. patent application Ser. No. 16/593,799, filed on Oct. 4, 2019, the disclosure of which is hereby incorporated by reference herein.

Figure 25:
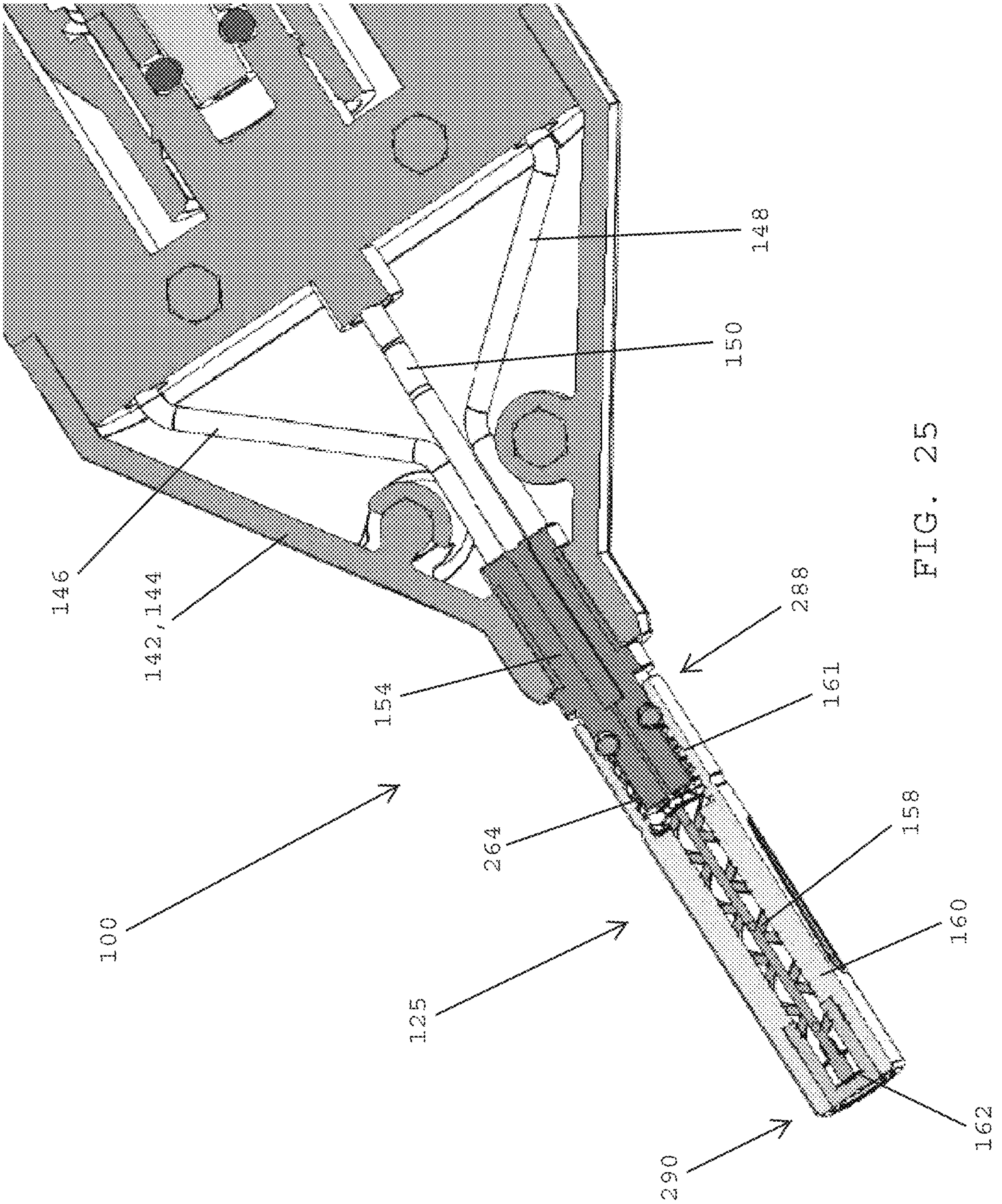
FIG. 25 is a cross-sectional view of the spray tip assembly shown in FIGS. 19A-19B and 20A-20B, in accordance with one embodiment of the present patent application.

Referring to FIG. 25, in one embodiment, the spray tip assembly 125 of the applicator instrument 100 is preferably secured to the distal ends of the upper and lower fluid tube enclosures 142, 144 (FIG. 2) so that the three fluids directed through the respective first, second and third fluid tubes 146, 148, and 150 may be directed into the three fluid tube openings 266, 268, and 270 (FIGS. 21C and 21G) located at the proximal end of the fluid connector 154. In one embodiment, the external threads 264 (FIG. 21B) at the distal end of the fluid connector 154 mesh with the internal threads 161 (FIG. 20B) at the proximal end 288 of the spray tip housing 160 for securing the spray tip housing to the fluid connector. In one embodiment, the mixing element 158 is preferably disposed within the elongated conduit of the spray tip housing 160, with the mixing chamber being located between the inner surface of the outer wall of the spray tip housing 160 and the outer surface of the mixing element 158. Upon depressing the plunger head 106 in the distal direction DIR1 (FIG. 17), the three fluids contained within the respective first, second and third fluid tubes 146, 148, and 150 are forced to flow downstream into the three fluid inlet openings of the fluid connector 154, whereupon the three fluids pass through the respective fluid channels of the fluid connector 154 and are directed toward the proximal end of the mixing element 158. The mixing element 158 preferably mixes the three fluids within the mixing chamber of the spray tip housing 160 prior to the final mixture being expressed from the dispensing opening of the dispensing cap 162.

In one embodiment, the first fluid having the first reactive component (e.g., Fibrinogen) and the second fluid having the second reactive component (e.g., Thrombin) are mixed together within the mixing chamber of the spray tip assembly 125 to form a first mixture, and then the third fluid (e.g., a diluent or pH modifying buffer) is added to the first mixture within the mixing chamber to form a final mixture that is expressed (e.g., sprayed) from the dispensing opening of the dispensing cap 162.

In one embodiment, the mixing chamber is an elongated mixing chamber that is located inside the spray tip housing 160. The elongated mixing chamber may have an annular shape. In one embodiment, the spray tip housing 160 has a proximal end for receiving the respective first, second, and third fluids and a distal end that receives the dispensing cap 162.

Figure 26:
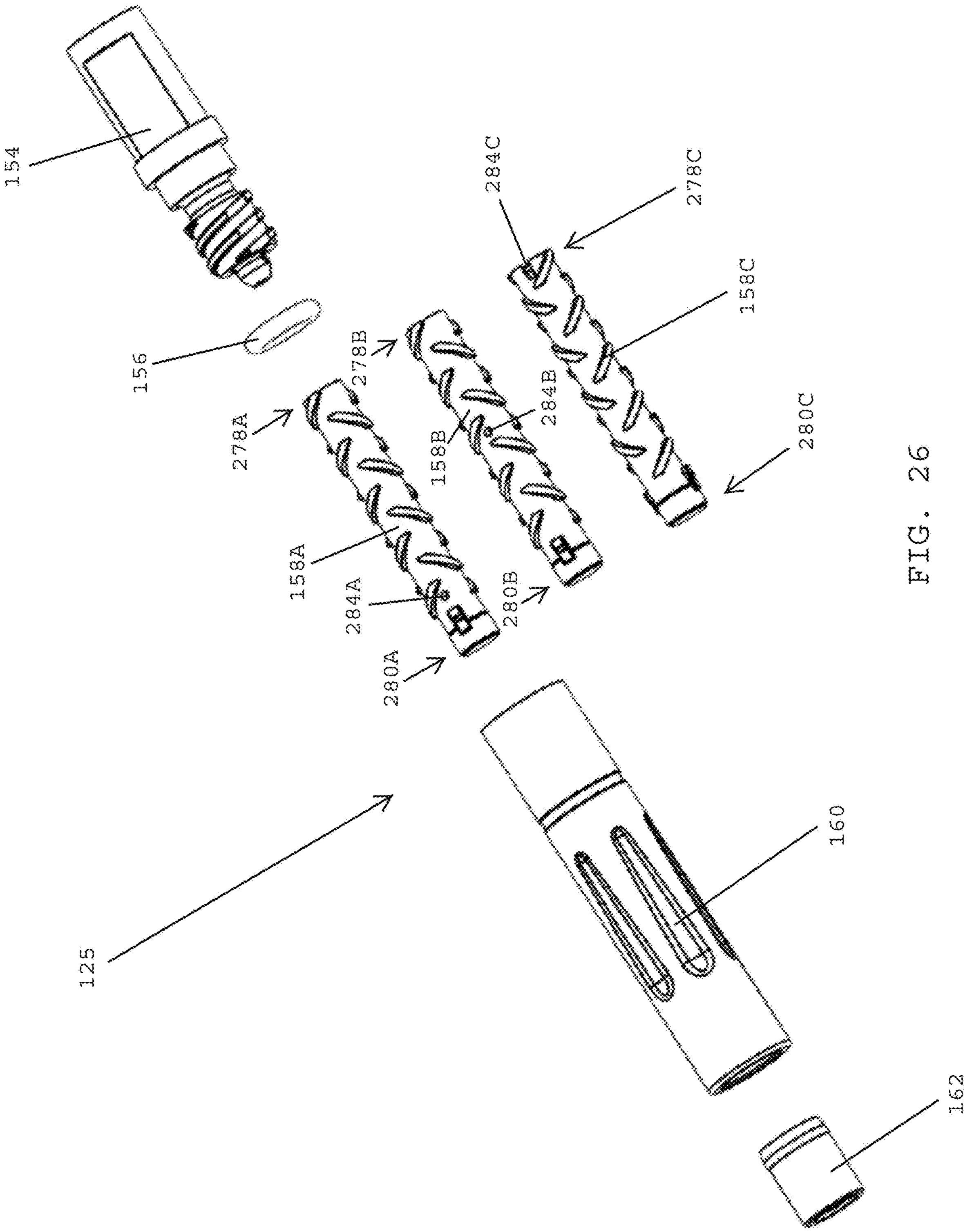
FIG. 26 is an exploded view of a spray tip assembly of an applicator instrument including three different mixing elements, each having different mixing characteristics, in accordance with one embodiment of the present patent application.
Figure 27A:
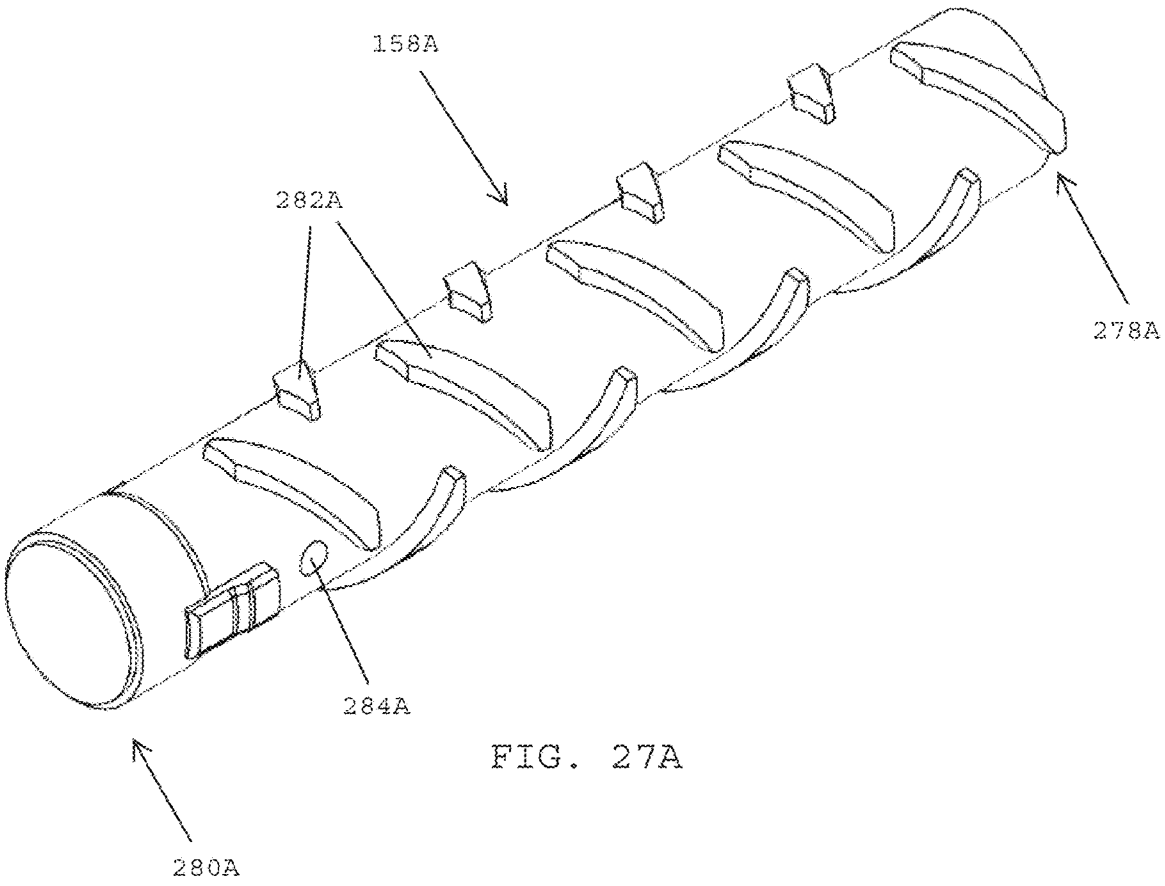
FIG. 27A is a perspective view of a mixing element having third fluid exit openings that are located adjacent a distal end of the mixing element, in accordance with one embodiment of the present patent application.
Figure 27B:
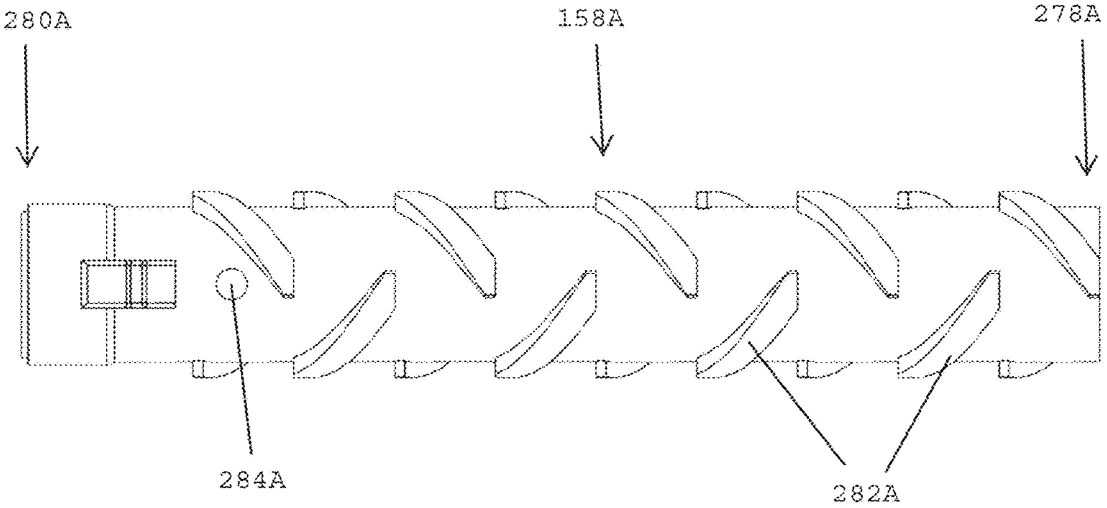
FIG. 27B is a top plan view of the mixing element shown in FIG. 27A.
Figure 27C:
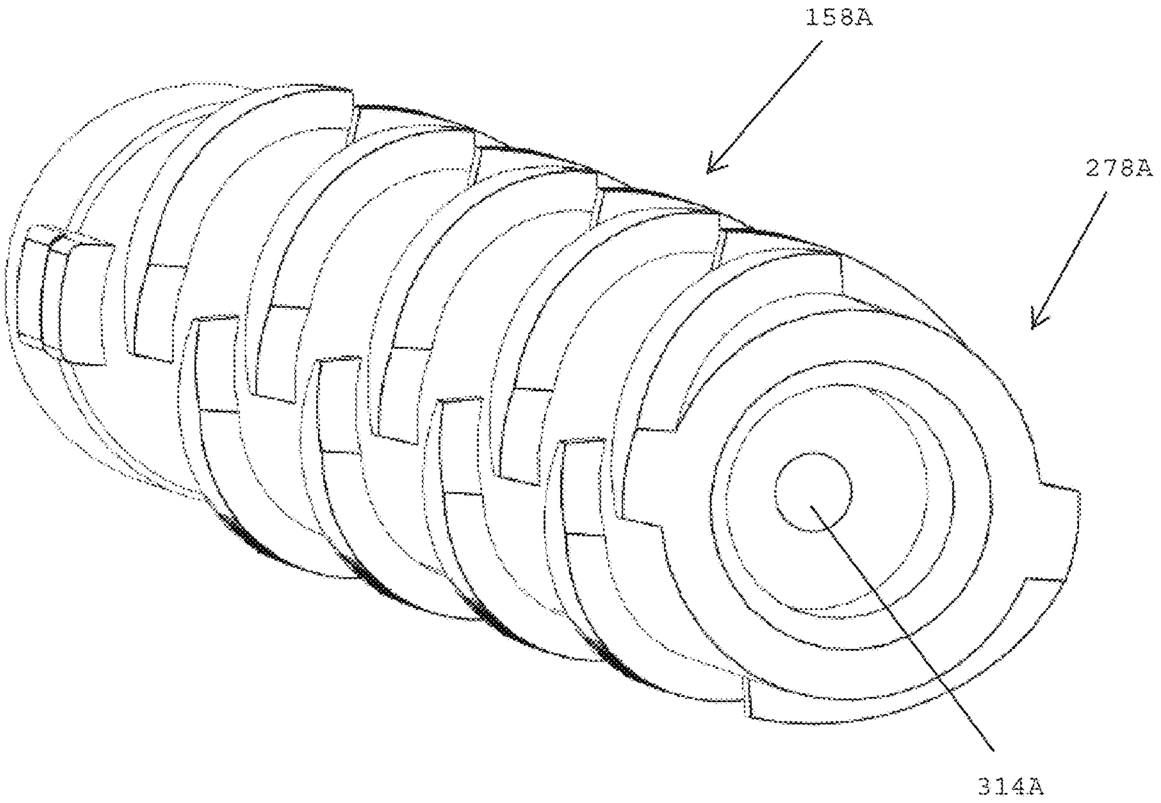
FIG. 27C is a perspective view of a proximal end of the mixing element shown in FIGS. 27A and 27B.
Figure 27D:
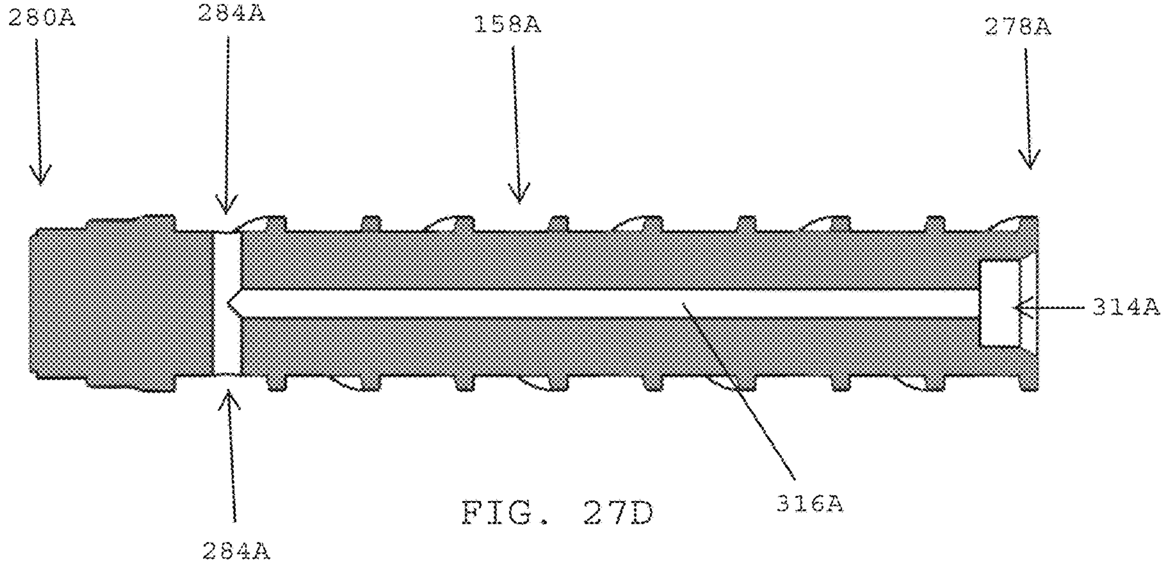
FIG. 27D is a cross-sectional view of the mixing element shown in FIGS. 27A-27C.

Referring to FIG. 26, in one embodiment, the spray tip assembly 125 may include a set of interchangeable mixing elements 158A, 158B, and 158C having different structural characteristics for changing how, when and/or where along the length of the spray tip assembly the third fluid of the biocompatible reactive formulation is added to a first mixture of the first and second fluids. For example, each of the different mixing elements 158A, 158B, and 158C may alter how the third fluid is added into a first mixture of first and second fluids to generate a final mixture that is expressed (e.g., sprayed) onto tissue. In certain preferred embodiments, only one of the mixing elements 158A, 158B, and 158C is disposed inside the spray tip housing 160 at any one time. Thus, the reaction of the first and second reactive components may be controlled by selecting which of the unique mixing elements 158A, 158B, and 158C is utilized.

In one embodiment, the spray tip assembly 125 may utilize a first mixing element 158A having laterally extending third fluid exit openings 284A that are located adjacent the distal end 280A of the mixing element 158A. In this embodiment, the first and second fluids are first mixed together within a mixing chamber at the proximal end of the first mixing element 158A to form a first mixture, and, after the first mixture flows downstream through the mixing chamber toward the distal end of the mixing element 158A, the third fluid is added to the first mixture, via the third fluid exit openings 284A, adjacent the distal end of the first mixing element 158A.

In one embodiment, the spray tip assembly 125 may utilize a second mixing element 158B having laterally extending third fluid exit openings 284B that are located midway between the proximal end 278B and the distal end 280B of the second mixing element. In this embodiment, the first and second fluids are mixed together within the mixing chamber at the proximal end of the second mixing element 158B to form a first mixture, and, as the first mixture flows downstream through the mixing chamber toward the distal end of the mixing element 158B, the third fluid is added to the first mixture, via the third fluid exit openings 284B, at a location that is midway between the proximal end and the distal end of the second mixing element 158B.

In one embodiment, the spray tip assembly 125 may utilize a third mixing element 158C having laterally extending third fluid exit openings 284C that are located adjacent the proximal end 278C of the mixing element. In this embodiment, the first and second fluids are mixed together within the mixing chamber at the proximal end of the third mixing element 158C to form a first mixture, and the third fluid is also added to the first mixture at the proximal end of the third mixing element 158C, via the third fluid exit openings 284C, to form a final mixture. The final mixture then travels the length of the mixing element for further mixing until it is dispensed via the dispensing opening of the dispensing cap 162.

In other embodiments, the third fluid exit openings may be positioned at any location along the length of a mixing element to further modify and control how reactive components react with one another. Thus, an infinite number of different types of reactions may be attained by modifying the structure of the mixing elements.

In one embodiment, a system may include a kit having a first spray tip assembly that has the first mixing element 158A, a second spray tip assembly that has the second mixing element 158B, and a third spray tip assembly that has the third mixing element 158C, whereby only one of the three spray tip assemblies is secured to the distal end of the applicator instrument at any one time. Thus, an operator may modify the characteristics of a biocompatible reactive formulation (i.e., by controlling how, when and/or where the first and second reactive components react with one another) that is dispensed from the applicator instrument by changing the spray tip assembly that is secured to the distal end of the applicator instrument. In one embodiment, a first spray tip assembly may be disconnected from a fluid connector and replaced by a second spray tip assembly that is secured to the fluid connector for changing how the three fluids are mixed together within the spray tip housing.

Referring to FIGS. 27A-27D, in one embodiment, the first mixing element 158A (FIG. 26) preferably has an outer surface with a cylindrical shape (e.g., a cylindrical rod) that extends between a proximal end 278A and a distal end 280A thereof. The outer surface of the first mixing element 158A preferably has a plurality of static mixing fins 282A that are spaced from one another along the length of the first mixing element. The first mixing element 158A preferably has a third fluid inlet opening 314A, and a third fluid conduit 316A that is in fluid communication with the third fluid inlet opening 314A and that extends from the third fluid inlet opening 314A to the laterally extending third fluid exit openings 284A located adjacent the distal end 280A of the first mixing element 158A. In one embodiment, the third fluid flows into the third fluid inlet opening 314A, flows downstream through the third fluid conduit 316A, and then flows laterally through the third fluid exit openings 284A for being directed into the mixing chamber so that the third fluid may be added into the first mixture of the first and second fluids.

Figure 28A:
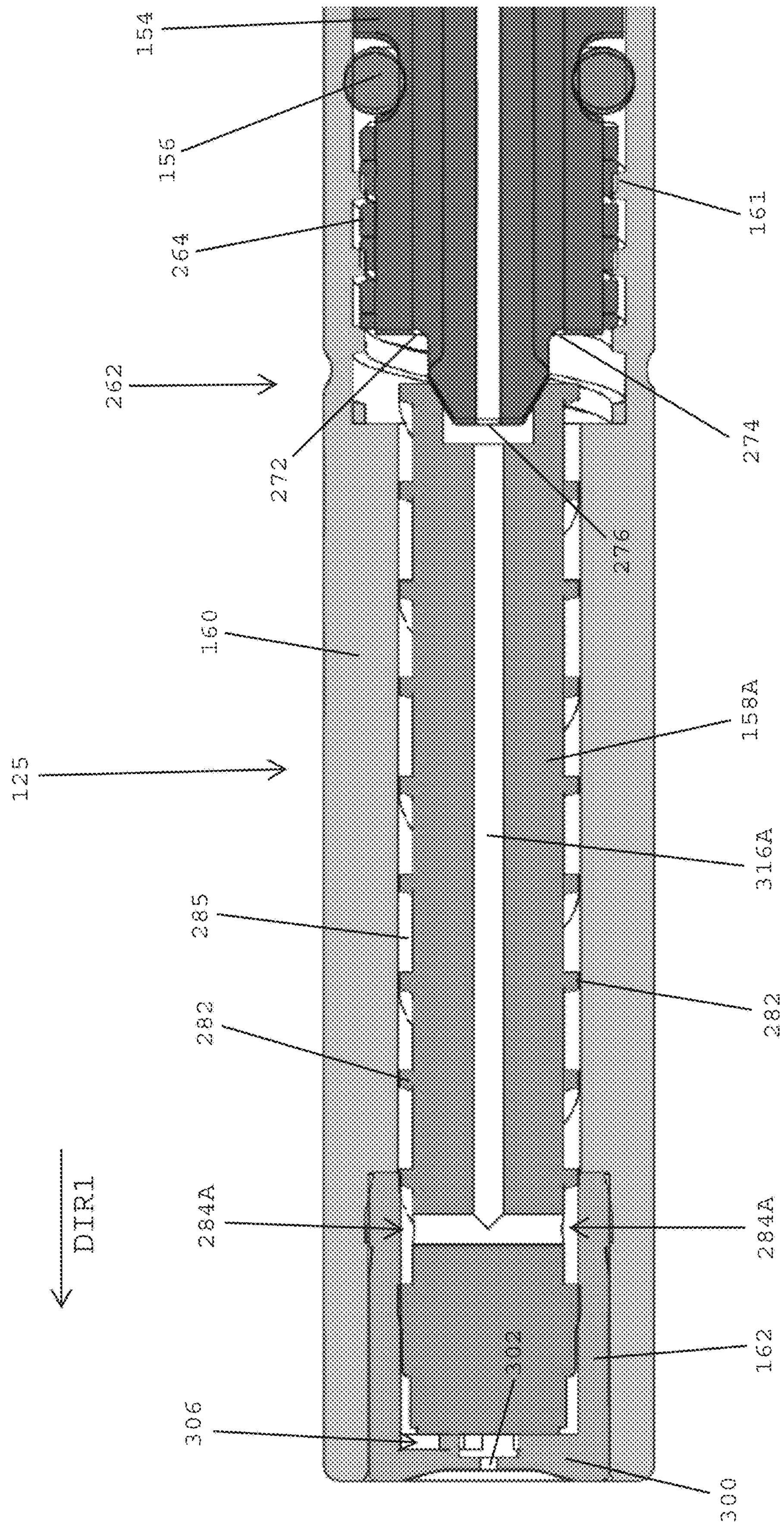
FIG. 28A is a cross-sectional view of a spray tip assembly of an applicator instrument including the mixing element of FIGS. 27A-27D disposed inside the spray tip housing of FIGS. 23A-23D, in accordance with one embodiment of the present patent application.

Referring to FIG. 28A, in one embodiment, the distal end 262 of the fluid connector 154 may be inserted into the opening at the proximal end 288 of the spray tip housing 160, whereupon the external threads 264 at the distal end of the fluid connector 154 engage the internal threads 161 adjacent the proximal end of the spray tip housing 160 for securing the distal end of the fluid connector 154 to the proximal end of the spray tip housing 160. The O-ring 156 preferably forms a fluid-tight seal between the distal end of the fluid connector 154 and the inner surface of the spray tip housing 160. In one embodiment, the third fluid channel 276 at the distal end of the fluid connector 154 is preferably aligned with the third fluid inlet opening 314A and the third fluid conduit 316A of the first mixing element 158A. In one embodiment, the third fluid is preferably dispensed from the third fluid channel 276 and is directed into the third fluid conduit 316A of the mixing element 158A.

Figure 28B:
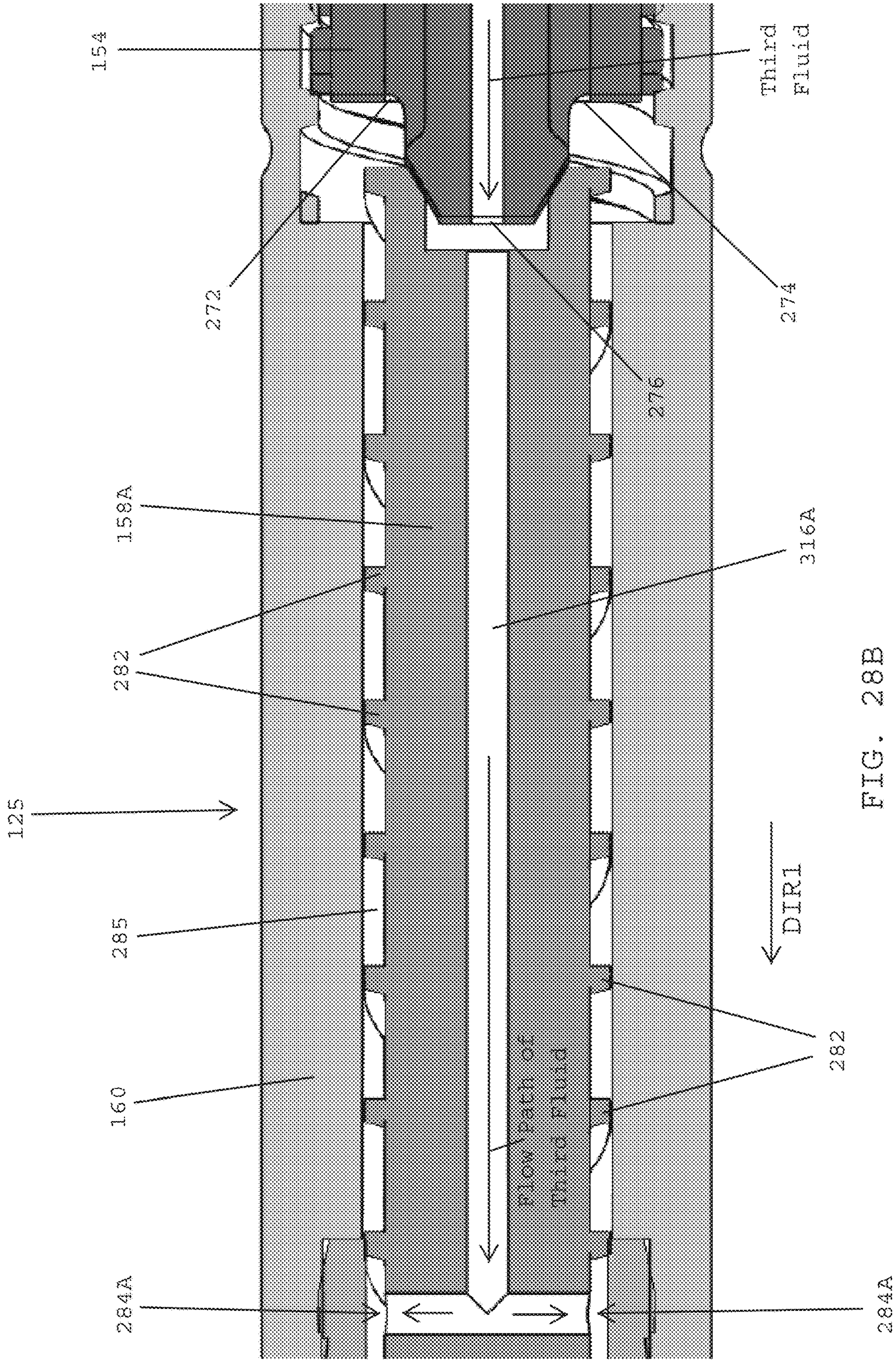
FIG. 28B is a magnified view of a proximal section of the spray tip assembly shown in FIG. 28A.

Referring to FIGS. 28A and 28B, in one embodiment, the first fluid is preferably dispensed from the first fluid channel 272 of the fluid connector 154, and the second fluid is preferably dispensed from the second fluid channel 274 of the fluid connector 154. The dispensed first and second fluids preferably flow downstream (i.e., in the distal direction DIR1) through an annular mixing space 285 that is located between an outer surface of the first mixing element 158A and an inner surface of the spray tip housing 160. As the first and second fluids flow downstream (in the direction DIR1) through the annular mixing space 285, the first and second fluids are preferably mixed together by the static mixing fins 282, which are spaced over the outer surface of the first mixing element 158A.

In one embodiment, after the third fluid exits the third fluid channel 276 of the fluid connector 154, the third fluid preferably travels downstream through the third fluid inlet opening 314A and the third fluid conduit 316A, whereupon the third fluid is directed laterally through the third fluid exit openings 284A and into the annular mixing space 285 for being added into the first mixture of the first and second fluids. In the embodiment shown in FIGS. 28A and 28B, the third fluid is added into the first mixture adjacent the distal end of the first mixing element 158A.

Referring to FIG. 28A, in one embodiment, the final mixture of the first, second and third fluids is desirably directed downstream toward the end wall 300 of the dispensing cap 162, and is further directed into the swirl chamber 306 of the dispensing cap for further mixing. The final mixture is preferably expressed from the distal end of the spray tip assembly 125 via the dispensing opening 302 formed in the end wall 300 of the dispensing cap 162.

Figure 29A:
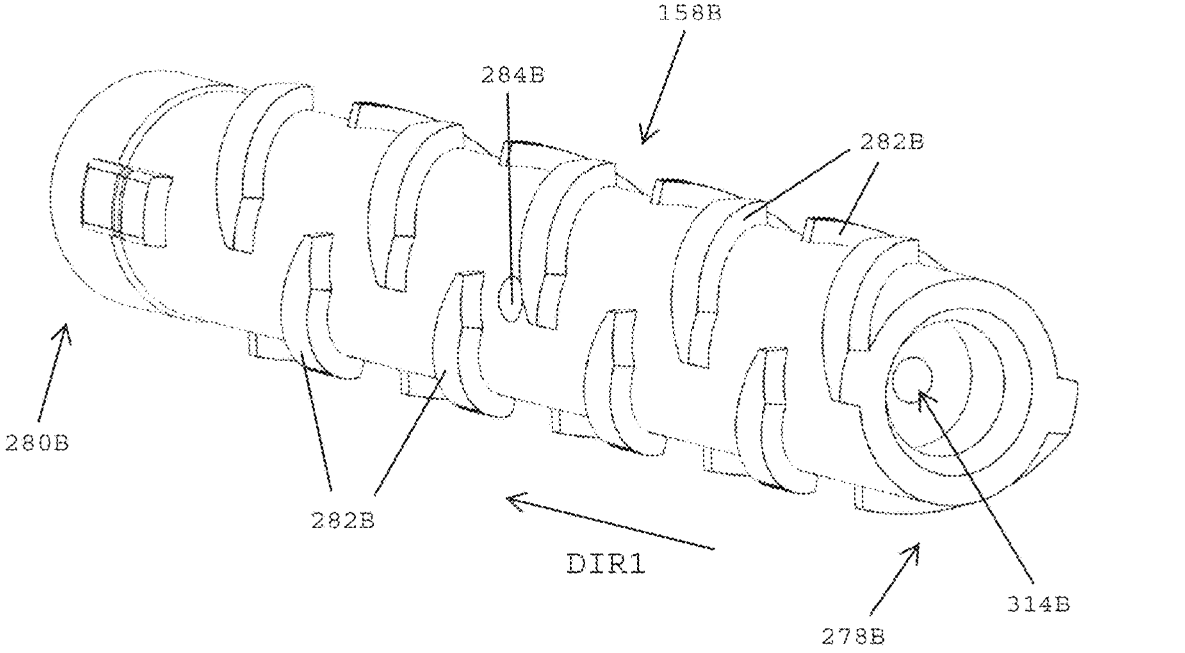
FIG. 29A is a perspective view of a mixing element having third fluid exit openings that are located midway between the proximal and distal ends of the mixing element, in accordance with one embodiment of the present patent application.
Figure 29B:
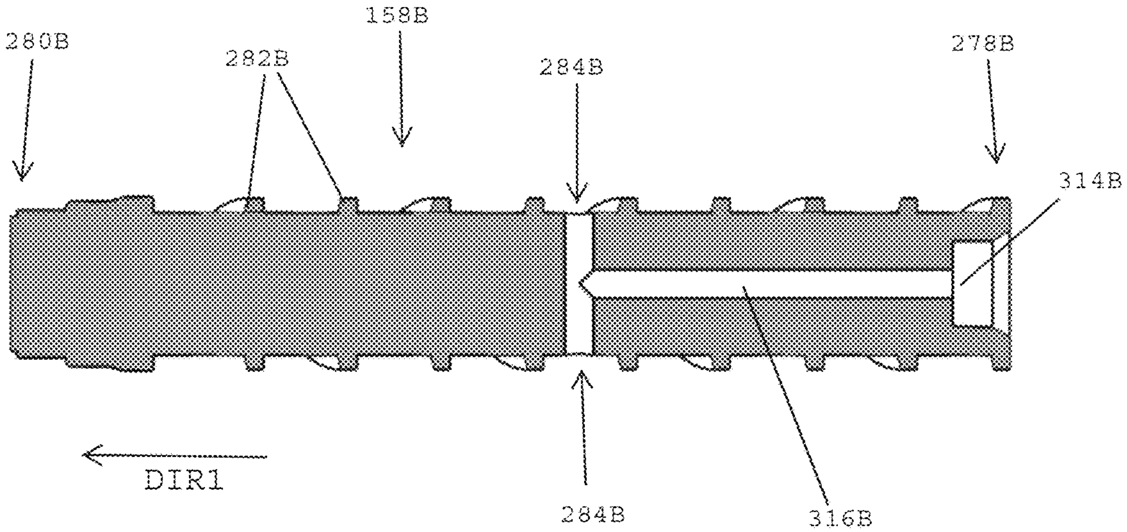
FIG. 29B is a cross-sectional view of the mixing element shown in FIG. 29A.

Referring to FIGS. 29A and 29B, in one embodiment, the second mixing element 158B (FIG. 26) preferably has an outer surface with a cylindrical shape that extends between a proximal end 278B and a distal end 280B of the second mixing element. The outer surface of the second mixing element 158B preferably has a plurality of static mixing fins 282B that are spaced from one another along the length of the second mixing element. The second mixing element 158B preferably has a third fluid inlet opening 314B and a third fluid conduit 316B that extends distally from the third fluid inlet opening 314B to third fluid exit openings 284B, which are located about midway between the proximal end 278B and the distal end 280B of the second mixing element 158B. In one embodiment, the third fluid is added to a first mixture of the first and second fluids via the third fluid exit openings 284B, which are midway between the proximal and distal ends of the second mixing element 158B. A final mixture, comprising the first, second, and third fluids, then flows in the downstream direction DIR1 over the outer surface of the second mixing element 158B. The final mixture is preferably further mixed as it travels downstream over the remaining length of the second mixing element 158B.

Figure 30A:
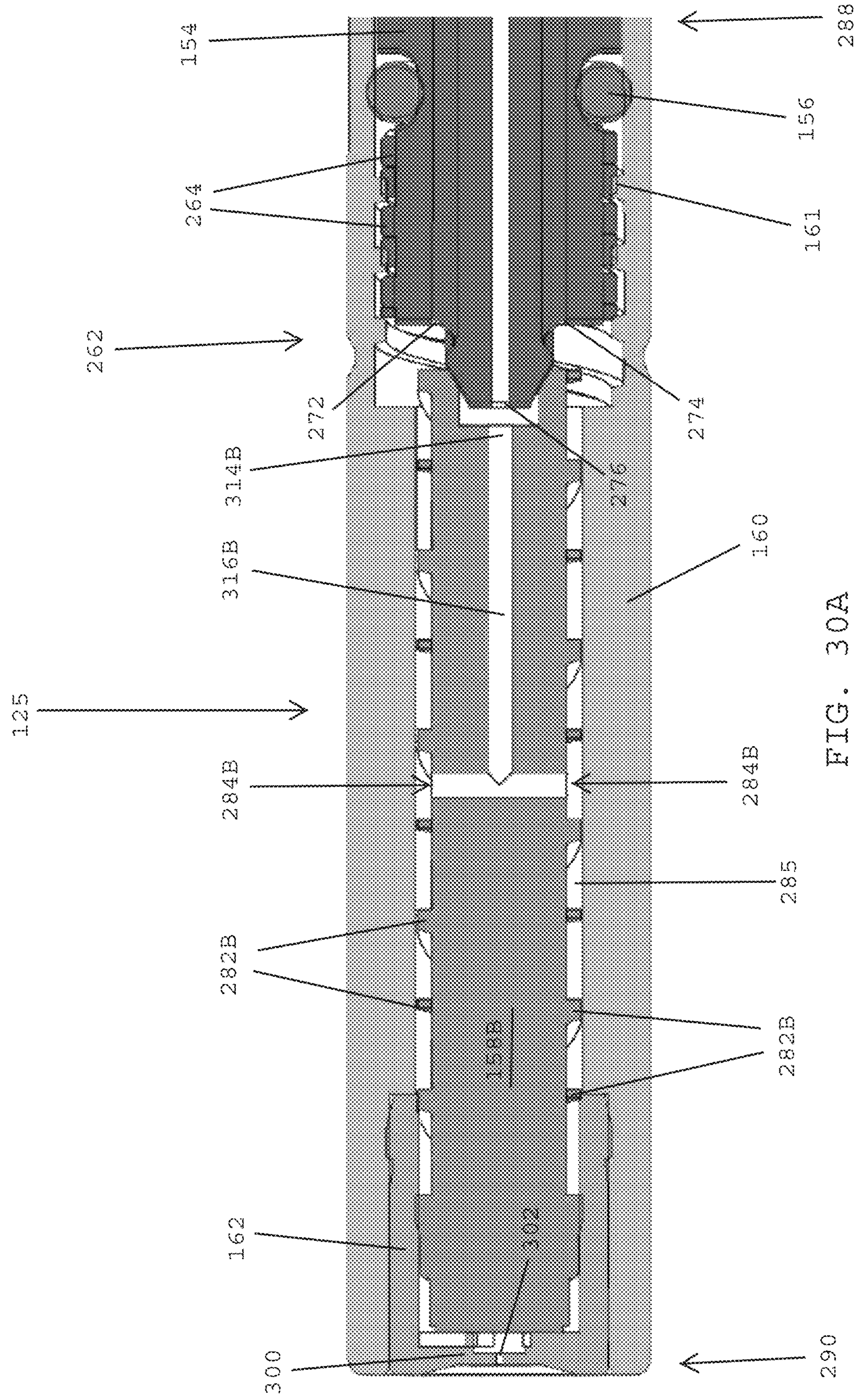
FIG. 30A is a cross-sectional view of a spray tip assembly having the mixing element of FIGS. 29A and 29B disposed inside the spray tip housing of FIGS. 23A-23D, in accordance with one embodiment of the present patent application.
Figure 30B:
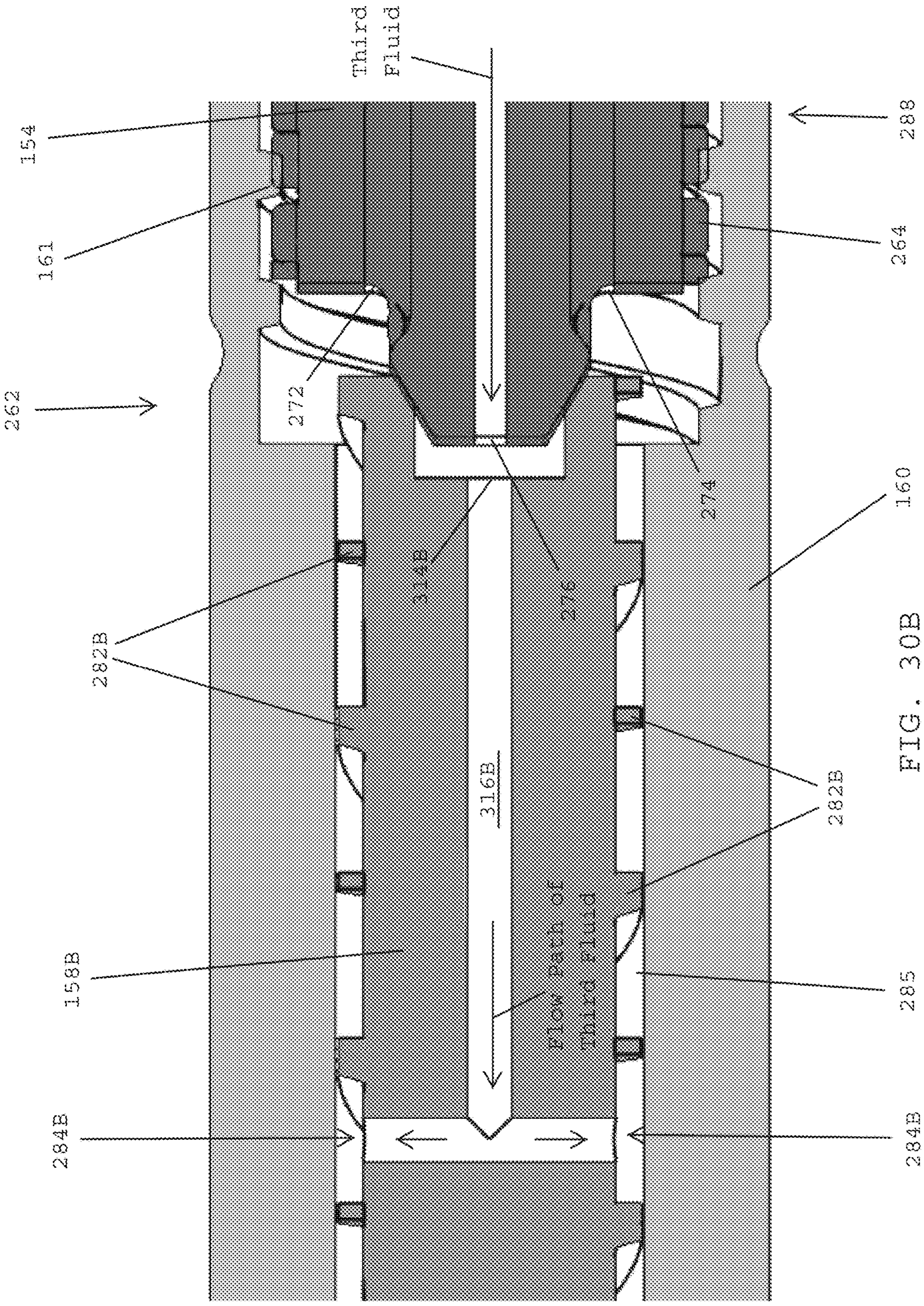
FIG. 30B is a magnified view of a proximal section of the mixing element shown in FIG. 30A.

Referring to FIGS. 30A and 30B, in one embodiment, the distal end 262 of the fluid connector 154 is preferably inserted into the opening at the proximal end 288 of the spray tip housing 160, whereupon the external threads 264 at the distal end of the fluid connector 154 engage the internal threads 161 adjacent the proximal end 288 of the spray tip housing 160 for securing the distal end of the fluid connector 154 with the proximal end of the spray tip housing 160. The O-ring 156 (FIG. 30A) preferably forms a fluid-tight seal between the fluid connector 154 and the inner surface of the outer wall of the spray tip housing 160.

In one embodiment, when the syringe plungers are depressed, the first fluid is preferably dispensed from the first fluid channel 272 of the fluid connector 154 and the second fluid is preferably dispensed from the second fluid channel 274 of the fluid connector 154, whereupon the first and second fluids are mixed together within the annular mixing space 285 that surrounds the second mixing element 158B, thereby forming a first mixture. As the first and second fluids travel downstream toward the distal end 290 (FIG. 30A) of the spray tip housing 160, the first and second fluids are preferably mixed together by the static mixing fins 282B located over the outer surface of the second mixing element 158B.

In one embodiment, the third fluid channel 276 located at the distal end of the fluid connector 154 is preferably aligned with the third fluid inlet opening 314B and the third fluid conduit 316B of the second mixing element 158B. In one embodiment, the third fluid is preferably dispensed from the third fluid channel 276 and into the third fluid inlet opening 314B, whereupon the third fluid is directed downstream into the third fluid conduit 316B of the second mixing element 158B. The third fluid preferably travels downstream to a midway location of the second mixing element 158B, whereupon the third fluid is directed laterally through the third fluid exit openings 284B and into the annular mixing space 285 that surrounds the outer perimeter of the second mixing element 158B for being added into the first mixture of the first and second fluids to form a final mixture.

In the particular embodiment shown in FIGS. 30A and 30B, the first and second fluids are first mixed together at the proximal end of the second mixing element 158B and within the annular mixing space 285 to form a first mixture, and the third fluid is added into the first mixture via the laterally extending third fluid exit openings 284A. The final mixture of the first, second and third fluids is preferably directed through the annular mixing space 285 from a midsection of the second mixing element 158B toward the end wall of the dispensing cap 162, and is further directed into the swirl chamber 306 of the dispensing cap for further mixing. The final mixture is preferably expressed from the distal end of the spray tip assembly 125 via the dispensing opening 302 formed in the end wall 300 of the dispensing cap 162.

Figure 31A:
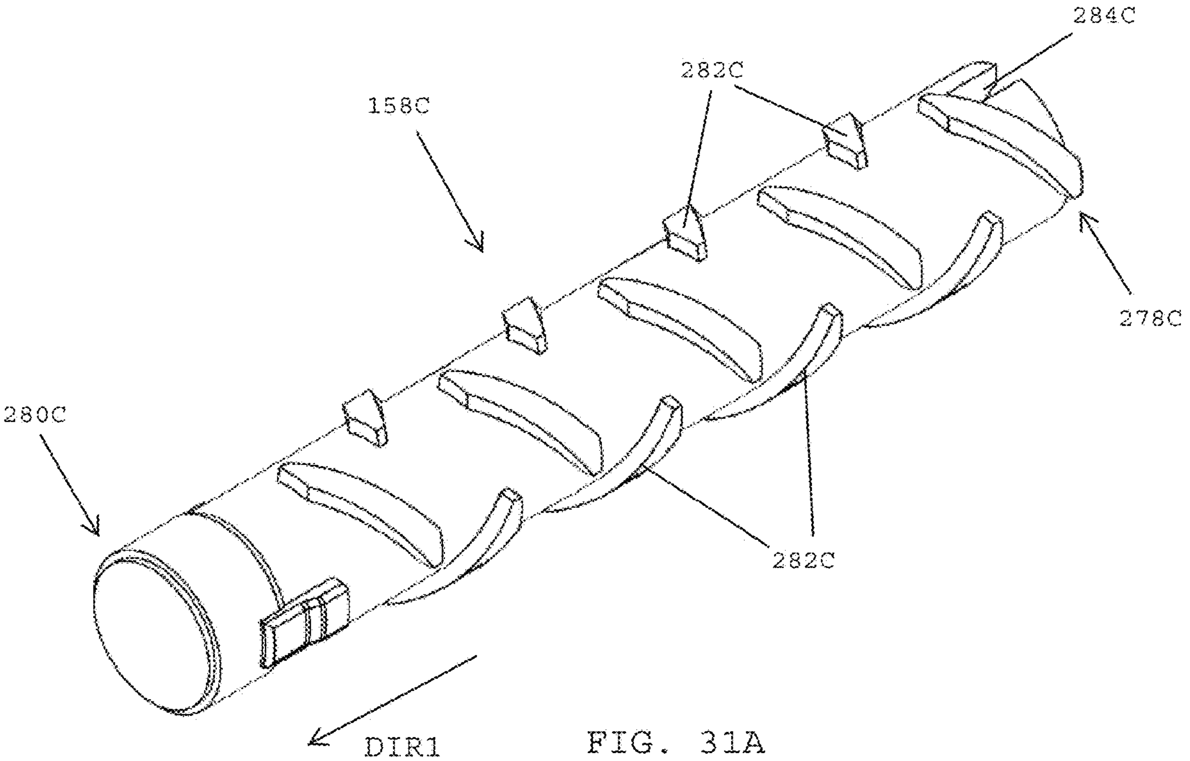
FIG. 31A is a perspective view of a mixing element having third fluid exit openings located adjacent the proximal end of the mixing element, in accordance with one embodiment of the present patent application.
Figure 31B:
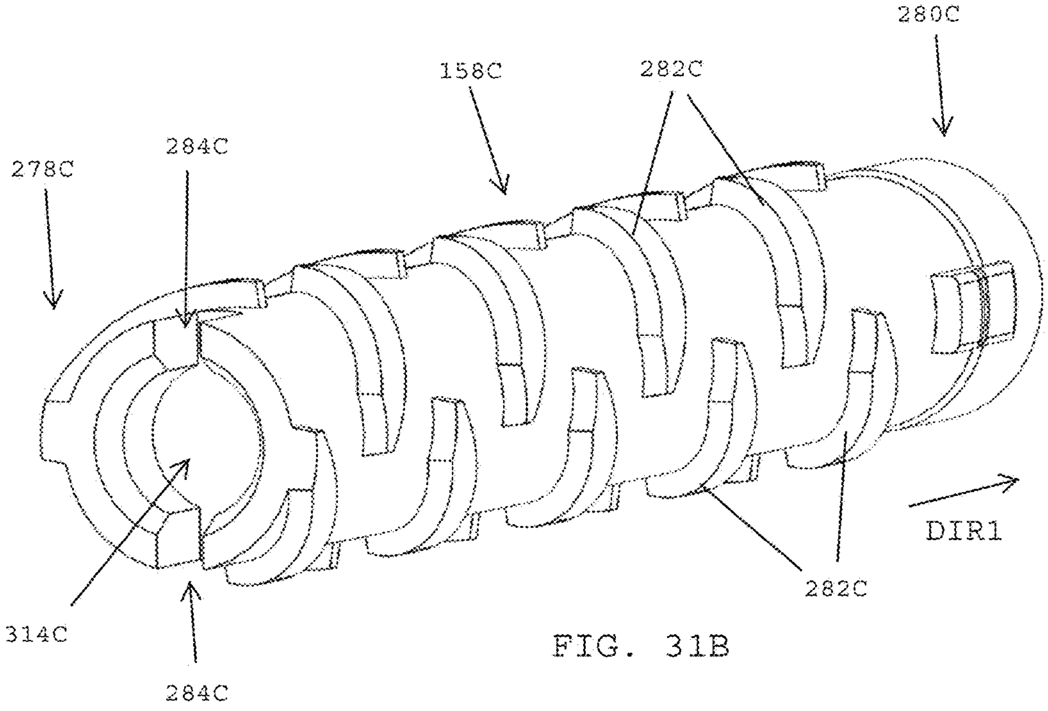
FIG. 31B is a perspective view of a proximal end of the mixing element shown in FIG. 31A.

Referring to FIGS. 31A and 31B, in one embodiment, the third mixing element 158C (FIG. 26) preferably has an outer surface with a cylindrical shape (e.g., a cylindrical rod) that extends between a proximal end 278C and a distal end 280C of the third mixing element. The outer surface of the third mixing element 158C preferably has a plurality of static mixing fins 282C that are spaced from one another along the length of the third mixing element. The third mixing element 158C preferably has a third fluid inlet opening 314C that is in fluid communication with laterally extending third fluid exit openings 284C, which are located adjacent the proximal end 278C of the third mixing element 158C. In one embodiment, the third fluid is added to the first mixture of the first and second fluids via the third fluid exit openings 284C. The final mixture, comprising the first, second, and third fluids, preferably flows in the downstream direction DIR1 toward the distal end 280C of the third mixing element 158C. The static mixing fins 282C mix the first, second and third fluids together as the three fluids flow over the outer surface of the third mixing element 158C.

Figure 32A:
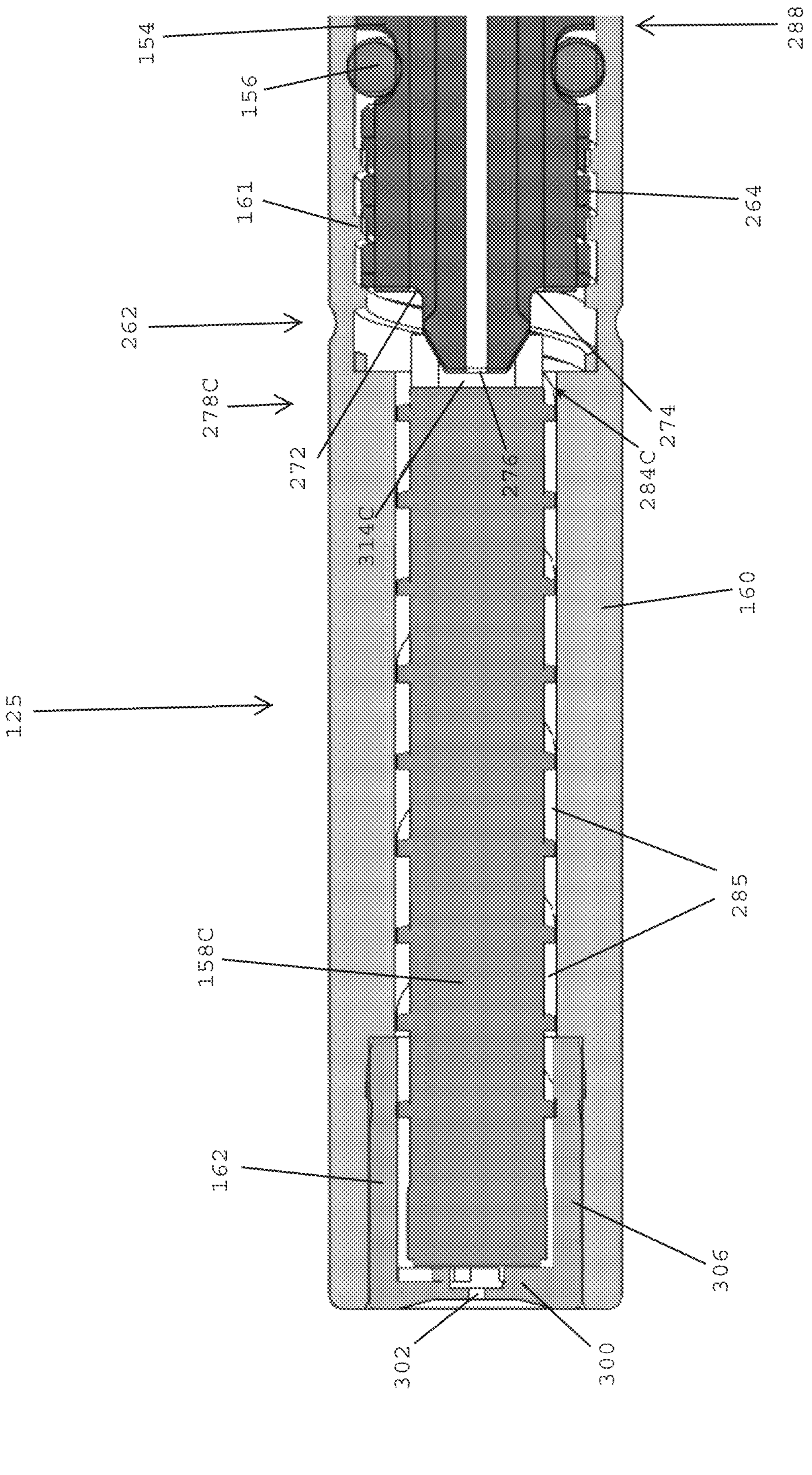
FIG. 32A is a cross-sectional view of a spray tip assembly including the mixing element of FIGS. 31A-31B disposed inside the spray tip housing of FIGS. 23A-23D, in accordance with one embodiment of the present patent application.
Figure 32B:
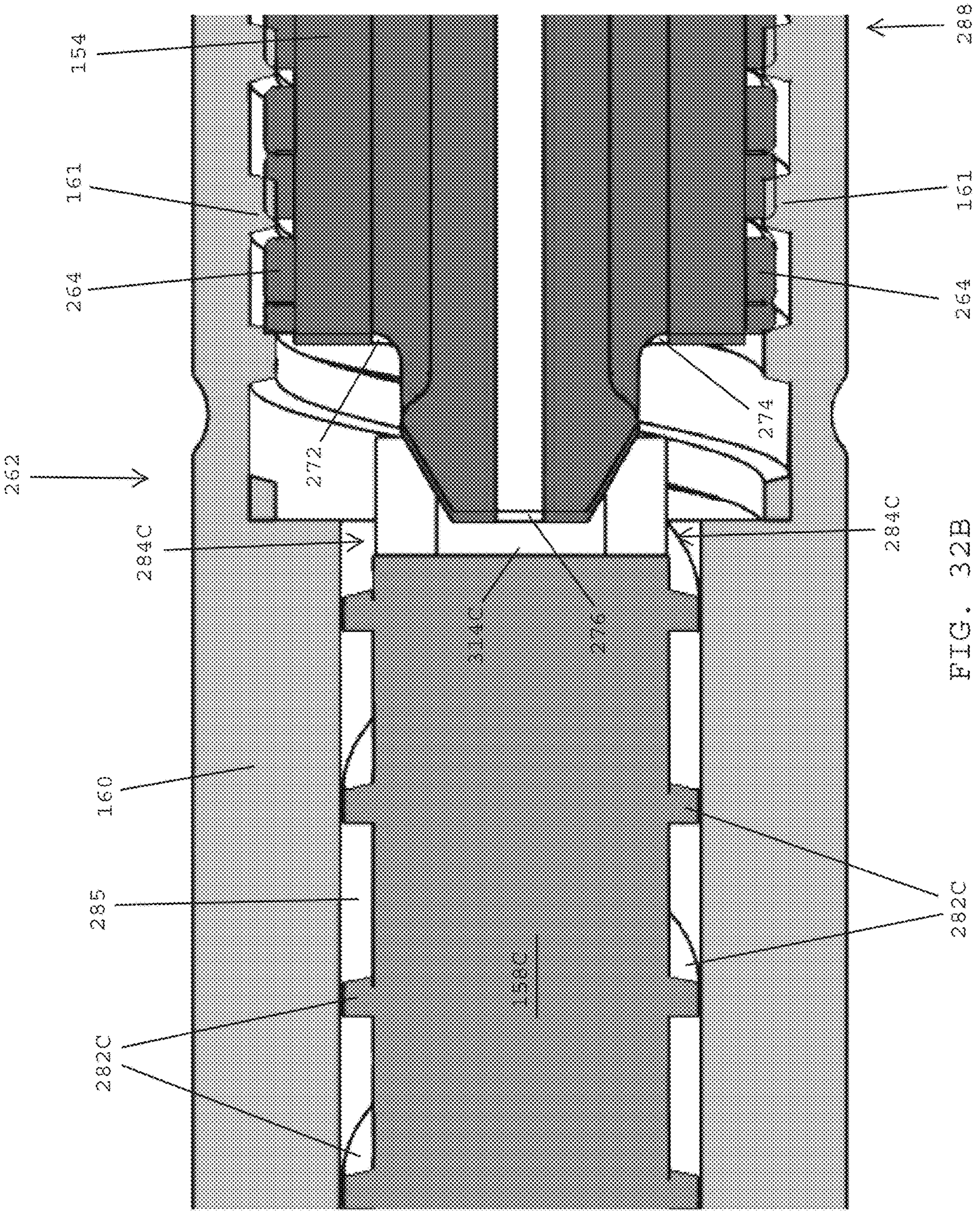
FIG. 32B is a magnified view of a proximal section of the spray tip assembly shown in FIG. 32A.

Referring to FIGS. 32A and 32B, in one embodiment, the distal end 262 of the fluid connector 154 is desirably inserted into the opening at the proximal end 288 of the spray tip housing 160, whereupon the external threads 264 at the distal end of the fluid connector 154 engage the internal threads 161 adjacent the proximal end 288 of the spray tip housing 160 for securing the distal end of the fluid connector 154 with the proximal end of the spray tip housing 160. The O-ring 156 (FIG. 32A) preferably forms a fluid-tight seal between the fluid connector 154 and the inner surface of the outer wall of the spray tip housing 160.

In one embodiment, when syringe plungers are depressed, the first fluid is preferably dispensed from the first fluid channel 272 of the fluid connector 154 and the second fluid is preferably dispensed from the second fluid channel 274 of the fluid connector, whereupon the first and second fluids are mixed together within an annular mixing space 285 located between the outer surface of the third mixing element 158C and an inner surface of the spray tip housing 160 to form a first mixture.

In one embodiment, the third fluid channel 276, located at the distal end of the fluid connector 154, is preferably aligned with the third fluid inlet opening 314C of the third mixing element 158C. In one embodiment, the third fluid is preferably dispensed from the third fluid channel 276 of the fluid connector 154 and into the third fluid inlet opening 314C, whereupon the third fluid is directed laterally through the third fluid exit openings 284C located adjacent the proximal end 278C of the third mixing element 158C. The third fluid is preferably directed through the third fluid exit openings 284C and into the annular mixing space 285 that surrounds the outer perimeter of the third mixing element 158C for being added into the first mixture of the first and second fluids, which forms a final mixture.

In the particular embodiment shown in FIGS. 32A and 32B, the final mixture of the first, second and third fluids are desirably joined together adjacent the proximal end 278C of the third mixing element 158C, whereupon the final mixture (i.e., a mixture of the first, second and third fluids) flows downstream in the direction DIR1 as it is further mixed by the fluid mixing fins 282C spaced over the outer surface of the third mixing element 158C. The final mixture preferably flows downstream through the annular mixing space 285 toward the end wall 300 of the dispensing cap 162, whereupon the final mixture flows into the swirl chamber 306 of the dispensing cap 162 for further mixing. The final mixture is preferably expressed from the distal end of the spray tip assembly 125 via the dispensing opening 302 formed in the end wall 300 of the dispensing cap 162.

Figure 33:
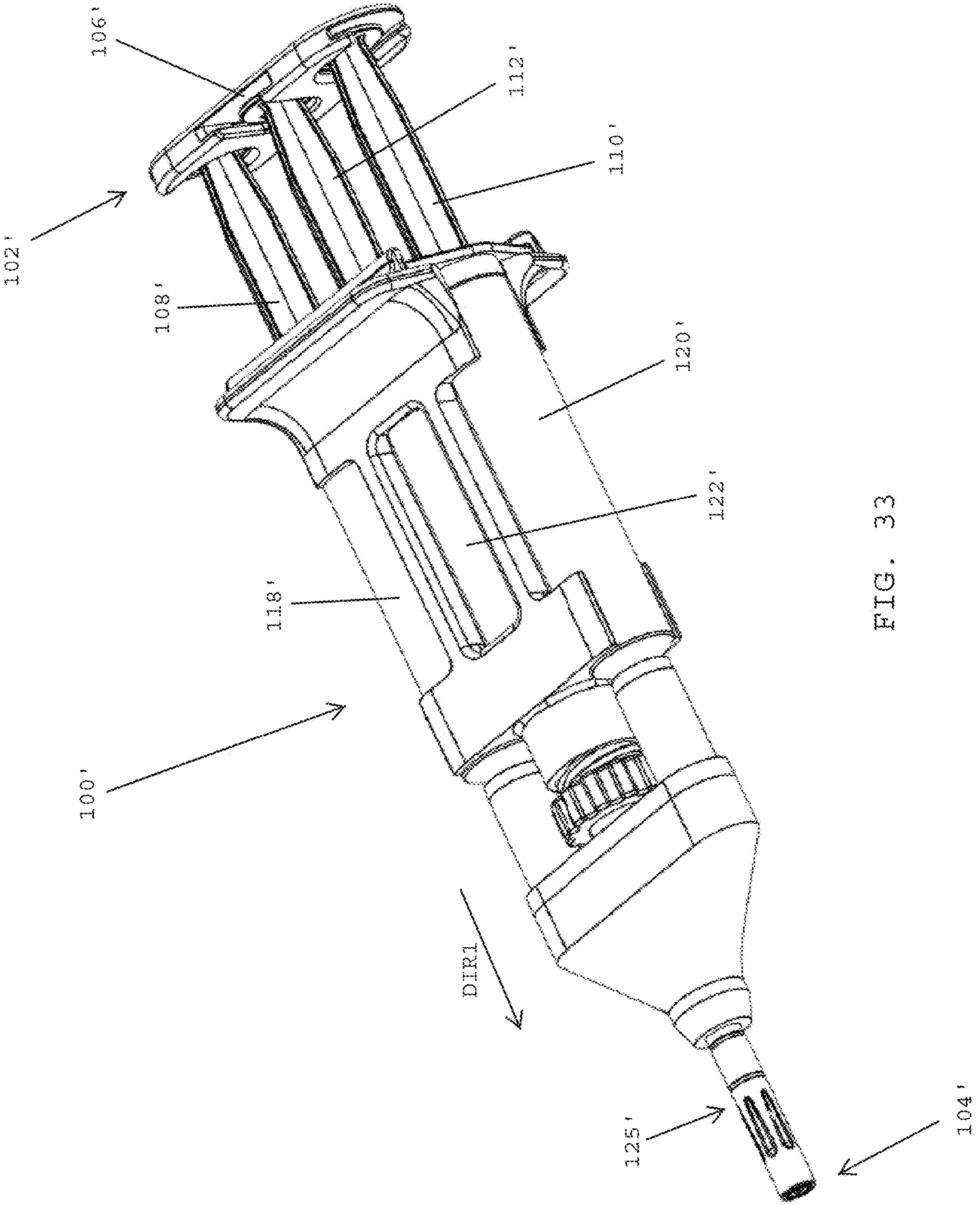
FIG. 33 is a perspective view of an applicator instrument for dispensing a multiple component adhesive, in accordance with one embodiment of the present patent application.
Figure 34:
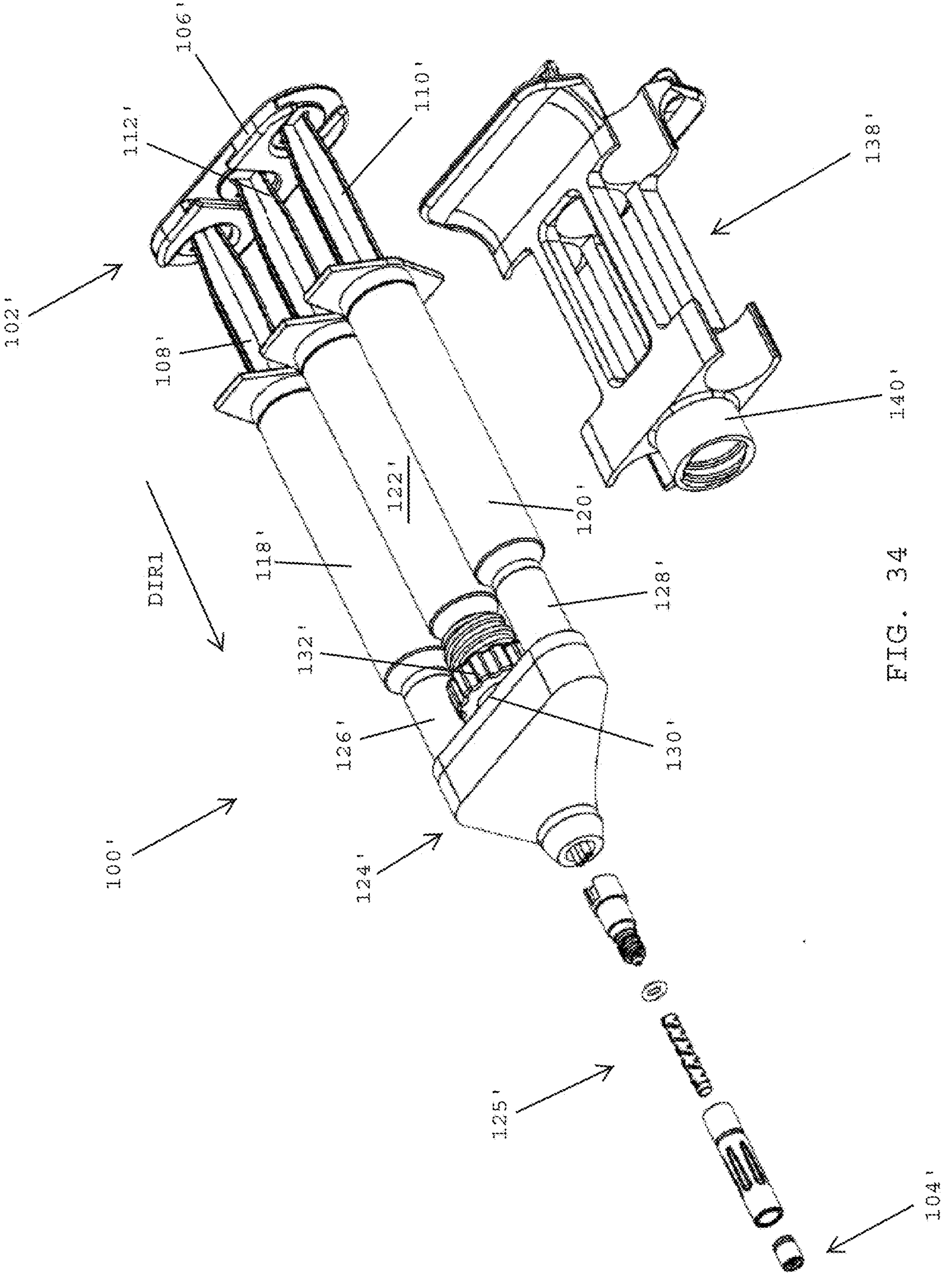
FIG. 34 is a partially exploded view of the applicator instrument shown in FIG. 33.

Referring to FIGS. 33 and 34, in one embodiment, an applicator instrument 100' for mixing and expressing a composition, such as a biocompatible reactive formulation, preferably has one or more of the structural elements and/or features shown and described above in FIGS. 1A-32B. In one embodiment, the applicator instrument 100' preferably has a proximal end 102' and a distal end 104' including a spray tip assembly 125' located at the distal end. In one embodiment, the applicator instrument 100' is preferably configured for mixing together two or more fluid components (e.g., three components) to form a final mixture of a biocompatible reactive formulation (e.g., a tissue adhesive; a tissue sealant). In one embodiment, the final mixture of the biocompatible reactive formulation is preferably expressed from the spray tip assembly 125', which is located at the distal end 104' of the applicator instrument 100'.

In one embodiment, the applicator instrument 100' preferably includes three syringe plungers 108', 110', and 112' that have the same size, shape and dimension. In one embodiment, the applicator instrument 100' preferably includes three syringe barrels 118', 120', and 122' that have the same size, shape, configuration, and dimension.

In one embodiment, the applicator instrument 100' preferably includes the first syringe barrel 118' that is adapted to contain a first reactive fluid of a multiple component tissue adhesive. In one embodiment, the first syringe barrel 118' is adapted to receive the first syringe plunger 108', which may be used for forcing the first reactive fluid from the distal end of the first syringe barrel 118'.

In one embodiment, the applicator instrument 100 preferably includes the second syringe barrel 120' that is adapted to contain a second reactive fluid of the multiple component tissue adhesive. In one embodiment, the second syringe barrel 120' is adapted to receive the second syringe plunger 110', which may be used for forcing the second reactive fluid from the distal end of the second syringe barrel 120'. The first and second reactive fluids may be mixed together to form a first mixture. In one embodiment, the first and second reactive fluids may be adapted for chemically reacting with one another to form a biocompatible reactive formulation, such as a tissue adhesive or a tissue sealant.

In one embodiment, the applicator instrument 100 desirably includes the third syringe barrel 122', which is adapted to receive the third syringe plunger 112'. In one embodiment, the third syringe barrel 122' is adapted to contain a third fluid component (e.g., a neutralizing buffer; a diluent, such as $H_2O$). In one embodiment, the third syringe plunger 112' may be depressed for forcing the third fluid component from the distal end of the third syringe barrel 122', whereupon the third fluid may be added into and/or mixed with the first mixture of the first and second reactive fluids.

In one embodiment, proximal ends of the syringe plungers 108', 110', and 112' are preferably secured to a plunger head 106', which may be depressed in the distal direction DIR1 for simultaneously moving the syringe plungers in the distal direction DIR1 to simultaneously dispense the first, second and third fluids from the respective first, second and third syringe barrels 118', 120', and 122'.

In one embodiment, the first, second and third syringe barrels 118', 120', and 122' are the same size and may have respective cross-sectional diameters that are the same size. In one embodiment, the respective first, second, and third syringe barrels 118', 120', and 122' are configured to hold an equal volume of fluid. Thus, the volume of the first fluid held in the first syringe barrel 118' may equal the volume of the second fluid held in the second syringe barrel 120', which, in turn, may be equal to the volume of the third fluid held in the third syringe barrel 122'.

In one embodiment, the applicator instrument 100' preferably includes a fluid manifold 124' that is located downstream from the distal ends of the first, second and third syringe barrels 118', 120', 122'. In one embodiment, the fluid manifold 124' preferably includes a first connector 126' adapted to receive a distal end of the first syringe barrel 118', a second connector 128' adapted to receive a distal end of the second syringe barrel 120', and a third connector 130' adapted to receive a distal end of the third syringe barrel 122'.

In one embodiment, the first connector 126' of the fluid manifold 124' is preferably in fluid communication with the first syringe barrel 118'. In one embodiment, a first component of a multiple component adhesive that is pre-loaded into the first syringe barrel 118' may be forced to flow into the first connector 126' of the fluid manifold 124', such as by depressing the first syringe plunger 108'.

In one embodiment, the second connector 128' of the fluid manifold 124' is preferably in fluid communication with the second syringe barrel 120'. In one embodiment, a second component of a multiple component adhesive that is pre-loaded into the second syringe barrel 120' may be forced to flow into the second connector 128' of the fluid manifold 124', such as by depressing the second syringe plunger 110'.

In one embodiment, the third connector 130' of the fluid manifold 124' is preferably in fluid communication with the third syringe barrel 122'. In one embodiment, a third component of a multiple component adhesive that is pre-loaded into the third syringe barrel 122' may be forced to flow into the third connector 130' of the fluid manifold 124', such as by depressing the third syringe plunger 112'.

In one embodiment, the applicator instrument 100' preferably includes a syringe barrel support frame 138' that is adapted to receive and hold the first, second and third syringe barrels 118', 120', and 122'. The syringe barrel support frame 138' desirably holds the syringe barrels 118', 120', 122' together for stabilizing the syringe barrels and enhancing the structural integrity and consistent performance of the applicator instrument 100.

In one embodiment, the syringe barrel support frame 138 preferably has a distal end with a distal projection 140' having internal threads, which are adapted to mesh with external threads of a connecting nut 132' for securing the distal end of the syringe barrel support frame 138' to the connecting nut 132'. In one embodiment, the connecting nut 132' may also be utilized for securing both the distal projection 140' of the syringe barrel support frame 138' and the distal end of the third syringe barrel 122' to the second connector 130' of the fluid manifold 124'.

Figure 35:
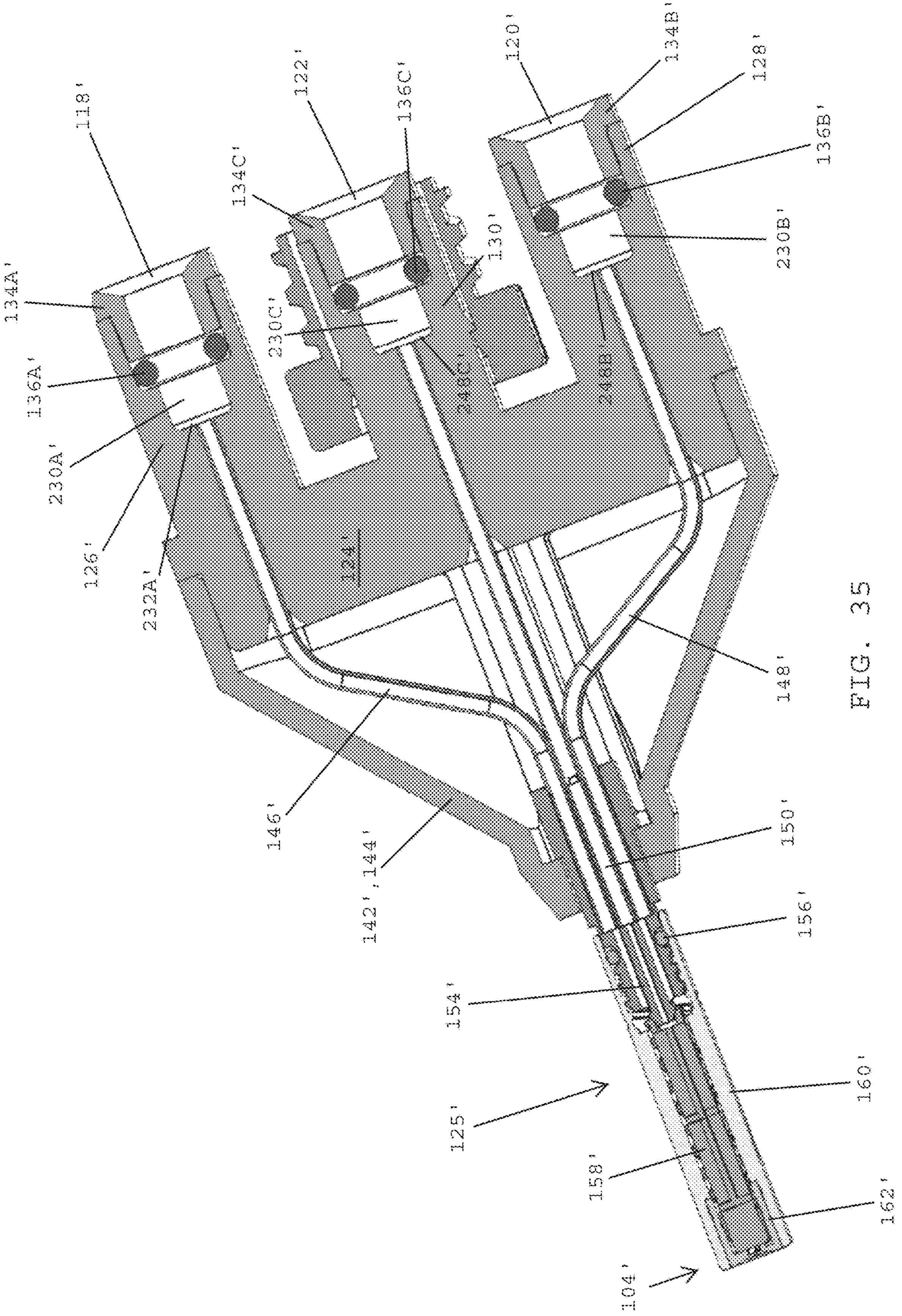
FIG. 35 is a cross-sectional view of a distal end of the applicator instrument shown in FIG. 33.

Referring to FIG. 35, in one embodiment, the distal end 230A' of the first syringe barrel 118' is inserted into the third fluid inlet opening of the first connector 126' of the fluid manifold 124'. A first O-ring retainer 134A' and a first O-ring 136A' are utilized to form a fluid-tight coupling between the distal end 230' of the first syringe barrel 118' and the first connector 126' of the fluid manifold 124'.

In one embodiment, the distal end 230B' of the second syringe barrel 120' is inserted into the third fluid inlet opening of the second connector 128' of the fluid dispensing manifold 124'. A second O-ring retainer 134B' and a second O-ring 136B' are utilized for forming a fluid-tight coupling between the distal end of the second syringe barrel 120' and the second connector 128' of the fluid manifold 124'.

In one embodiment, the distal end 230C' of the third syringe barrel 122' is inserted into the third fluid inlet opening of the third connector 130' of the fluid dispensing manifold 124'. A third O-ring retainer 134C' and a third O-ring 136C' are utilized for forming a water-tight coupling between the distal end of the third syringe barrel 122' and the third connector 130' of the fluid manifold 124'.

In one embodiment, the first fluid dispensing opening 232A' located at the distal end of the first syringe barrel 118' is preferably in fluid communication with the first fluid tube 146' for directing the first fluid of a mixture from the first syringe barrel 118' into the first fluid tube 146'.

In one embodiment, the second fluid dispensing opening 248B' located at the distal end 230B' of the second syringe barrel 120' is preferably in fluid communication with the second fluid tube 148' for directing the second fluid of a mixture from the second syringe barrel 120' into the second fluid tube 148'.

In one embodiment, the third dispensing opening 248C' at the distal end 230C' of the third syringe barrel 122' is preferably in fluid communication with the third fluid tube 150' for directing the third fluid of the mixture from the third syringe barrel 122' into the third fluid tube 150'.

In one embodiment, the distal end 104' of the applicator instrument 100' preferably includes the spray tip assembly 125', which is secured to the distal ends of the respective upper and lower fluid tube enclosures 142', 144'. In one embodiment, the spray tip assembly 125' preferably includes the fluid connector 154' having a distal end that is secured to a proximal end of the spray tip housing 160'. An O-ring 156' forms a fluid-tight seal between the fluid connector 154' and the spray tip housing 160'. A mixing element 158' is disposed inside the spray tip housing 160'. A dispensing cap 162' is preferably assembled within an opening provided at the distal end of the spray tip housing 160'.

Figure 36:
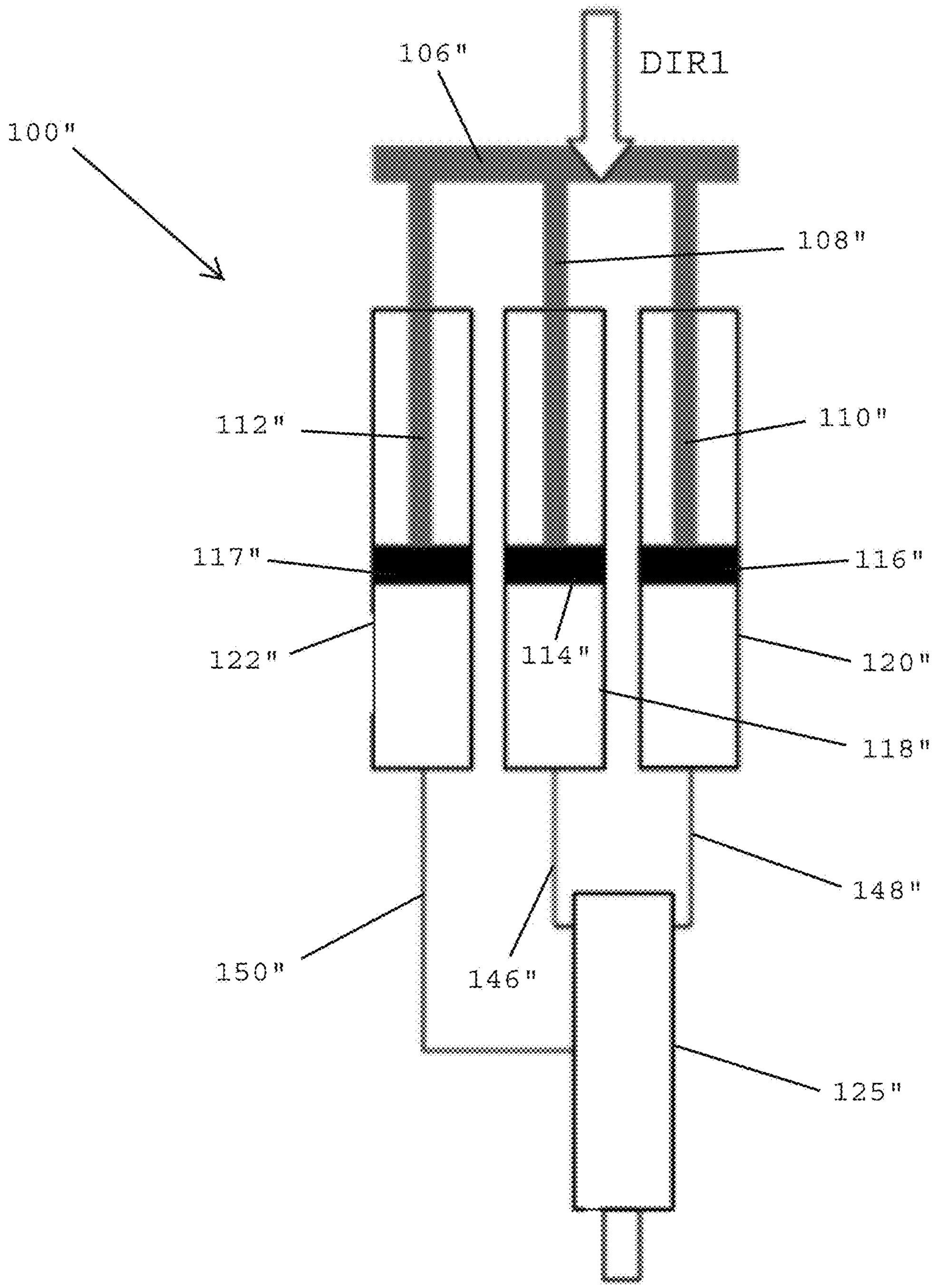
FIG. 36 is a schematic view of an applicator instrument for mixing and expressing a three component tissue adhesive, in accordance with one embodiment of the present patent application.

Referring to FIG. 36, in one embodiment, a dispensing system 100" for dispensing a tissue adhesive preferably includes a first syringe barrel 118" adapted to contain a first fluid having a first reactive component, a second syringe barrel 120" adapted to contain a second fluid having a second reactive component, and a third syringe barrel 122" adapted to receive a third fluid (e.g., a neutralizing buffer; a diluent such as $H_2O$). In one embodiment, a first syringe plunger 108" having a first piston 114" secured to a distal end thereof is assembled with the first syringe barrel 118", a second syringe plunger 110" having a second piston 116" secured to a distal end thereof is assembled with the second syringe barrel 120", and a third syringe plunger 112" having a third piston 117" secured to a distal end thereof is assembled with the third syringe barrel 122".

In one embodiment, proximal ends of the first, second and third syringe plungers 108", 110" and 112" are desirably secured to the plunger head 106". The plunger head 106" may be pushed in the distal direction DIR1 for forcing the pistons 114", 116" and 117" toward the distal ends of the respective syringe barrels 118", 120", and 122" to simultaneously force the first, second and third fluids from the distal ends of the syringe barrels.

In one embodiment, when the plunger head 106" is depressed, the first fluid in the first syringe barrel 118" flows downstream through the first fluid tube 146" and into the spray tip assembly 125", and the second fluid in the second syringe barrel 120" flows downstream through the second fluid tube 148" and into the spray tip assembly 125" for being mixed with the first fluid to form a first mixture. Simultaneously, the third fluid in the third syringe barrel 122" flows downstream through the third fluid tube 150" and into the spray tip assembly 125" for being added into the first mixture of the first and second fluids. The third fluid is preferably added into the first mixture of the first and second fluids at a location that is downstream of the location where the first and second fluids are first mixed together within the spray tip assembly 125". The location where the third fluid tube 150" enters the spray tip assembly 125" may be modified for changing how the first and second reactive components react with one another. A dispensing cap 162" is preferably provided at the distal end of the spray tip assembly 125".

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for dispensing a biocompatible reactive formulation, the system comprising:
- a spray tip housing having a proximal end, a distal end, an outer wall that extends from said proximal end to said distal end of said spray tip housing, and an elongated conduit surrounded by said outer wall that extends from said proximal end to said distal end of said spray tip housing;
- a fluid connector secured to said proximal end of said spray tip housing and opposing a proximal end of a mixing element, said fluid connector including:
  - first and second fluid channels in fluid communication with a mixing chamber, said first and second fluid channels comprising first and second fluid inlet openings, first and second fluid exit openings, and first and second fluid conduits extending between said first and second fluid inlet openings and said first and second fluid exit openings, respectively; and
  - a third fluid channel in fluid communication with a third fluid inlet opening of said mixing element;
- said mixing element disposed within said elongated conduit of said spray tip housing; and
- said mixing chamber located between an outer surface of said mixing element and an inner surface of said outer wall of said spray tip housing;
- said mixing element including:
  - said proximal end adjacent said proximal end of said spray tip housing and a distal end adjacent said distal end of said spray tip housing;
  - said third fluid inlet opening at said proximal end of said mixing element; and
  - one or more third fluid exit openings formed in said outer surface of said mixing element that are in fluid communication with said third fluid inlet opening, wherein said one or more third fluid exit openings extend laterally through said mixing element to said outer surface of said mixing element for being in fluid communication with said mixing chamber.

2. The system as claimed in claim 1, wherein said mixing element further comprises a third fluid conduit extending distally from said third fluid inlet opening of said mixing element toward said distal end of said mixing element for interconnecting said third fluid inlet opening and said one or more third fluid exit openings of said mixing element.

3. The system as claimed in claim 2, wherein said fluid connector has a proximal end and a distal end, and wherein said distal end of said fluid connector is disposed within said elongated conduit of said spray tip housing and opposes said proximal end of said mixing element.

4. The system as claimed in claim 3, wherein said first, second and third fluid channels of said fluid connector extend from said proximal end to said distal end of said fluid connector, and wherein said first, second and third fluid channels are isolated from one another within said fluid connector.

5. The system as claimed in claim 4, wherein said third fluid channel of said fluid connector extends through a central region of said fluid connector, and wherein said first and second fluid channels of said fluid connector extend on opposite sides of said third fluid channel.

6. The system as claimed in claim 2, wherein said one or more third fluid exit openings are located adjacent said distal end of said mixing element, and wherein said third fluid conduit of said mixing element extends to said distal end of said mixing element for being in fluid communication with said one or more third fluid exit openings.

7. The system as claimed in claim 2, wherein said one or more third fluid exit openings are located midway between said proximal and distal ends of said mixing element, and wherein said third fluid conduit of said mixing element extends to said midway location of said mixing element for being in fluid communication with said one or more third fluid exit openings.

8. The system as claimed in claim 1, wherein said one or more third fluid exit openings are located adjacent said proximal end of said mixing element, and wherein said third fluid inlet opening is in fluid communication with said one or more third fluid exit openings.

9. The system as claimed in claim 2, further comprising:

said inner surface of said outer wall of said spray tip housing comprising internal threads located adjacent said proximal end of said spray tip housing; and said distal end of said fluid connector having external threads that are configured to mesh with said internal threads of said spray tip housing for securing said distal end of said fluid connector with said proximal end of said spray tip housing.

10. The system as claimed in claim 9, wherein said first fluid channel of said fluid connector is aligned with a first lateral side of said mixing chamber, said second fluid channel of said fluid connector is aligned with a second lateral side of said mixing chamber, and said third fluid channel of said fluid connector is aligned with said third fluid inlet opening and said third fluid conduit of said mixing element.

11. The system as claimed in claim 2, further comprising:

a first chamber containing a first fluid having a first reactive component, wherein said first chamber is in fluid communication with said first fluid channel of said fluid connector;

a second chamber containing a second fluid having a second reactive component that is reactive with said first reactive component, wherein said second chamber is in fluid communication with said second fluid channel of said fluid connector; and a third chamber containing a third fluid, wherein said third chamber is in fluid communication with said third fluid channel of said fluid connector;

wherein said system is configured to direct said first and second fluids in series through said respective first and second fluid channels of said fluid connector and into said mixing chamber for forming a first mixture, and wherein said system is configured to direct said third fluid in series through said third fluid channel of said fluid connector, into said third fluid inlet opening of said mixing element, through said third fluid conduit of said mixing element, and laterally through said one or more third fluid exit openings of said mixing element for entering into said mixing chamber for being added into said first mixture of said first and second fluids to form a final mixture.

12. The system as claimed in claim 11, further comprising a dispensing cap disposed within said elongated conduit of said spray tip housing and secured to said distal end of said spray tip housing for opposing said distal end of said mixing element, wherein said dispensing cap comprises a dispensing opening that is in fluid communication with a distal end of said mixing chamber for expressing said final mixture of said first, second, and third fluids.

13. A system for dispensing a biocompatible reactive formulation, the system comprising:

a first chamber containing a first fluid having a first reactive component;

a second chamber containing a second fluid having a second reactive component that is reactive with said first reactive component;

a third chamber containing a third fluid;

a spray tip assembly that is configured for spraying a final mixture of said first, second and third fluids, said spray tip assembly comprising:

a spray tip housing having a proximal end, a distal end, an outer wall that extends from said proximal end to said distal end of said spray tip housing, and an elongated conduit surrounded by said outer wall that extends from said proximal end to said distal end of said spray tip housing;

a fluid connector secured to said proximal end of said spray tip housing and opposing a proximal end of a mixing element, said fluid connector including:

first and second fluid channels in fluid communication with a mixing chamber, said first and second fluid channels comprising first and second fluid inlet openings, first and second fluid exit openings, and first and second fluid conduits extending between said first and second fluid inlet openings and said first and second fluid exit openings, respectively; and a third fluid channel in fluid communication with a third fluid inlet opening of said mixing element;

said mixing element disposed within said elongated conduit of said spray tip housing; and said mixing chamber located between an outer surface of said mixing element and an inner surface of said outer wall of said spray tip housing, said mixing element including:

said proximal end adjacent said proximal end of said spray tip housing and a distal end adjacent said distal end of said spray tip housing, said third fluid inlet opening at said proximal end of said mixing element, and one or more third fluid exit openings formed in said outer surface of said mixing element that are in fluid communication with said third fluid inlet opening and that extend laterally to said outer surface of said mixing element for being in fluid communication with said mixing chamber; and a pump assembly coupled with said first, second and third chambers for simultaneously forcing said first, second and third fluids to flow through said first, second and third fluid channels of said fluid connector and into said proximal end of said spray tip housing.

14. The system as claimed in claim 13, wherein said mixing element further comprises a third fluid conduit extending distally from said third fluid inlet opening of said mixing element toward the distal end of said mixing element, and wherein said third fluid conduit is in fluid communication with said one or more third fluid exit openings for directing said third fluid from said third fluid inlet opening to said one or more third fluid exit openings.

15. The system as claimed in claim 14, further comprising:

said inner surface of said outer wall of said spray tip housing comprising internal threads located adjacent said proximal end of said spray tip housing;

said distal end of said fluid connector having external threads that are configured to mesh with said internal threads of said spray tip housing for securing said distal end of said fluid connector with said proximal end of said spray tip housing;

wherein said first fluid channel of said fluid connector is aligned with a first lateral side of said mixing chamber, said second fluid channel of said fluid connector is aligned with a second lateral side of said mixing chamber, and said third fluid channel of said fluid connector is aligned with said third fluid inlet opening and said third fluid conduit of said mixing element.

* * * * *